【12】 United States Patent
Khaled et al.

US012097264B2

(10) Patent No.: US 12,097,264 B2
(45) Date of Patent: *Sep. 24, 2024

(54) METHODS AND COMPOSITIONS FOR THERANOSTIC NANOPARTICLES

(71) Applicants: University of Central Florida Research Foundation, Inc., Orlando, FL (US); Sanford Burnham Prebys Medical Discovery Institute at Lake Nona, Orlando, FL (US); Memorial Sloan Kettering Cancer Center, New York, NY (US)

(72) Inventors: Annette Khaled, Orlando, FL (US); Jesus Manuel Perez Figueroa, Los Angeles, CA (US); Santimukul Santra, Pittsburg, KS (US); Charalambos Kaittanis, Cambridge, MA (US); Oscar Santiesteban, El Segundo, CA (US); Jan Grimm, Larchmont, NY (US); Hampton Sessions, Orlando, FL (US)

(73) Assignees: University of Central Florida Research Foundation, Inc., et al., Orlando, FL (US); Sanford Burnham Prebys Medical Discovery Institute at Lake Nona, Orlando, FL (US); , Memorial Sloan Kettering Cancer Center, New York, NY (US)

( * ) Notice: Subject to any disclaimer, the term of this patent is extended or adjusted under 35 U.S.C. 154(b) by 361 days.

This patent is subject to a terminal disclaimer.

(21) Appl. No.: 17/228,286

(22) Filed: Apr. 12, 2021

(65) Prior Publication Data
US 2021/0228733 A1    Jul. 29, 2021

Related U.S. Application Data

(63) Continuation of application No. 15/570,218, filed as application No. PCT/US2016/029804 on Apr. 28, 2016, now Pat. No. 10,973,925.

(60) Provisional application No. 62/153,912, filed on Apr. 28, 2015.

(51) Int. Cl.
| A61K 45/06 | (2006.01) |
| A61K 38/08 | (2019.01) |
| A61K 38/10 | (2006.01) |
| A61K 47/68 | (2017.01) |
| A61K 47/69 | (2017.01) |
| A61K 51/10 | (2006.01) |
| A61K 51/12 | (2006.01) |

(52) U.S. Cl.
CPC .......... *A61K 47/6869* (2017.08); *A61K 38/08* (2013.01); *A61K 38/10* (2013.01); *A61K 45/06* (2013.01); *A61K 47/6935* (2017.08); *A61K 51/1072* (2013.01); *A61K 51/1244* (2013.01)

(58) Field of Classification Search
CPC ................ A61K 47/00; A61K 47/6869; A61K 47/6935; A61K 38/00; A61K 38/08; A61K 38/10; A61K 45/00; A61K 45/06; A61K 51/00; A61K 51/1072; A61K 51/1244; A61P 35/00
USPC ............... 424/1.11, 1.29, 1.33, 1.65, 9.1, 9.4
See application file for complete search history.

(56) References Cited

U.S. PATENT DOCUMENTS

| 10,973,925 | B2 * | 4/2021 | Khaled | ............... A61K 47/6869 |
| 11,129,868 | B2 * | 9/2021 | Khaled | .................. A61K 38/08 |
| 2011/0286919 | A1 | 11/2011 | Joshi et al. | |
| 2014/0178300 | A1 | 6/2014 | Pomper et al. | |
| 2014/0248210 | A1 | 9/2014 | Bradbury et al. | |
| 2014/0255299 | A1 | 9/2014 | Khaled et al. | |
| 2015/0004103 | A1 | 1/2015 | Borbely et al. | |
| 2015/0104387 | A1 | 4/2015 | Pomper et al. | |
| 2016/0128987 | A1 | 5/2016 | O'Neil | |

OTHER PUBLICATIONS

Santra et al., Langmuir, 226(8) pp. 5364-5373 (Year: 2010).*
Barrett, J.A et al. First-in-man evaluation of 2 high-affinity PSMA-avid small molecules for imaging prostate cancer. Journal of nuclear medicine: official publication, Society of Nuclear Medicine 54, 380387 (2013).
Baskin, J.M. et al. Copper-free click chemistry for dynamic in vivo imaging. Proceedings of the National Academy of Sciences of the United States of America 104, 16793-16797 (2007).
Boohaker, R.J. et al. Rational Development of a Cytotoxic Peptide to Trigger Cell Death. Molecular pharmaceutics 9:7, 2080-2093 (2012).
Boohaker, R.J., Lee, M.W., Vishnubhotla, P., Perez, J.M. & Khaled, A.R. The use of therapeutic peptides to target and to kill cancer cells. Current medicinal chemistry 19, 3794-3804 (2012).
Bostwick, D.G., Pacelli, A., Blute, M., Roche, P. & Murphy, G.P. Prostate specific membrane antigen expression in prostatic intraepithelial neoplasia and adenocarcinoma: a study of 184 cases. Cancer 82, 2256-2261 (1998).
Cancer Facts and Figures 2009. American Cancer Society, 72 pages (2009).

(Continued)

*Primary Examiner* — D. L. Jones
(74) *Attorney, Agent, or Firm* — Meunier Carlin & Curfman LLC

(57) ABSTRACT

Provided herein is a nanoparticle for drug delivery, wherein the nanoparticle comprises a hyperbranched polyester (HBPE) nanoparticle having a hydrophobic interior, polyglutamate folate ligands conjugated to the nanoparticle, and one or more PET detectable isotopes. Also provided herein are methods of using thereof.

9 Claims, 26 Drawing Sheets

Specification includes a Sequence Listing.

(56) References Cited

OTHER PUBLICATIONS

Chang, S.S. et al. Five different anti-prostate-specific membrane antigen (PSMA) antibodies confirm PSMA expression in tumor-associated neovasculature. Cancer research 59, 3192-3198 (1999).
Chen, Y. et al. Radiohalogenated prostate-specific membrane antigen (PSMA)-based ureas as imaging agents for prostate cancer. J Med Chem 51, 7933-7943 (2008).
Chen, Y. et al. Synthesis and biological evaluation of low molecular weight fluorescent imaging agents for the prostate-specific membrane antigen. Bioconjugate chemistry 23, 2377-2385 (2012).
Cheng, J. et al. Formulation of functionalized PLGA-PEG nanoparticles for in vivo targeted drug delivery. Biomaterials 28, 869-876 (2007).
Desai, S.P., Bhatia, S.N., Toner, M. & Irimia, D. Mitochondrial localization and the persistent migration of epithelial cancer cells. Biophysical journal 104, 2077-2088 (2013).
Farokhzad, O.C. et al. Nanoparticle-aptamer bioconjugates: a new approach for targeting prostate cancer cells. Cancer research 64, 7668-7672 (2004).
Farokhzad, O.C. et al. Targeted nanoparticle-aptamer bioconjugates for cancer chemotherapy in vivo. Proceedings of the National Academy of Sciences of the United States of America 103, 6315-6320 (2006).
Freeman, L.M. et al. The role of (111) In Capromab Pendetide (Prosta-ScintR) immunoscintigraphy in the management of prostate cancer. Q J Nucl Med 46, 131-137 (2002).
Garg, P., Nemec, K.N., Khaled, A.R. & Tatulian, S.A. Transmembrane pore formation by the carboxyl terminus of Bax protein. Biochimica et biophysica acta 1828, 732-742 (2013).
Ghosh, A. & Heston, W.D. Tumor target prostate specific membrane antigen (PSMA) and its regulation in prostate cancer. J Cell Biochem 91, 528-539 (2004).
Haseman, M.K., Rosenthal, S.A. & Polascik, T.J. Capromab Pendetide imaging of prostate cancer. Cancer Biother Radiopharm 15, 131-140 (2000).
Hattori, Y. & Maitani, Y. Folate-linked nanoparticle-mediated suicide gene therapy in human prostate cancer and nasopharyngeal cancer with herpes simplex virus thymidine kinase. Cancer Gene Ther 12, 796-809 (2005).
Holland, J.P. et al. Measuring the pharmacodynamic effects of a novel Hsp90 inhibitor on HER2/neu expression in mice using Zr-DFO-trastuzumab. PLoS One 5, e8859 (2010).
Horoszewicz, J.S., Kawinski, E. & Murphy, G.P. Monoclonal antibodies to a new antigenic marker in epithelial prostatic cells and serum of prostatic cancer patients. Anticancer Res 7, 927-935 (1987).
Hrkach, J. et al. Preclinical development and clinical translation of a PSMA-targeted docetaxel nanoparticle with a differentiated pharmacological profile. Science translational medicine 4, 128ra139 (2012).
Israeli, R.S., Powell, C.T., Fair, W.R. & Heston, W.D. Molecular cloning of a complementary DNA encoding a prostate-specific membrane antigen. Cancer research 53, 227-230 (1993).
Josephson, L., Tung, C.H., Moore, A. & Weissleder, R. High-efficiency intracellular magnetic labeling with novel superparamagnetic-Tat peptide conjugates. Bioconjugate chemistry 10, 186-191 (1999).
Kaittanis, C., Santra, S. & Perez, J.M. Role of nanoparticle valency in the nondestructive magnetic-relaxation-mediated detection and magnetic isolation of cells in complex media. Journal of the American Chemical Society 131, 12780-12791 (2009).
Kiss, T. & Farkas, E. Metal-binding ability of desferrioxamine B. Journal of Inclusion Phenomena and Molecular Recognition in Chemistry 32, 385-403 (1998).
Leibowitz-Amit, R. & Joshua, A.M. Targeting the androgen receptor in the management of castration-resistant prostate cancer: rationale, progress, and future directions. Curr Oncol 19, S22-31 (2012).
Leibowitz-Amit, R. & Joshua, A.M. The changing landscape in metastatic castration-resistant prostate cancer. Current opinion in supportive and palliative care 7, 243-248 (2013).
Lopes, A.O., Davis, W.L., Rosenstraus, M.J., Uveges, A.J. & Gilman, S.C. Immunohistochemical and pharmacokinetic characterization of the site-specific immunoconjugate CYT-356 derived from antiprostate monoclonal antibody 7E11-C5. Cancer research 50, 6423-6429 (1990).
McDevitt, M.R. et al. An alpha-particle emitting antibody ([213Bi]J591) for radioimmunotherapy of prostate cancer. Cancer research 60, 6095-6100 (2000).
Meijs, W.E. et al. Zirconium-labeled monoclonal antibodies and their distribution in tumor-bearing nude mice. Journal of nuclear medicine: official publication, Society of Nuclear Medicine 38, 112-118 (1997).
Milowsky, M.I. et al. Vascular targeted therapy with anti-prostate-specific membrane antigen monoclonal antibody J591 in advanced solid tumors. J Clin Oncol 25, 540-547 (2007).
Morris, M.J. et al. Phase I evaluation of J591 as a vascular targeting agent in progressive solid tumors. Clinical cancer research: an official journal of the American Association for Cancer Research 13, 2707-2713 (2007).
Perez, J.M., Josephson, L. & Weissleder, R. Use of magnetic nanoparticles as nanosensors to probe for molecular interactions. Chembiochem: a European journal of chemical biology 5, 261-264 (2004).
Perez, J.M., Josephson, L., O'Loughlin, T., Hogemann, D. & Weissleder, R. Magnetic relaxation switches capable of sensing molecular interactions. Nature biotechnology 20, 816-820 (2002).
Perez, J.M., O'Loughin, T., Simeone, F.J., Weissleder, R. & Josephson, L. DNA-based magnetic nanoparticle assembly acts as a magnetic relaxation nanoswitch allowing screening of DNA-cleaving agents. Journal of the American Chemical Society 124, 2856-2857 (2002).
Perez, J.M., Simeone, F.J., Saeki, Y., Josephson, L. & Weissleder, R. Viral-induced self-assembly of magnetic nanoparticles allows the detection of viral particles in biological media. Journal of the American Chemical Society 125, 10192-10193 (2003).
Rafehi, H. et al. Clonogenic assay: adherent cells. Journal of visualized experiments: JoVE 49, 2573 (2011).
Ratts, R. et al. The cytosolic entry of diphtheria toxin catalytic domain requires a host cell cytosolic translocation factor complex. The Journal of cell biology 160, 1139-1150 (2003).
Ross, J.S. et al. Correlation of primary tumor prostate-specific membrane antigen expression with disease recurrence in prostate cancer. Clinical cancer research: an official journal of the American Association for Cancer Research 9, 6357-6362 (2003).
Ruggiero, A. et al. Targeting the Internal Epitope of Prostate-Specific Membrane Antigen with 89Zr-7E11 Immuno-PET. Journal of nuclear medicine: official publication, Society of Nuclear Medicine 52, 1608-1615 (2011).
Santra, S. & Perez, J.M. Selective N-Alkylation of beta-Alanine Facilitates the Synthesis of a Poly(amino acid)-Based Theranostic Nanoagent. Biomacromolecules 12:11, 3917-3927 (2011).
Santra, S., Kaittanis, C. & Perez, J.M. Aliphatic hyperbranched polyester: a new building block in the construction of multifunctional nanoparticles and nanocomposites. Langmuir 26, 5364-5373 (2009).
Santra, S., Kaittanis, C., Grimm, J. & Perez, J.M. Drug/dye-loaded, multifunctional iron oxide nanoparticles for combined targeted cancer therapy and dual optical/magnetic resonance imaging. Small 5, 1862-1868 (2009).
Santra, S., Kaittanis, C., Santiesteban, O.J. & Perez, J.M. Cell-specific, activatable, and theranostic prodrug for dual-targeted cancer imaging and therapy. Journal of the American Chemical Society 133, 16680-16688 (2011).
Scatena, C.D. et al. Imaging of bioluminescent LNCaP-luc-M6 tumors: a new animal model for the study of metastatic human prostate cancer. The Prostate 59, 292-303 (2004).
Schrecengost, R. & Knudsen, K.E. Molecular pathogenesis and progression of prostate cancer. Seminars in oncology 40, 244-258 (2013).
Silver, D.A., Pellicer, I., Fair, W.R., Heston, W.D. & Cordon-Cardo, C. Prostate-specific membrane antigen expression in normal and malignant human tissues. Clinical cancer research: an official journal of the American Association for Cancer Research 3, 81-85 (1997).

(56) References Cited

OTHER PUBLICATIONS

Smith-Jones, P.M. et al. Radiolabeled monoclonal antibodies specific to the extracellular domain of prostate-specific membrane antigen: preclinical studies in nude mice bearing LNCaP human prostate tumor. Journal of nuclear medicine: official publication, Society of Nuclear Medicine 44, 610-617 (2003).
Soriano Del Amo, D. et al. Biocompatible copper(I) catalysts for in vivo imaging of glycans. Journal of the American Chemical Society 132, 16893-16899 (2010).
Stern, S.T., Adiseshaiah, P.P. & Crist, R.M. Autophagy and lysosomal dysfunction as emerging mechanisms of nanomaterial toxicity. Particle and fibre toxicology 9, 20, 17 pages (2012).
Tatulian, S.A., Garg, P., Nemec, K.N., Chen, B. & Khaled, A.R. Molecular basis for membrane pore formation by Bax protein carboxyl terminus. Biochemistry 51, 9406-9419 (2012).
Tolaney, S.M., Najita, J., Winer, E.P. & Burstein, H.J. Lymphopenia associated with adjuvant anthracycline/ taxane regimens. Clinical breast cancer 8, 352-356 (2008).
Ulmert, D. et al. Imaging androgen receptor signaling with a radiotracer targeting free prostate-specific antigen. Cancer discovery 2, 320-327 (2012).
Van der Meel, R., Vehmeijer, L.J., Kok, R.J., Storm, G. & van Gaal, E.V. Ligand-targeted particulate nanomedicines undergoing clinical evaluation: current status. Advanced drug delivery reviews 65, 1284-1298 (2013).
Verel, I. et al. 89Zr immuno-PET: comprehensive procedures for the production of 89Zr-labeled monoclonal antibodies. Journal of nuclear medicine: official publication, Society of Nuclear Medicine 44, 1271-1281 (2003).
Wesche, J. et al. FGF-1 and FGF-2 require the cytosolic chaperone Hsp90 for translocation into the cytosol and the cell nucleus. The Journal of biological chemistry 281, 11405-11412 (2006).
Wright, G.L., Jr. et al. Upregulation of prostate-specific membrane antigen after androgen-deprivation therapy. Urology 48, 326-334 (1996).
Xu, L., Pirollo, K.F. & Chang, E.H. Tumor-targeted p53-gene therapy enhances the efficacy of conventional chemo/radiotherapy. J Control Release 74, 115-128 (2001).
Yao, V. & Bacich, D.J. Prostate specific membrane antigen (PSMA) expression gives prostate cancer cells a growth advantage in a physiologically relevant folate environment in vitro. The Prostate 66, 867-875 (2006).
Yao, V., Berkman, C.E., Choi, J.K., O'Keefe, D.S. & Bacich, D.J. Expression of prostate-specific membrane antigen (PSMA), increases cell folate uptake and proliferation and suggests a novel role for PSMA in the uptake of the non-polyglutamated folate, folic acid. The Prostate 70, 305-316 (2010).
Zhao, J. et al. Mitochondrial dynamics regulates migration and invasion of breast cancer cells. Oncogene 32, 4814-4824 (2013).
International Search Report and Written Opinion issued for International Application No. PCT/US2016/029804, dated Aug. 25, 2016.
International Preliminary Report on Patentability issued for International Application No. PCT/US2016/029804, dated Nov. 9, 2017.
Zhang et al., "Folate-decorated poly(lactide-co-glycolide)-vitamin E TPGS nanoparticles for targeted drug delivery", Biomaterials, 28, pp. 1889-1899, 2007.
Office Action issued in Canadian Application No. 3022354, mailed Jul. 26, 2023.
Lee et al., "The CT20 peptide causes detachment and death of metastatic breast cancer cells by promoting mitochondrial aggregation and cytoskeletal disruption", *Cell Death Dis.*, 5 (5) p. e1249, May 22, 2014 (May 22, 2014).

* cited by examiner

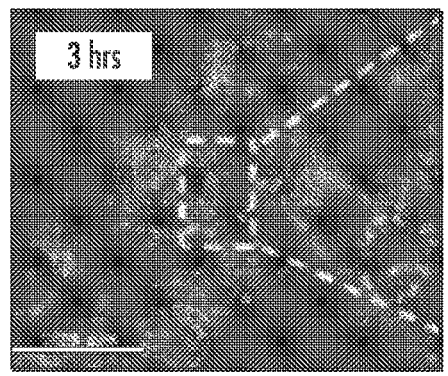
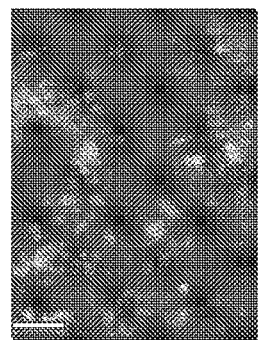
Rho-CT20p/MITOTRACKER GREEN
FIG. 19A
LC3-GFP
FIG. 19B
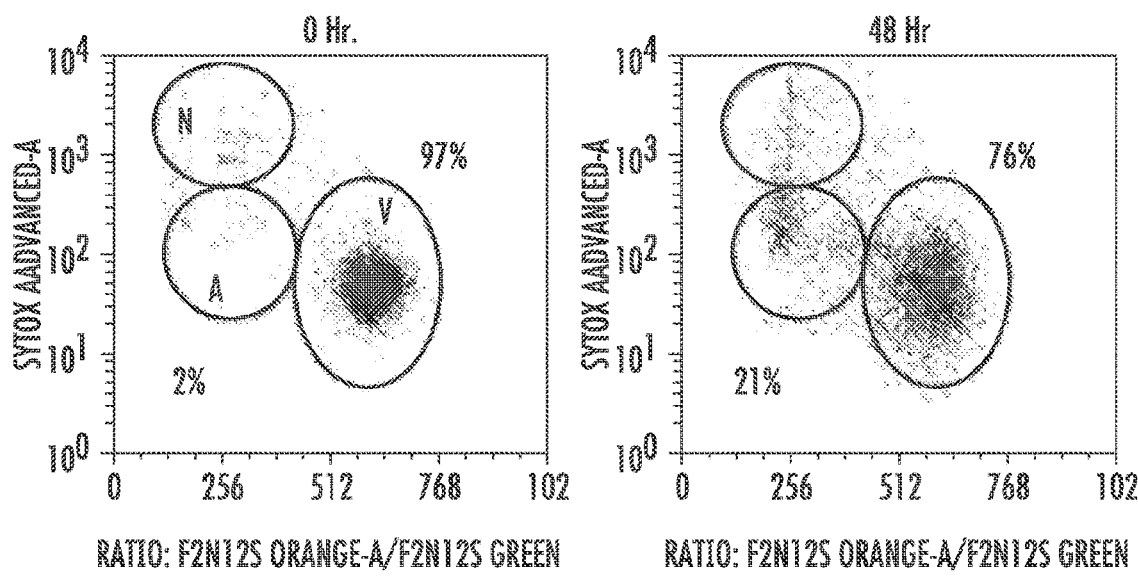
FIG. 19C

METHODS AND COMPOSITIONS FOR THERANOSTIC NANOPARTICLES

CROSS REFERENCE TO RELATED APPLICATIONS

This application claims the benefit of priority to U.S. Provisional Application No. 62/153,912, filed Apr. 28, 2015, which is incorporated by reference herein in its entirety.

STATEMENT REGARDING FEDERALLY SPONSORED RESEARCH

This invention was made with government support under grant numbers K01CA 101781 and GM083324 awarded by the National Institutes of Health. The government has certain rights in the invention.

FIELD

The subject matter disclosed herein is in the field of nanoparticles, including methods of identifying and monitoring tumor cells by providing a nanoparticle functionalized with one or more ligands and one or more imaging compounds.

BACKGROUND

The imaging, diagnosis, and successful treatment of prostate cancer (PCa) continue to be a challenging problem and it is estimated that 1 out of 6 men will be diagnosed with the disease during their lifetime. Early detection using existing techniques is difficult due to the (1) relatively small size of the prostate gland. (2) low metabolic rate of PCa and (3) close proximity of the prostate to the bladder, which limits the use of traditional PET imaging using small molecule ($^{18}$F-FDG) radionucleotides that accumulate in the bladder before excretion. Meanwhile, current treatment options for PCa, such as surgery, systemic chemotherapy and radiation therapy are often ineffective and usually result in severe side effects for the patients. Therefore, development of more effective agents against advanced PCa that allow for simultaneous therapy and monitoring are urgently needed. Particularly needed are targeted molecular theranostic (dual therapy and diagnostic) regimes that allow delivery of a new generation of imaging and therapeutic agents in high concentrations to PCa.

Death due to prostate cancer (PCa) generally results when patients develop metastatic castration-resistant prostate cancer (mCRPC). While current treatments for mCRPC improve survival, the disease still remains incurable, and treatments result in severe side effects, such as impotence and incontinence. Current methods to detect PCa and monitor treatment out comes are typically invasive, indicating a need for new imaging agents that use sensitive molecular imaging technologies such as PET (positron emission tomography).

Thus, there is a need for compositions and methods for the delivery and monitoring of therapeutic peptides to areas of disease. These needs and other needs are satisfied by the present invention

SUMMARY

In accordance with the purposes of the disclosed materials, compounds, compositions, articles, devices, and methods, as embodied and broadly described herein, the disclosed subject matter relates to compositions and methods of making and using the compositions. In other aspects, the disclosed subject matter relates to nanoparticles comprising a polymeric nanoparticle conjugated with targeting ligand that is a substrate for a solid tumor-specific cell protein, wherein the nanoparticle further comprises an imaging compound and has a therapeutic agent encapsulated in the hydrophobic interior of the nanoparticle. A cancer therapeutic composition comprising the nanoparticle are also disclosed.

In a further aspect, disclosed herein are methods of identifying a solid tumor cell target comprising contacting a cell with an effective amount of a composition comprising the nanoparticles disclosed herein.

In a still further aspect, disclosed herein is a method for treating prostate cancer, comprising administering to a subject diagnosed with prostate cancer an effective amount of the nanoparticle composition.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying Figure, which is incorporated in and constitutes a part of this specification, illustrates several aspects and together with the description serves to explain the principles of the invention.

FIG. 13 depicts the general synthetic scheme toward Scaffold 4 analogs.

FIG. 18A shows that rhodanine-labeled CT20p (red) co-localizes with mitochondria (mitotracker green) FIG. 18B shows that mitochondrial membranes hyperpolarize and fuse (JC-1 probe) FIG. 18C shows that mitochondria (red) fail to redistribute to cell extensions, causing reduced F-actin (green) polymerization (nucleus, DAPI, blue). FIG. 18D shows that the initial viability of cells was determined by measuring membrane permeability (Sytox) and membrane asymmetry (violet ratiometric dye). Gates are N, necrotic; V, viable: A, apoptotic. Percentages are V (black) and N+A (red). FIG. 18E is a graph showing that by 6 hours, cells detach from the substrate (fibronectin). Such cell detachment was measured using a crystal violet adhesion assay. FIG. 18F shows that prior to detecting cell detachment, membrane levels of β1 integrin decreased as detected with an anti-β1 antibody. FIGS. 18G-18I show that post-cell detachment events include caspase activation (FIG. 18G: shows detection of caspase3/7 activity by colorimetric assay), autophagy (FIG. 18H: shows the formation of autophagosomes detected by GFP-LC3), and increased ROS production (FIG. 18I: shows mitochondrial superoxide detected using Mitosox). FIG. 18J shows that apoptosis/anoikis was detected between 24-48 hours as described in FIG. 5D. *p<0.5

FIG. 19A-19C show that normal cells were affected by CT20p. FIG. 19A shows that rhodamine-labeled CT20p (red) did not co-localize with mitochondria (green) or cause autophagy (no autophagosomes formed). FIG. 19B shows results after 24 hours, LC3-GFP. FIG. 19C shows that minimal cell death was detected.

FIG. 21G shows the fluorescence microscopy image of PSMA(+) PCa cells treated with Folate HBPE(CT20p) NPs and FIG. 21H shows the corresponding DiI fluorescence. FIG. 21I shows the results of the sytox analysis using macrophages incubated with CT20p (left), doxorubicin (middle), and Folate-s-s-Doxo (right). V, viable; N, necrotic, A, apoptotic.

DETAILED DESCRIPTION

Figure 1:
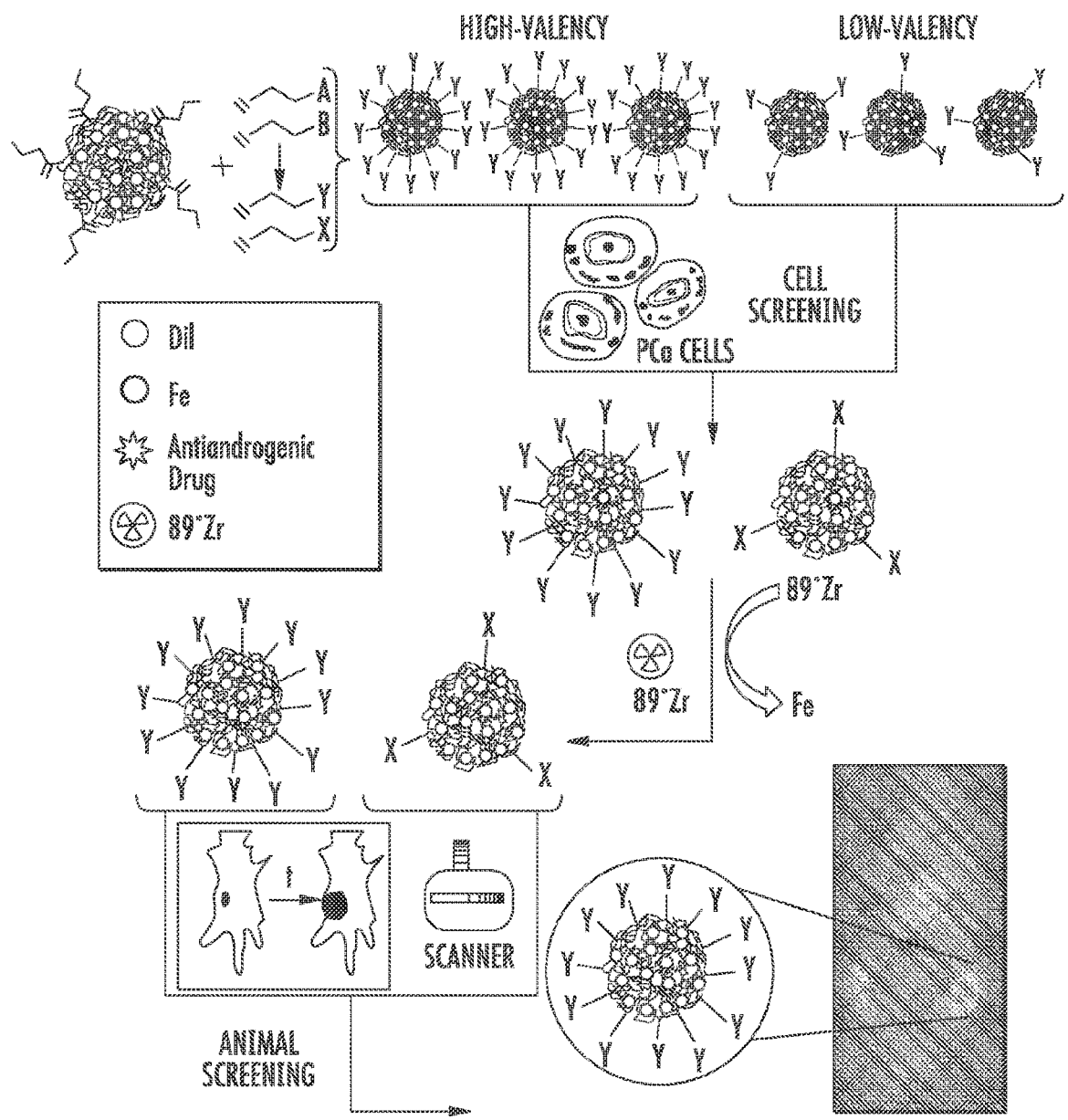
FIG. 1 is a schematic representation of a method for the development and screening of a multivalent theranostic nanoparticle library for PSMA targeting.

The disclosed subject matter can be understood more readily by reference to the following detailed description, the Figures, and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is understood that the disclosed methods and systems are not limited to the particular methodology, protocols, and systems described as these may vary. It is also to be understood that the terminology used herein is for the purpose of describing particular embodiments only, and is not intended to limit the scope of the present invention which will be limited only by the appended claims.

Definitions

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the amino acid abbreviations are conventional one letter codes for the amino acids and are expressed as follows: A, alanine; B, asparagine or aspartic acid: C, cysteine; D aspartic acid; E, glutamate, glutamic acid; F, phenylalanine; G, glycine; H histidine; I isoleucine: K, lysine; L, leucine; M, methionine; N, asparagine; P, proline; Q, glutamine; R, arginine; S, serine; T, threonine; V, valine; W, tryptophan; Y, tyrosine: Z, glutamine or glutamic acid.

"Peptide" as used herein refers to any peptide, oligopeptide, polypeptide, gene product, expression product, or protein. For example, a peptide can be a fragment of a full-length protein, such as, for example, the CT20 peptide. A peptide is comprised of consecutive amino acids. The term "peptide" encompasses naturally occurring or synthetic molecules.

In general, the biological activity or biological action of a peptide refers to any function exhibited or performed by the peptide that is ascribed to the naturally occurring form of the peptide as measured or observed in vivo (i.e., in the natural physiological environment of the protein) or in vitro (i.e., under laboratory conditions). For example, a biological activity of the CT20 peptide is the cytotoxic activity of the CT20 peptide.

The term "enzyme" as used herein refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as those disclosed herein.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2 S. and are present in such ratio regardless of whether additional components are contained in the compound A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

As used herein, "a CT20 peptide" or "CT20" may refer to one peptide or may refer one or more peptides (i.e., a C-terminal Bx peptide), such as molar concentrations of the peptide, as would be found in a composition. In an aspect, a CT20 peptide can comprise SEQ ID NO:1, SEQ ID NO:2, SEQ ID NO:3. SEQ ID NO:4, SEQ ID NO:5, or SEQ ID NO:6. In an aspect, a CT20 peptide can comprise a combination of two or more of SEQ ID NOs 1-6. Those skilled in the art understand where an individual peptide is intended and where a molar, or smaller or larger amount, of many of the same peptide are intended.

As used herein, "noncancerous cells" and "noncancerous tissue" can refer to cells or tissue, respectively, that are normal or cells or tissue that do not exhibit any metabolic or physiological characteristics associated with cancer. For example, noncancerous cells and noncancerous tissues are healthy and normal cells and tissues, respectively.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

Therapeutic agents can include antimicrobial agents, such as antibiotics or antimycotic compounds, including but not limited to, active agents such as antifungal agents, antibacterial agents, anti-viral agents and antiparasitic agents, and metals. An antimicrobial agent can comprise a substance, compound or molecule, which kills or inhibits the growth of microorganisms such as bacteria, fungi, or protozoans. Antimicrobial agents may either kill microbes (microbiocidal) or prevent the growth of microbes (microbiostatic). Disinfectants are antimicrobial substances used on non-living objects or outside the body. Antimicrobial agents include those obtained from natural sources, such as Beta-lactam antibiotics (such as penicillins, cephalosporins), and protein synthesis inhibitors (such as aminoglycosides, macrolides, tetracyclines, chloramphenicol, polypeptides), and those from synthetic sources such as sulphonamides, cotrimoxazole, quinolones, anti-fungals, anti-cancer drugs, anti-malarials, anti-tuberculosis drugs, anti-leprotics, and anti-protozoals.

Examples of antimicrobial agents that can be used herein include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ainpicillin, amphotericin B, ketoconazole, fluconazole, pyrimethaniine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms. As used herein, the term metal includes all metal salts or metal compounds, including, but not limited to, metal chlorides, metal phosphates, metal sulfates, metal iodides or metal bromides. The active form of some metal salts is the ionic form. Other antimicrobial agents include, but are not limited to, polyene antifungals, Amphotericin B, Candicidin, Filipin, Hamycin, Natamycin, Nystatin, Rimocidin, Imidazoles, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Triazoles, Albaconazole, Fluconazole, Isavuconazole, Itraconazole, Posaconazole, Ravuconazole, Terconazole, Voriconazole. Thiazoles, Abafungin, Allylamines, Amorolfin, Butenafine Naftifine, Terbinafine, Echinocandins, Anidulafungin, Caspofungin, Micafungin The terms "treating", "treatment", "therapy", and "therapeutic treatment" as used herein refer to curative therapy, prophylactic therapy, or preventative therapy. As used herein, the terms refers to the medical management of a subject or a patient with the intent to cure, ameliorate, stabilize, or prevent a disease, pathological condition, or disorder, such as, for example, cancer or a tumor. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development: or (iii) relieving the disease, i.e., causing regression of the disease. In an aspect, the disease, pathological condition, or disorder is cancer, such as, for example, breast cancer, lung cancer, colorectal, liver cancer, or pancreatic cancer. In an aspect, cancer can be any cancer known to the art.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells.

As used herein, the term "diagnosed" means having been subjected to a physical examination by a person of skill, for example, a physician or a researcher, and found to have a condition that can be diagnosed or treated by compositions or methods disclosed herein. For example, "diagnosed with cancer" means having been subjected to a physical examination by a person of skill, for example, a physician or a researcher, and found to have a condition that can be diagnosed or treated by a compound or composition that alleviates or ameliorates cancer and/or aberrant cell growth.

As used herein, the terms "administering" and "administration" refer to any method of providing a peptide (such as a CT20 peptide), or a composition (such as a composition comprising a CT20 peptide), or pharmaceutical preparation (such as a preparation comprising a CT20 peptide or a composition comprising a CT20 peptide) to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically: that is, administered to treat an existing disease or condition. In further various aspects, a preparation can be administered prophylactically: that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly, i.e., by interacting with another molecule, co-factor, factor, or protein on which the activity of the target is dependent.

As used herein, the term "determining" can refer to measuring or ascertaining a quantity or an amount or a change in expression and/or activity level, e.g., of a nucleotide or transcript or polypeptide (e.g., CCT or a CCT subunit). For example, determining the amount of a disclosed transcript or polypeptide in a sample as used herein can refer to the steps that the skilled person would take to measure or ascertain some quantifiable value of the transcript or polypeptide in the sample. The art is familiar with the ways to measure an amount of the disclosed nucleotides, transcripts, polypeptides, etc.

In an aspect, "determining" as used herein can refer to measuring or ascertaining the level of cell death or cell survival, for example, following administration of a CT20 peptide or a composition comprising an effective amount of a CT20 peptide. Methods of measuring or ascertaining cell survival and cell death are known to the art and include, but are not limited to, histochemical staining (e.g., TUNEL), cell proliferation assay, cell death assays, morphological examination, etc. In an aspect, the size of a tumor can be measured non-invasively through, for example, ultrasound or imaging.

As used herein, the term "level" refers to the amount of a target molecule in a sample, e.g., a sample from a subject. The amount of the molecule can be determined by any method known in the art and will depend in part on the nature of the molecule (i.e., gene, mRNA, cDNA, protein, enzyme, etc.). The art is familiar with quantification methods for nucleotides (e.g., genes, cDNA, mRNA, etc.) as well as proteins, polypeptides, enzymes, etc. It is understood that the amount or level of a molecule in a sample need not be determined in absolute terms, but can be determined in relative terms (e.g., when compare to a control or a sham or an untreated sample).

As used herein, the terms "effective amount" and "amount effective" refer to an amount that is sufficient to achieve the desired result or to have an effect on an undesired condition. For example, in an aspect, an effective amount of a CT20 peptide is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient, the time of administration, the route of administration, the rate of excretion of the specific compound employed; the duration of the treatment; drugs used in combination or coincidental with the specific compound employed and like factors well known in the medical arts.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

As used herein, "$IC_{50}$," is intended to refer to the concentration or dose of a substance (e.g., a CT20 peptide or a disclosed composition comprising a CT20 peptide) that is required for 50% inhibition or diminution of a biological process, or component of a process, including a protein, subunit, organelle, ribonucleoprotein, etc. $IC_{50}$ also refers to the concentration or dose of a substance that is required for 50% inhibition or diminution in vivo, as further defined elsewhere herein. Alternatively. $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured cancer cells or in an ex vivo organ culture system with isolated cancer cells (e.g., breast cancer cells, pancreatic cancer cells, liver cancer cells, lung cancer cells, colorectal cancer cells, etc.). Alternatively, the response can be measured in vivo using an appropriate research model such as rodent, including mice and rats. The mouse or rat can be an inbred strain with phenotypic characteristics of interest such as, for example, cancer and/or aberrant cell growth. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and can be divided into different subtypes based on their biological characteristics. Cancer includes, but is not limited to, melanoma, leukemia, astrocytoma, glioblastoma, lymphoma, glioma, Hodgkin's lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

As used herein, the term "sensitizing" refers to an increased sensitivity of a cell or a subject to a treatment, such as a therapeutic treatment. The term "sensitizing" also refers to a reduction or decrease in the resistance of a cancer cell or a subject with cancer in responding to a therapeutic treatment. An increased sensitivity or a reduced sensitivity to a therapeutic treatment is measured according to a known method in the art for the particular treatment and methods including, but not limited to, cell proliferation assays and cell death assays. The sensitivity or resistance may also be measured in a subject by measuring the tumor size reduction over a period of time, such as, for example, every 1 to 3 to 6 month for a human subject and every 2 to 4 to 6 weeks for non-human subject (e.g., mouse or rat). The sensitivity of a cell or a subject to treatment can be measured or determined by comparing the sensitivity of a cell or a subject following administration of a CT20 peptide or a composition comprising an effective amount of a CT20 peptide to the sensitivity of a cell or subject that has not been administered a CT20 peptide or a composition comprising an effective amount of a CT20 peptide.

As used herein, the term "anti-cancer" or "anti-neoplastic" drug refers to one or more drugs that can be used in conjunction with a CT20 peptide or a composition comprising an effective amount of a CT20 peptide to treat cancer and/or aberrant cell growth. Examples of anti-cancer drugs or anti-neoplastic drugs include, but are not limited to, the following: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a, Interferon Gamma-I b; Iproplatin; Irinotecan Hydrochloride; Lanreotide Acetate; Letrozole; Leuprolide Acetate; Liarozole Hydrochloride. Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper, Mitotane; Mitoxantrone Hydrochloride; Mycophenolic Acid; Nocodazole, Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1.25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D, antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylsperimine; bisnafide; bistratene A; bizelesin; breflate; bropirimine; budotitane; buthionine sulfoximine; calcipotriol; calphostin C; camptothecin derivatives, canarypox IL-2; capecitabine; carboxamide-amino-triazole; carboxy amidotriazole; CaRest M3; CARN 700; cartilage derived inhibitor, carzelesin; casein kinase inhibitors (ICOS); castanospermine; cecropin B; cetrorelix; chlorins; chloroquinoxaline sulfonamide; cicaprost; cis-porphyrin; cladribine, clomifene analogues; clotrimazole; collismycin A; collismycin B; combretastatin A4; combretastatin analogue, conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab, decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride;

estramustine analogue; estrogen agonists; estrogen antagonists; etanidazole; etoposide phosphate; exemestane; fadrozole; fazarabine; fenretinide; filgrastim, fmasteride; flavopiridol; flezelastine; fluasterone; fludarabine; fluorodaunorunicin hydrochloride; forfenimex; formestane; fostriecin; fotemustine; gadolinium texaphyrin, gallium nitrate; galocitabine; ganirelix; gelatinase inhibitors; gemcitabine, glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine, losoxantrone; lovastatin, loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A +myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide, nisamycin; nitric oxide modulators; nitroxide antioxidant; nitrullyn; O6-benzylguanine; octreotide; okicenone, oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors, purpurins, pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCN U; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongislatin 1; squalamine; stem cell inhibitor; stem-cell division inhibitors; stipiamide; stromelysin inhibitors, sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan, thyroid stimulating hormone, tin ethyl etiopurpurin; tirapazamine; titanocene dichloride; topotecan; topsentin; toremifene; totipotent stem cell factor; translation inhibitors, tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B, vector system, erythrocyte gene therapy; velaresol; veramine; verdins, verteporfin; vinorelbine; vinxaltine, vitaxin, vorozole; zanoterone; zeniplatin; zilascorb; zinostatin stimalamer.

As used herein, radiosensitizers make a cancer cell more likely to be damaged. Radiosensitizers enhance the sensitivity of cancer cells and/or a tumor to ionizing radiation, thereby increasing the efficacy of radiotherapy. Examples of radiosensitizers include gemcitabine, 5-fluorouracil, pentoxifylline, and vinorelbine.

The majority of chemotherapeutic drugs can be divided in to: alkylating agents (e.g., cisplatin, carboplatin, oxaliplatin, mechloethamine, cyclophosphamide, chlorambucil), anti-metabolites (e.g., azathioprine, mercaptopurine), anthracyclines, plant alkaloids and terpenoids (e.g., vinca alkaloids (e.g., vincristine, vinblastine, vinorelbine, vindesine, and podophyllotoxin) and taxanes (e.g., paclitaxel and docetaxel), topoisomerase inhibitors (e.g., irinotecan, topotecan, amsacrine, etoposide, etoposide phosphate, and teniposide), monoclonal antibodies (e.g., trastuzumab, cetuximab, rituximab, bevacizumab), other antitumour agents (e.g., dactinomycin), and hormonal therapy (e.g., steroids such as dexamethasone, finasteride, aromatase inhibitors, and gonadotropin-releasing hormone agonists).

Disclosed are the components to be used to prepare a composition disclosed herein as well as the compositions themselves to be used within the methods disclosed herein. These and other materials are disclosed herein, and it is understood that when combinations, subsets, interactions, groups, etc, of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations. A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

All patents, patent applications, and other scientific or technical writings referred to anywhere herein are incorporated by reference in their entirety. The disclosed subject matter can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

Nanoparticles

A nanoparticle-based therapeutics is ideal as a single agent delivers a drug and imaging agent to the prostate tumor via recognition of surface receptor markers highly expressed on the tumor cells. The prostate specific membrane antigen (PSMA) is a type II transmembrane glycoprotein with glutamate carboxylase and folate hydrolase activity, highly expressed in PCa. PSMA expression usually increases with PCa progression and metastasis, providing an excellent target for PCa detection and treatment, especially for the more aggressive forms of the disease. In addition, high levels of PSMA have been found on the endothelial cells of the tumor-associated neovasculature of other solid tumors, including breast, lung, colon and pancreas, but not on the normal vasculature.

PSMA exhibits an enzymatic function as a folate hydrolase, hydrolyzing extracellular polyglutamated folate to mono-glutamic folic acid that can then be utilized by cells. It has been proposed that upregulation of PSMA can provide PCa cells with a growth advantage in a low folate tumor micro-environment and implicate PSMA in the metabolism of polyglutamated folates and the subsequent uptake of folates. Folic acid, a high affinity ligand for the folate receptor (FR), retains its receptor binding and endocytosis properties when covalently linked to a wide variety of molecules and nanoparticles. Liposome conjugated folate ligands have been used for the delivery of drugs to FR-bearing tumors. However, the use of folate and polyglutamated folate ligands to deliver chemotherapeutics or nanoparticles to PSMA-bearing PCa tissues and the neovasculature of many other tumors had not been studied in detail. The experiments disclosed herein took advantage of PSMA's binding affinity towards polyglutamated folate molecules and developed a library of nanoparticles conjugated with polyglutamated folate derivatives to target PSMA. The experiments developed multifunctional, multimodal and multivalent nanoparticle systems that are used to simultaneously deliver imaging agents and potent anti-androgenic drugs specifically to PCa via PSMA targeting. The specific targeting of these nanoagents to PCa reduced the drugs' systemic exposure, and its associated imaging function facilitated in vivo imaging to assess drug delivery to the tumor.

PSMA has already been used to target imaging and therapeutic agents to PCa. Anti-PSMA monoclonal antibody (mAb) has been developed to image and deliver chemotherapeutics directly to PCa with suboptimal results and low sensitivity to detect viable tumors. However, high manufacturing costs limit their widespread application for the targeting and treatment of tumors. Aptamers have also been investigated as an alternative to antibodies. PSMA-binding aptamers have been identified and conjugated to polymeric nanoparticles encapsulating the anticancer drug docetaxel for the targeted treatment of LNCaP xenografts in nude mice. However, these studies have not been reproducible due to stability issues with the aptamers in serum. Even though, antibodies and aptamers have been conjugated to polymeric nanoparticles to target PSMA in the past, and some of these nanoparticle formulations are currently in Phase I clinical trials, these nanoparticles do not possess imaging capabilities. Furthermore, the effect of ligand multivalency on these nanoparticle formulations and the effect on targeting ability have not been studied. The ligand's density on the nanoparticle's surface plays a key role in target recognition, specificity and sensitivity in in vitro diagnostic assays and also plays a role in vivo. Disclosed herein are compositions and methods that provide insight on the role of multivalency in the in vivo delivery of therapeutics and imaging agents. In addition, the compositions and methods used herein are significantly different from the ones previously investigated since small molecules are utilized, not PSMA targeting aptamers or anti-PSMA monoclonal antibodies which are costly and difficult to make. Finally, as PSMA is also expressed in the neovasculature of other solid tumors, the compositions and methods disclosed herein are used on other types of cancers besides PCa by targeting PSMA expression on the tumor neovasculature and not the tumor itself.

The current disclosure comprises design and fabrication of polymeric nanoparticles capable of displaying targeting ligands (polyglutamated folates) at high and low density. A rationally-designed compound library of ligands containing folic and glutamic acid functionalities was synthesized and conjugated to the nanoparticles at high and low density with the goal of identifying a particular ligand-nanoparticle conjugate that specifically binds to PSMA in PCa. These nanoparticles conjugates were used to study the effect of multivalency on PSMA targeting using polyglutamated folate ligands. Next, members of the nanoparticle library with the most specific binding to PSMA in cell culture were used in animal studies for the delivery of potent antiandrogenic drugs and a PET tracer ($^{89}$Zr) to PCa via PSMA targeting (FIG. 1).

Thus, disclosed herein are nanoparticles. In an aspect, the nanoparticles are hyberbranched polyester polymeric nanoparticles (HBPE-NPs or just HBPE). In an aspect, the nanoparticles are polymeric nanoparticles. In an aspect, the nanoparticles can comprise a functionalizing group that can be used to attach targeting ligands, therapeutics, or imaging agents. Examples of suitable functionalizing groups that can be present on the disclosed nanoparticles are azides, amines, alcohols, esters, and the like. In a specific aspect, disclosed are HBPE nanoparticles with these functionalizing groups, in particular azides. In an aspect, the nanoparticles can comprise a targeting moiety. In an aspect, the nanoparticles are conjugated with one or more targeting ligands. In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, the nanoparticles comprise an imaging compound. In aspect, the imaging compound is a PET detectable compound. In an aspect, the PET detectable compound is $^{99}$Zr. In an aspect, the PET detectable compound is CU or other PET detectable compounds.

In another aspect, the nanoparticles comprise one or more therapeutic agents that are encapsulated in the hydrophobic interior of the nanoparticle. In an aspect, the one or more therapeutic agents are CT20p. In another aspect, the one or more therapeutic agents are mutant CT20 peptides. A CT20 peptide is a C-terminal Bax peptide. Bax is a 21 kD protein of 192 amino acids, comprised of nine alpha helices (Suzuki et al., 2000). Under non-apoptotic conditions, Bax predominantly resides in the cytosol, with a small percentage of the protein localized to the mitochondria (Boohaker et al., 2011: Kaufmann et al. 2003; Putcha et al., 1999). Bax peptides, Bax proteins, and Bax genes are known to those skilled in the art. In an aspect, the one or more therapeutic agents are metotoxic peptides. In an aspect, the one or more therapeutic agents are anti-metastatic agents. In an aspect, the one or more therapeutic agents are anti-androgenic agents. In an aspect, the one or more therapeutic agents are anti-neoplastic agents.

In an aspect, the nanoparticles comprise a chelating ligand such as desferrioxamine (DFO). In an aspect, the nanoparticles are polyglutamated folate-HBPE-DFO[CT20p]-nanoparticles. In an aspect, the nanoparticle comprises PEG.

Cancer Therapeutic Compositions
Compositions for Dual Targeting and/or Imaging

Disclosed herein are cancer therapeutic compositions. In an aspect, the cancer therapeutic compositions comprise at least one nanoparticle. In an aspect, the nanoparticles are hyberbranched polyester polymeric nanoparticles (HBPE-NPs). In an aspect, the nanoparticles are polymeric nanoparticles. In an aspect, the nanoparticles can comprise a targeting moiety. In an aspect, the nanoparticles are conjugated with a targeting ligand. In an aspect, the targeting ligand is a folate compound. In an aspect, the targeting ligand is a glutamate compound. In a specific aspect, the targeting ligand can be an agent that binds to the folate receptor or the glutamate receptor. In a specific aspect, the targeting ligand can be an antibody specific for these reseptors, which can be conjugated to the nanoparticle with NHS/EDS or click chemistry (azide functional group bonding to a dipolarophile like an alkene or alkyne). In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, the nanoparticles comprise one or more imaging compounds. In aspect, the imaging compound is a PET detectable compound. In an aspect, the PET detectable compound is $^{89}$Zr. In an aspect, the PET detectable compound is CU or other PET detectable compounds. In an aspect, the nanoparticles comprise a chelating ligand such as desferrioxamine (DFO). In an aspect, the nanoparticles are polyglutamated folate-HBPE-DFO[CT20p]-nanoparticles. In an aspect, the nanoparticle comprises PEG. Further examples of chelating ligands that can be used include, but are not limited to, 2,2',2''-(10-2-((2,5-dioxopyrrolidin-1-yl)oxy)-2-oxoethyl)-1,4,7,10-tetraazacyclododecane-1,4,7-triyl)triacetic acid (DOTA)-based chelators, diethylene triamine pentaacetic acid (DTPA)-based chelators, ethylene diamine tetraacetic acid (EDTA), and a derivative or a combination thereof.

In another aspect, the nanoparticles comprise one or more therapeutic agents that are encapsulated in the hydrophobic interior of the nanoparticle. In an aspect, the one or more therapeutic agents are CT20p. In another aspect, the one or more therapeutic agentare a mutant CT20 peptide. In an aspect, the one or more therapeutic agents are a mitotoxic peptide. In an aspect, the one or more therapeutic agents are anti-metastatic agents. In an aspect, the one or more therapeutic agents are anti-androgenic agents. In an aspect, the one or more therapeutic agents are anti-neoplastic agents.

In an aspect, the one or more therapeutic agents are selected from one or more antimicrobial compounds, one or more antibacterial compounds, one or more antifungal compounds, or one or more anti-cancer agents, or a combination thereof. In an aspect, a disclosed therapeutic composition can comprise one or more anti-cancer agents. In an aspect, the one or more anti-cancer agents can comprise cisplatin. In an aspect, the one or more anti-cancer drugs induce apoptosis. In an aspect, a disclosed therapeutic composition can comprise one or more chemotherapeutic drugs. In an aspect, a disclosed therapeutic composition can comprise one or more radiosensitizers. In an aspect, a disclosed therapeutic composition can comprise a pharmaceutically acceptable carrier.

In an aspect, a disclosed therapeutic composition can comprise (i) one or more therapeutic agents, (ii) one or more anti-cancer agents, (iii) one or more chemotherapeutic drugs, and/or (iv) one or more radiosensitizers. In an aspect, a disclosed therapeutic composition can comprise one or more anti-cancer agents and one or more chemotherapeutic drugs. In an aspect, a disclosed therapeutic composition can comprise one or more anti-cancer agents and one or more radiosensitizers. In an aspect, a disclosed therapeutic composition can comprise one or more chemotherapeutic agents and one or more radiosensitizers.

In an aspect, disclosed herein is a therapeutic composition comprising a CT20 peptide. In an aspect, a disclosed CT20 peptide can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs 1-6 For example, in an aspect, a disclosed CT20 peptide can be VTIFVAGVLTASLTIWKKMG (SEQ ID NO: 1) In an aspect, a disclosed CT20 peptide can be ASLTIWKKMG (SEQ ID NO: 2). In an aspect, a disclosed CT20 peptide can be VTIFVAGVLT (SEQ ID NO: 3). In an aspect, a disclosed CT20 peptide can be VTIFVAG (SEQ ID NO: 4). In an aspect, a disclosed CT20 peptide can be IFVAG (SEQ ID NO. 5). In an aspect, a disclosed CT20 peptide can be IWKKMG (SEQ ID NO. 6). In an aspect, a disclosed therapeutic composition can comprise one or more CT20 peptides, wherein the one or more CT20 peptides can comprise SEQ ID NO:1, SEQ NO: 2, SEQ ID NO: 3. SEQ ID NO: 4, SEQ ID NO: 5, or SEQ ID NO: 6, or a combination thereof.

In an aspect, a disclosed therapeutic composition can be administered systemically to a subject. In an aspect, the subject can be a mammal. In an aspect, the mammal can be a primate. In an aspect, the mammal can be a human. In an aspect, the human can be a patient.

In an aspect, a disclosed therapeutic composition can be administered to a subject repeatedly. In an aspect, a disclosed therapeutic composition can be administered to the subject at least two times. In an aspect, a disclosed therapeutic composition can be administered to the subject two or more times. In an aspect, a disclosed therapeutic composition can be administered at routine or regular intervals. For example, in an aspect, a disclosed therapeutic composition can be administered to the subject one time per day, or two times per day, or three or more times per day. In an aspect, a disclosed therapeutic composition can be administered to the subject daily, or one time per week, or two times per week, or three or more times per week, etc. In an aspect, a disclosed therapeutic composition can be administered to the subject weekly, or every other week, or every third week, or every fourth week, etc. In an aspect, a disclosed therapeutic composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect, following the administration of a disclosed therapeutic composition, the cells are sensitized to treatment. In an aspect, following the administration of a disclosed therapeutic composition, a subject can be sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed therapeutic composition. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed therapeutic composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a cancer therapeutic composition comprising at least one nanoparticle conjugated with a targeting ligand that is a substrate for a solid tumor-specific cell protein, wherein the nanoparticle further comprises one or more therapeutic agents encapsulated in the hydrophobic interior of the nanoparticle. In an aspect, disclosed herein is a therapeutic composition and one or more anti-cancer drugs. Disclosed herein is a nanoparticle composition and one or more anti-cancer drugs. In an aspect, the disclosed compositions or nanoparticles can comprise two or more therapeutic agents. Any combination of one or more drugs that can be encapsulated by the disclosed nanoparticles (e.g., HBPE) can be used Examples include, but are not limited, to DNA intercalators (like doxorubicin, cisplatin, carboplatin), topoisomerase inhibitors, microtubule stabilizers (taxol), receptor kinase inhibitors, kinase inhibitors, aromatase inhibitors, and anti-androgens. Also, hydrophobic therapeutics soluble in DMSO, DMF or ethanol, with different degrees of hydrophobicity (as shown with the example of DiI, DiD, and DiR).

Pharmaceutical Compositions

In an aspect, the disclosed subject matter relates to pharmaceutical compositions comprising a disclosed composition comprising at least one nanoparticle conjugated with a targeting ligand that is a substrate for a solid tumor-specific cell protein. In an aspect, the disclosed composition further comprises an imaging compound and one or more therapeutic agents encapsulated in the hydrophobic interior of the nanoparticle. In an aspect, the disclosed subject matter relates to pharmaceutical compositions comprising a disclosed cancer therapeutic composition comprising the disclosed composition. In an aspect, a pharmaceutical composition can be provided comprising a therapeutically effective amount of at least one disclosed composition and a pharmaceutically acceptable carrier.

Methods Comprising a Disclosed Composition
Methods of Identifying a Solid Tumor Cell Target Disclosed herein is a method of identifying a solid tumor cell target, comprising: contacting a cell with an effective amount of a composition comprising at least one nanoparticle conjugated with a targeting ligand that is a substrate for a solid tumor-specific cell protein; identifying one or more nanoparticles bound to the cells by using imaging devices; and optionally, monitoring the solid tumor cell target by repeating the steps disclosed herein. Optionally, in an aspect, the disclosed method of identifying a solid tumor cell target can comprise the step of treating the solid tumor cell by killing or inhibiting its growth.

In an aspect, the solid tumor cell target is a prostate cancer cell. In an aspect, the prostate cancer cell is castration resistant prostate cancer. In an aspect, the solid tumor cell is a breast cancer cell. In an aspect, the solid tumor cell is a colon cancer cell. In an aspect, the solid tumor cell is a pancreas cancer cell. In an aspect, the solid tumor cell is a lung cancer cell.

In an aspect, the cells can be individual cells or cells that are on or in a subject. The cells can be individual cells or cells that are on or in a subject. In an aspect, the cells can be in a subject. In an aspect, the cells can be on a surface, which can be inert or can be the surface of a subject. In an aspect, the cells are cancer cells or transformed cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be prostate cancer. In an aspect, the prostate cancer can be castration resistant prostate cancer. In an aspect, the cancer can be breast cancer. In an aspect, the cancer can be colorectal cancer. In an aspect, the cancer can be lung cancer. In an aspect, the cancer can be a drug resistant cancer. In an aspect, the cancer cell can be a drug resistant cancer cell. In an aspect, a disclosed therapeutic composition can be administered directly into a tumor. In an aspect, a disclosed therapeutic composition can be administered directly to the cancer cells. In an aspect, a disclosed therapeutic composition induces death of cancer cells. In an aspect, noncancerous cells do not die.

In an aspect, the nanoparticles are hyberbranched polyester polymeric nanoparticles (HBPE-NPs). In an aspect, the nanoparticles are polymeric nanoparticles. In an aspect, the nanoparticles can comprise a targeting moiety. In an aspect, the nanoparticles are conjugated with a targeting ligand. In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, the nanoparticles further comprise an imaging compound. In aspect, the imaging compound is a PET detectable compound. In an aspect, the PET detectable compound is $^{89}$Zr. In an aspect, the PET detectable compound is CU or other PET detectable compounds. In an aspect, the nanoparticles comprise a chelating ligand such as desferrioxamine (DFO). In an aspect, the nanoparticles are polyglutamated folate-HBPE-DFO[CT20p]-nanoparticles. In an aspect, the nanoparticle comprises PEG.

In another aspect, the nanoparticles comprise one or more therapeutic agents that are encapsulated in the hydrophobic interior of the nanoparticle. In an aspect, the one or more therapeutic agents are CT20p. In another aspect, the one or more therapeutic agents are a mutant CT20 peptide. In an aspect, the one or more therapeutic agents are a mitotoxic peptide. In an aspect, the one or more therapeutic agents are anti-metastatic agents. In an aspect, the one or more therapeutic agents are anti-androgenic agents. In an aspect, the one or more therapeutic agents are anti-neoplastic agents.

In an aspect, the one or more therapeutic agents are selected from one or more antimicrobial compounds, one or more antibacterial compounds, one or more antifungal compounds, or one or more anti-cancer agents, or a combination thereof. In an aspect, a disclosed therapeutic composition can comprise one or more anti-cancer agents. In an aspect, the one or more anti-cancer agents can comprise cisplatin. In an aspect, the one or more anti-cancer drugs induce apoptosis. In an aspect, a disclosed therapeutic composition can comprise one or more chemotherapeutic drugs. In an aspect, a disclosed therapeutic composition can comprise one or more radiosensitizers. In an aspect, a disclosed therapeutic composition can comprise a pharmaceutically acceptable carrier.

In an aspect, a disclosed therapeutic composition can comprise (i) one or more therapeutic agents. (ii) one or more anti-cancer agents, (iii) one or more chemotherapeutic drugs, and (iv) one or more radiosensitizers. In an aspect, a disclosed therapeutic composition can comprise one or more anti-cancer agents and one or more chemotherapeutic drugs. In an aspect, a disclosed therapeutic composition can comprise one or more anti-cancer agents and one or more radiosensitizers. In an aspect, a disclosed therapeutic composition can comprise one or more chemotherapeutic agents and one or more radiosensitizers.

In an aspect, disclosed herein is a therapeutic composition, comprising a CT20 peptide. In an aspect, a disclosed CT20 peptide can comprise SEQ ID NO: 1, SEQ ID NO. 2, SEQ ID NO: 3, SEQ ID NO: 4, SEQ ID NO: 5, and/or SEQ ID NO: 6, or a combination of two or more of SEQ ID NOs: 1-6. For example, in an aspect, a disclosed CT20 peptide can be VTIFVAGVLTASLTIWKKMG (SEQ ID NO: 1). In an aspect, a disclosed CT20 peptide can be ASLTIWKKMG (SEQ ID NO: 2). In an aspect, a disclosed CT20 peptide can be VTIFVAGVLT (SEQ ID NO: 3). In an aspect, a disclosed CT20 peptide can be VTIFVAG (SEQ ID NO: 4). In an aspect, a disclosed CT20 peptide can be IFVAG (SEQ ID NO: 5). In an aspect, a disclosed CT20 peptide can be IWKKMG (SEQ ID NO: 6). In an aspect, a disclosed therapeutic composition can comprise one or more CT20 peptides, wherein the one or more CT20 peptides can comprise SEQ ID NO 1. SEQ NO: 2, SEQ ID NO: 3, SEQ ID NO: 4, SEQ ID NO: 5, or SEQ ID NO: 6, or a combination thereof. In an aspect, a method of identifying a solid tumor cell target comprising contacting a cell with a disclosed therapeutic composition that can induce cell death. In an aspect, the cell death mimics necrosis. In an aspect the cell death occurs independent of endogenous Bax activity. In an aspect, the cell death can occur independent of endogenous caspase activity. In an aspect, the cell death can be resistant to Bcl-2 over-expression.

In an aspect, a method of identifying a solid tumor cell target comprising contacting a cell with a disclosed therapeutic composition that induces cell death, wherein (i) the cell death mimics necrosis, (ii) the cell death occurs independent of endogenous Bax activity, (iii) the cell death occurs independent of endogenous caspase activity, or (iv) the cell death is resistant to Bcl-2 over-expression, or (%) the cell death exhibits a combination thereof.

In an aspect, a method of identifying a solid tumor cell target comprising contacting a cell with a disclosed therapeutic composition such that the disclosed therapeutic composition can be administered systemically to a subject. In an aspect, the subject can be a mammal. In an aspect, the mammal can be a primate. In an aspect, the mammal can be a human. In an aspect, the human can be a patient.

In an aspect, a method of identifying a solid tumor cell target comprising contacting a cell with a disclosed therapeutic composition such that the disclosed therapeutic composition can be administered to a subject repeatedly. In an aspect, a disclosed therapeutic composition can be administered to the subject at least two times. In an aspect, a disclosed therapeutic composition can be administered to the subject two or more times. In an aspect, a disclosed therapeutic composition can be administered at routine or regular intervals. For example, in an aspect, a disclosed therapeutic composition can be administered to the subject one time per day, or two times per day, or three or more times per day. In an aspect, a disclosed therapeutic composition can be administered to the subject daily, or one time per week, or two times per week, or three or more times per week, etc. In an aspect, a disclosed therapeutic composition can be administered to the subject weekly, or every other week, or every third week, or every fourth week, etc. In an aspect, a disclosed therapeutic composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect of a disclosed method of identifying a solid tumor cell target comprising contacting a cell with a disclosed therapeutic composition, the cells are sensitized to treatment following the administration of a disclosed therapeutic composition. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed therapeutic composition. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed therapeutic composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a therapeutic composition and one or more anti-cancer drugs.

Methods of Treating Prostate Cancer

Disclosed herein are methods of treating prostate cancer. In an aspect, disclosed herein are method for treating prostate cancer, comprising administering to a subject diagnosed with prostate cancer an effective amount of a nanoparticle composition, comprising at least one nanoparticle conjugated with a targeting ligand that is a substrate for a solid tumor-specific cell protein. In an aspect, the nanoparticle further comprises an imaging compound. In an aspect, the nanoparticle has one or more therapeutic agents encapsulated in the hydrophobic interior of the nanoparticle. Additional therapeutica and/or radiolabeled compounds can be administered with (either separately, before and/or after, or simultaneously) with the nanoparticles.

In an aspect, the cells can be individual cells or cells that are on or in a subject. The cells can be individual cells or cells that are on or in a subject. In an aspect, the cells can be in a subject. In an aspect, the cells can be on a surface, which can be inert or can be the surface of a subject. In an aspect, the cells are cancer cells or transformed cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be prostate cancer. In an aspect, the prostate cancer can be castration resistant prostate cancer. In an aspect, the cancer can be breast cancer. In an aspect, the cancer can be colorectal cancer. In an aspect, the cancer can be lung cancer. In an aspect, the cancer can be a drug resistant cancer. In an aspect, the cancer cell can be a drug resistant cancer cell. In an aspect, a disclosed therapeutic composition can be administered directly into a tumor. In an aspect, a disclosed therapeutic composition can be administered directly to the cancer cells. In an aspect, a disclosed therapeutic composition induces death of cancer cells. In an aspect, noncancerous cells do not die.

In an aspect, the nanoparticles are hyberbranched polyester polymeric nanoparticles (HBPE-NPs). In an aspect, the nanoparticles are polymeric nanoparticles. In an aspect, the nanoparticles can comprise a targeting moiety. In an aspect, the nanoparticles are conjugated with a targeting ligand. In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, the nanoparticles further comprise an imaging compound. In aspect, the imaging compound is a PET detectable compound. In an aspect, the PET detectable compound is $^{89}$Zr. In an aspect, the PET detectable compound is CU or other PET detectable compounds. In an aspect, the nanoparticles comprise a chelating ligand such as desferrioxamine (DFO). In an aspect, the nanoparticles are polyglutamated folate-HBPE-DFO[CT20p]-nanoparticles. In an aspect, the nanoparticle comprises PEG In another aspect, the nanoparticles comprise one or more therapeutic agents that are encapsulated in the hydrophobic interior of the nanoparticle. In an aspect, the one or more therapeutic agents are CT20p. In another aspect, the one or more therapeutic agents are a mutant CT20 peptide. In an aspect, the one or more therapeutic agents are a mitotoxic peptide. In an aspect, the one or more therapeutic agents are anti-metastatic agents. In an aspect, the one or more therapeutic agents are anti-androgenic agents. In an aspect, the one or more therapeutic agents are anti-neoplastic agents.

In an aspect, the one or more therapeutic agents are selected from one or more antimicrobial compounds, one or more antibacterial compounds, one or more antifungal compounds, or one or more anti-cancer agents, or a combination thereof. In an aspect, a disclosed therapeutic composition can comprise one or more anti-cancer agents. In an aspect, the one or more anti-cancer agents can comprise cisplatin. In an aspect, the one or more anti-cancer drugs induce apoptosis. In an aspect, a disclosed therapeutic composition can comprise one or more chemotherapeutic drugs. In an aspect, a disclosed therapeutic composition can comprise one or more radiosensitizers. In an aspect, a disclosed therapeutic composition can comprise a pharmaceutically acceptable carrier.

In an aspect, a disclosed therapeutic composition can comprise (i) one or more therapeutic agents, (ii) one or more anti-cancer agents, (iii) one or more chemotherapeutic drugs, and (iv) one or more radiosensitizers. In an aspect, a disclosed therapeutic composition can comprise one or more anti-cancer agents and one or more chemotherapeutic drugs. In an aspect, a disclosed therapeutic composition can comprise one or more anti-cancer agents and one or more radiosensitizers. In an aspect, a disclosed therapeutic composition can comprise one or more chemotherapeutic agents and one or more radiosensitizers.

In an aspect, disclosed herein is a therapeutic composition, comprising a CT20 peptide. In an aspect, a disclosed CT20 peptide can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a disclosed CT20 peptide can be VTIFVAGVLTASLTIWKKMG (SEQ ID NO: 1). In an aspect, a disclosed CT20 peptide can be ASLTIWKKMG (SEQ ID NO: 2). In an aspect, a disclosed CT2 peptide can be VTIFVAGVLT (SEQ ID NO: 3). In an aspect, a disclosed CT20 peptide can be VTIFVAG (SEQ ID NO: 4). In an aspect, a disclosed CT20 peptide can be IFVAG (SEQ ID NO: 5). In an aspect, a disclosed CT20 peptide can be IWKKMG (SEQ ID NO: 6). In an aspect, a disclosed therapeutic composition can comprise one or more CT20 peptides, wherein the one or more CT20 peptides can comprise SEQ ID NO-1. SEQ NO: 2, SEQ ID NO: 3, SEQ ID NO: 4, SEQ ID NO: 5, or SEQ ID NO: 6, or a combination thereof.

In an aspect, a method of treating prostate cancer comprising administering to a subject a disclosed nanoparticle composition that can induce cell death. In an aspect, the cell death mimics necrosis. In an aspect, the cell death occurs independent of endogenous Bax activity. In an aspect, the cell death can occur independent of endogenous caspase activity. In an aspect, the cell death can be resistant to Bcl-2 over-expression.

In an aspect, a method of treating prostate cancer comprising administering to a subject a disclosed nanoparticle composition that induces cell death, wherein (i) the cell death mimics necrosis, (ii) the cell death occurs independent of endogenous Bax activity, (iii) the cell death occurs independent of endogenous caspase activity, or (iv) the cell death is resistant to Bcl-2 over-expression, or (v) the cell death exhibits a combination thereof.

In an aspect, a method of treating prostate cancer comprising administering to a subject a disclosed nanoparticle composition such that the disclosed nanoparticle composition can be administered systemically to a subject. In an aspect, the subject can be a mammal. In an aspect, the mammal can be a primate. In an aspect, the mammal can be a human. In an aspect, the human can be a patient.

In an aspect, a method of treating prostate cancer comprising administering to a subject a disclosed nanoparticle composition such that the disclosed nanoparticle composition can be administered to a subject repeatedly. In an aspect, a disclosed nanoparticle composition can be administered to the subject at least two times. In an aspect, a disclosed nanoparticle composition can be administered to the subject two or more times. In an aspect, a disclosed nanoparticle composition can be administered at routine or regular intervals. For example, in an aspect, a disclosed nanoparticle composition can be administered to the subject one time per day, or two times per day, or three or more times per day. In an aspect, a disclosed nanoparticle composition can be administered to the subject daily, or one time per week, or two times per week, or three or more times per week, etc. In an aspect, a disclosed nanoparticle composition can be administered to the subject weekly, or every other week, or every third week, or every fourth week, etc. In an aspect, a disclosed nanoparticle composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect of a disclosed method of treating prostate cancer comprising administering to a subject a disclosed nanoparticle composition, the cells are sensitized to treatment following the administration of a disclosed nanoparticle composition. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed nanoparticle composition to the sensitivity of a cell or subject that has not been administered a disclosed nanoparticle composition.

For example, in an aspect, following the administration of a disclosed nanoparticle composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed nanoparticle composition. In an aspect, following the administration of a disclosed nanoparticle composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed nanoparticle composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

EXAMPLES

The following examples are put forth so as to provide those of ordinary skill in the art with a complete disclosure and description of how the compounds, compositions, and methods claimed herein are used and evaluated and are intended to be purely exemplary of the disclosed subject matter and are not intended to limit the scope of what the inventors regard as their invention. However, those of skill in the art should, in light of the present disclosure, appreciate that many changes can be made in the specific aspects which are disclosed and still obtain a like or similar result without departing from the spirit and scope of the invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

(1) Utilization of a Hyperbranched Polyester (HBPE) Nanoparticle

Figure 2:
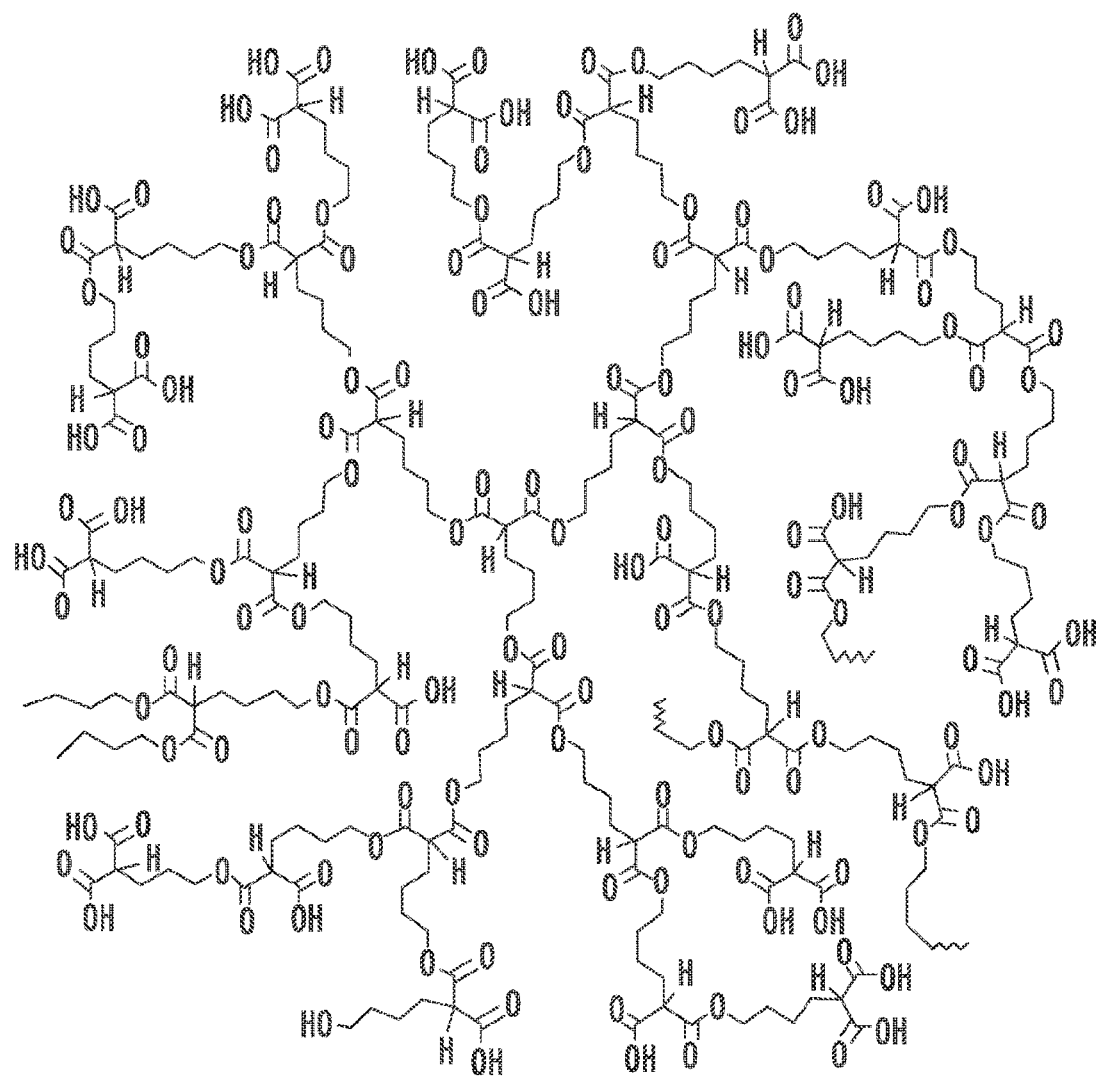
FIG. 2 depicts the structure of a HBPE polymer.

In one aspect, disclosed are spherically-shaped, highly branched HBPE nanoparticles that encapsulate therapeutic and imaging cargos within their hydrophobic nanocavities, without affecting the distribution of targeting ligands on the nanoparticle's surface. The nanoparticle's surface comprise carboxylic acid groups that can be functionalized with targeting ligands to generate a library of functional targeting nanoparticles with high and low valency. These nanoparticles are easily fabricated from an aliphatic, biodegradable, hyperbranched polyester (HBPE) polymer (FIG. 2) that displays a defined number of carboxylic functional groups. As these carboxylic acid groups are not used for conjugation of therapeutic drugs or imaging agents, they are readily available for conjugation of the targeting ligands at high and low density in such a way that the effect of ligand multivalency and its effect on tumor targeting can be studied. The HBPE polymer disclosed herein has great advantages over conventional linear polymers (such as PLGA) since: (i) it is highly branched creating unique hydrophobic cavities; (ii) it displays a high number of carboxylic acid groups on its surface for facile labeling; and (iii) its monomer contains an acidic proton that can be easily displaced by a pendant ligand, allowing further functionalization of the resulting nanoparticles' cavity to introduce a chelating ligand for stable encapsulation of radioactive isotopes for PET imaging. Notice that with current linear polymers, it is difficult to engineer the resulting nanoparticle to achieve the advantages of the HBPE nanoparticles, as they don't generate well-defined hydrophilic nanocavities that can be further modified chemically to introduce further functionalities. In contrast, dendrimers, although highly branched and containing a high number of functional groups on the surface, are more difficult to synthesize and to chemically engineer their nanocavities to introduce further functionalities. Taken together, a main innovative aspect of the compositions and methods described herein is the use of a HBPE polymer to fabricate a multifunctional theranostic polymeric nanoparticle targeting PSMA via multivalent interaction, while chemically engineering its nanocavities to incorporate chelating agents for PET imaging and efficiently encapsulating a therapeutic drug.

(2) Using Folates and Glutamate Ligands to Target PSMA

In another aspect, disclosed are the design and screening of folate and glutamate containing ligands to target PSMA. Considering that PSMA utilized polyglutamated folate as its biological ligand and it was shown herein that both glutamic acid- and folic acid-conjugated HBPE nanoparticles target PSMA (FIGS. 5-7), a rationally designed library of small molecules containing both glutamate and folate derivatives were developed to be conjugated onto the HBPE nanoparticles for targeting PSMA. Screening of this compound library generated polyglutamated folate compounds with higher, more specific binding toward PSMA with minimal binding to the folate receptor. Conjugation of these ligands was done at high and low density to study the effect of multivalency on the PSMA-targeting nanoparticle conjugates. The disclosed methods are innovative, as the methods are directed to the effect of the nanoparticles' ligand density on PSMA targeting, using small molecule ligands (glutamate and folate) scaffolds that were shown to bind to PSMA-expressing cells. Glutamate urea-based small molecules have been previously developed as PSMA inhibitors and PET imaging agents of PSMA expression in PCa in animal models. These small molecules exhibited good pharmacokinetic and biodistribution profiles, being able to selectively image PSMA in mice xenografts with high target to non-target tissue ratios. Furthermore, glutamate urea-based PSMA inhibitors were also conjugated to polymeric nanoparticles to deliver doxorubicin to PSMA positive cells. This previous work clearly demonstrates that small molecules can be used to target PSMA; however, the methods disclosed herein are significantly different from these previous investigations since (1) folic acid, a targeting ligand that has not been tested before to target nanoparticles to PSMA was used, and (2) a systematic study on the effect of a multivalent folate/glutamate ligand presentation on PSMA binding was performed using a theranostic nanoparticle. As these small molecules are more stable and easier to manufacture than monoclonal anti-PSMA antibodies or aptamers, members of the resulting multivalent HBPE nanoparticle library provide a more robust PSMA-targeting nanoplatform to target PCa Through screening a compound library of small molecules containing folate and glutamate ligands, being displayed on a polymeric nanoparticle at high vs, low density, a nanoparticle-small molecule conjugate that specifically binds to PSMA while displaying minimal binding to the folate receptor was observed. Even though folate conjugated nanoparticles have been developed to target the folate receptor, their binding to PSMA has not been investigated.

(3) A Theranostic Approach for Dual Targeting and Imaging

Figure 3:
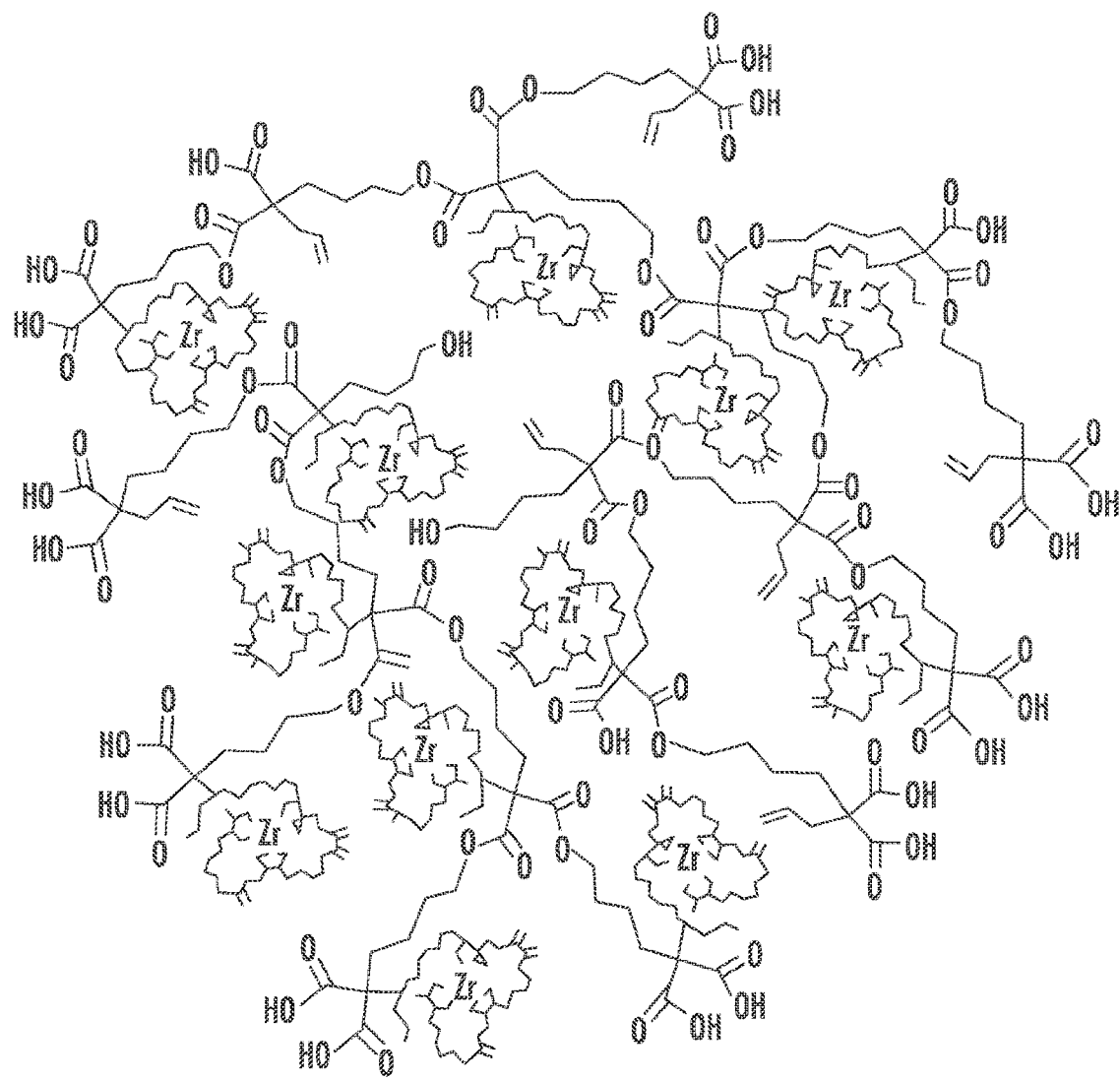
FIG. 3 depicts the structure of a DFO-Zr-HBPE polymer.

In another aspect, disclosed is the design of a theranostic nanoparticle that is able to deliver an antiandrogenic drug and a PET imaging tracer to PCa via PSMA targeting. This capability is a unique and translational advancement for the treatment of PCa as the PET imaging capability allows monitoring of the delivery of the therapeutic nanoparticle. To endow the nanoparticles with PET imaging capabilities, a method of grafting desferrioxamine (DFO) onto the HBPE nanoparticle cavities was developed. Desferrioxamine (DFO) strongly binds Zr and has been used in the design of $^9$Zr-PET imaging probes. The HBPE nanoparticle's synthetic procedure was modified to yield a DFO-grafted HBPE nanoparticle able to chelate $^9$Zr (FIG. 3). Introducing a pendant group with selective $^9$Zr-chelating ability into the hydrophobic cavities increased the ability of the HBPE nanoparticle to chelate $^{89}$Zr. These nanoparticles chelate $^{89}$Zr and encapsulate a hydrophobic drug, while displaying targeting ligands: thus creating a theranostic nanoparticle that specifically bind PSMA. For these studies, abiraterone and MDV-3100 were selected as therapeutic agents for encapsulation into the PSMA-targeting nanoparticles. Abiraterone and MDV-3100 are PCa drugs, currently on clinical trials for the treatment of PCa and are administered orally. These two drugs work by inhibiting the androgen (testosterone) mediated pathway that facilitates PCa development. However, clinical assessment of drug delivery is not currently possible with these drug formulations. Also, enteric uptake efficacy and first pass effects through the liver all decrease the actual availability of the drug to treat PCa. Therefore, disclosed herein is the targeted delivery of abiraterone or MDV-3100 in high concentrations selectively to PCa, which significantly reduced side effects, while allowing assessment of nanoparticle delivery via PET imaging.

The incorporation of $^{89}$Zr facilitated the assessment of nanoparticle localization via PET imaging as this radioisotope is a promising long-lived positron emitter for the detection of tumors by PET. The $^{89}$Zr radionuclide has multiple advantages over the typically used $^{64}$Cu radionuclide such as (1) a half-life of approximately 78.4 h (3.17 days) as opposed to the 12.7 h for the $^{64}$Cu isotope, (2) a positron yield of 22.7% which improves counting statistics when compared to other radioisotopes, (3) no known toxicity to biological systems, and (4) generation of $^{89}$Zr is cost effective and highly efficient. Recently, =the use of a $^{89}$Zr-labeled antibodies to image HER2/neu-positive44 and PSMA-positive45 tumors in vivo was reported and the potential clinical use of this radiotracer for localizing and staging these tumors was suggested. However, a nanoparticle with the capability of chelating $^{89}$Zr for PET imaging applications has not been reported. Therefore, disclosed herein are methods of designing, fabricating, and characterizing a DFO-grafted HBPE nanoparticle to chelate $^{89}$Zr for PET imaging of PSMA positive PCa tumors.

Figure 4:
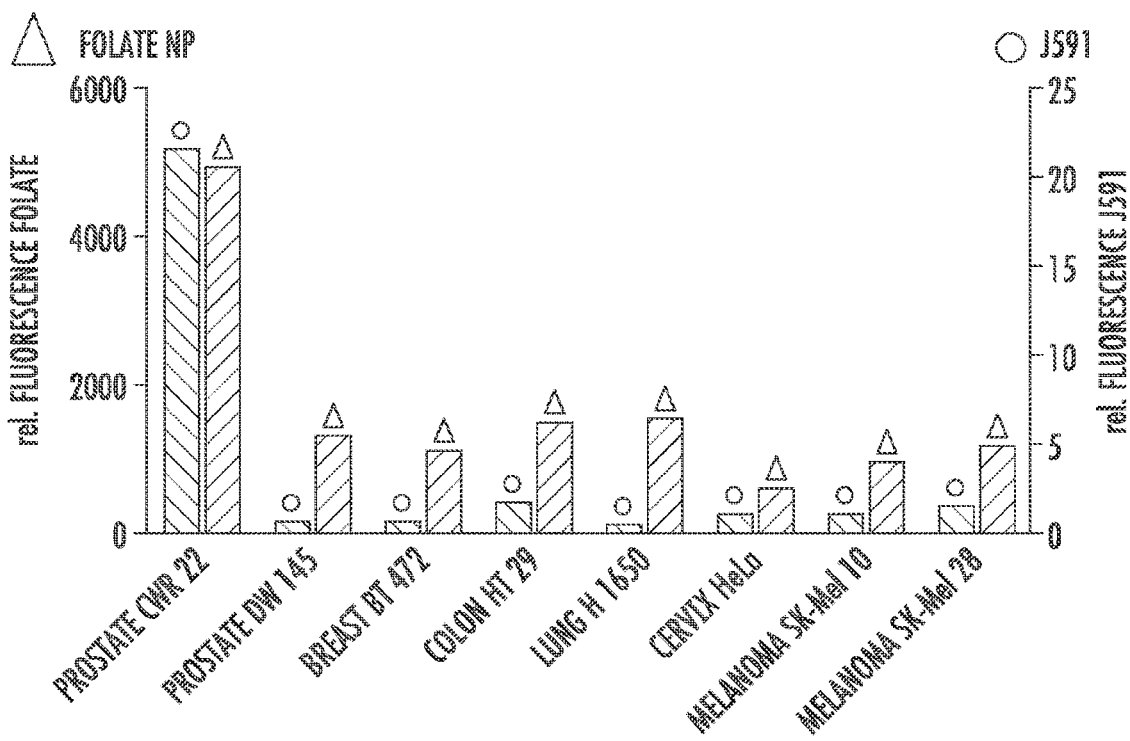
FIG. 4 is a graph showing the cell-associated fluorescence of various cancer cell lines after treatment with HBPE(DiI)-folate nanoparticles (folate NP, left axis). The presence of PSMA in these cell lines was corroborated using the anti-PSMA antibody J590 (right axis).

The synthesis and characterization of the first generation HBPE nanoparticles via the solvent diffusion method are disclosed herein. In this method, both the hydrophobic polymer and guest molecule to be encapsulated were dissolved in a water-miscible organic solvent (e.g., DMF or DMSO) and the solution was added drop-wise to a beaker containing water under constant stirring (FIG. 4). Under these conditions, the miscible solvent rapidly diffused into the water, causing the polymer to self-assemble, forming polymeric nanoparticles encapsulating the hydrophobic molecules within hydrophobic pockets. This process exposed the hydrophilic segments of the polymer to the aqueous solution, resulting in the formation of carboxyl-functionalized nanoparticles. The presence of multiple carboxylic acid groups on the nanoparticle's surface enabled the conjugation of multiple targeting ligands, creating a multivalent targeting nanoparticle. The effect of multivalency on the detection profile of cancer cells by conjugating folic acid at two different densities (low-folate and high-folate) on iron oxide nanoparticles was studied and their interactions with lung cancer cells expressing the folate receptor were studied. Results showed that the multivalent high-folate nanoparticle performed better than its low folate counterpart, achieving single cancer cell detection within 15 min. Therefore, a high valency polyglutamated folate nanoparticle achieves selective binding to PSMA-expressing PCa cells.

Figure 5:
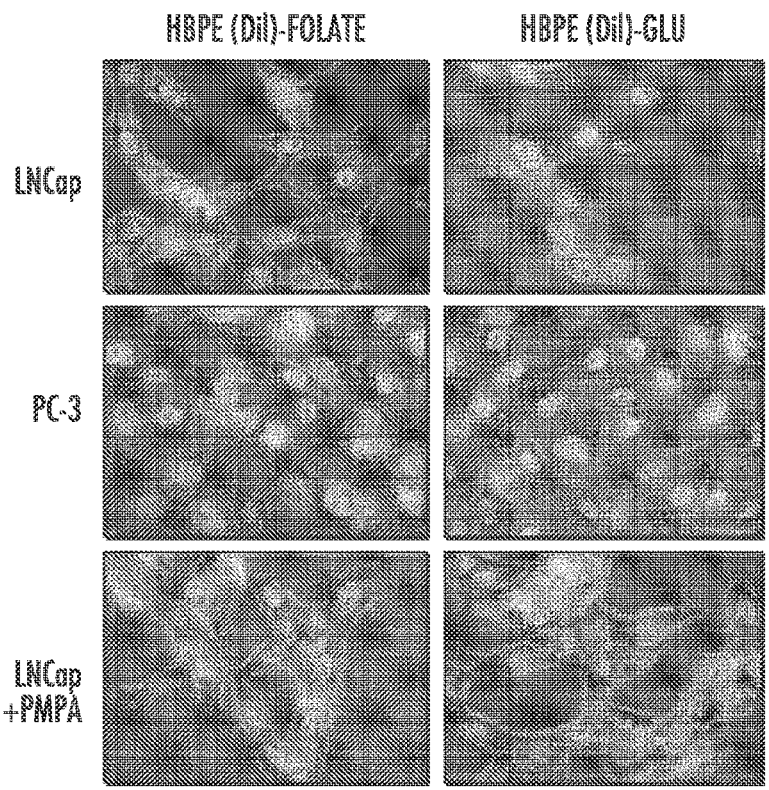
FIG. 5 shows the targeting of the PSMA receptor in LNCaP prostate cancer cells using folate and glutamate-derivatized HBPE nanoparticles.
Figure 6:
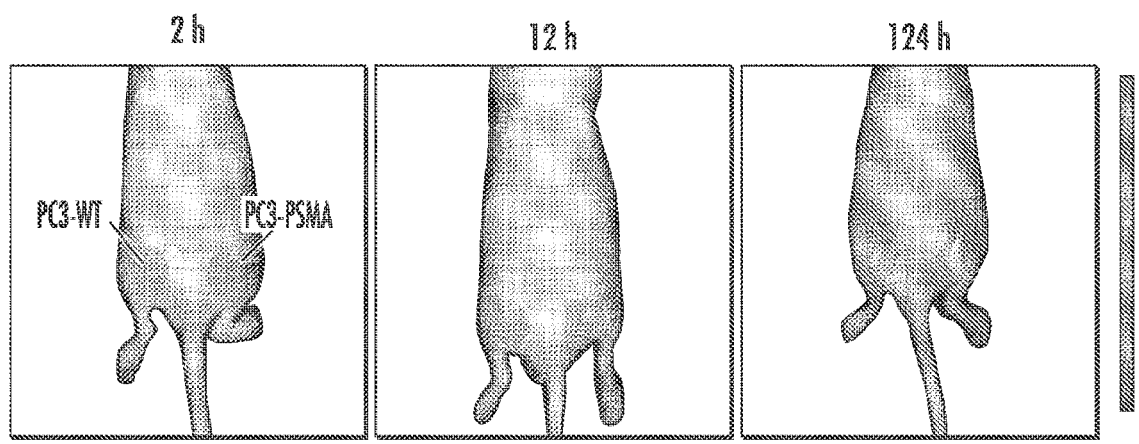
FIG. 6 depicts the accumulation of HBPE(DiR)-folate nanoparticles in PSMA positive PC3 tumor in mice. Increased uptake was observed for all time points in the PSMA-positive PC3-PSMA tumor (representative animal). (Light grey indicates high uptake, while dark grey indicates low uptake).

The synthesis and characterization of a first generation HBPE polymer (Mw=42 kDa) that was used to fabricate HBPE nanoparticles (88 nm) encapsulating a variety of hydrophobic molecules, such as near infrared dyes, anticancer drugs, and chelated metals was reported. The nanoparticles' surface carboxylic groups were functionalized with a propargyl group and conjugated with an azide functionalized folic acid ligand to yield folate-decorated HBPE nanoparticles [HBPE(DiI)-folate]. These nanoparticles delivered Taxol to folate-receptor-expressing cells resulting in substantial cell internalization and cytotoxicity within 24 h. Most recently, it was investigated whether the multivalent HBPE(DiI)-folate nanoparticles can target the PSMA receptor in PCa cell lines. In the first set of experiments, various cell lines were exposed with the HBPE(DiI)-folate nanoparticles and the degree of cell associated fluorescence was assessed using FACS analysis (FIG. 5). Results showed a significantly large amount of fluorescence associated with the CWR 22 prostate cancer cell line, which overexpressed PSMA. In contrast, the PSMA negative DU145 cell line had a reduced amount of cell associated fluorescence. Other non-prostatic cancer cell lines that did not express PSMA had reduced cell associated fluorescence, even when some of these cells (DU145, HT29, H 1650, HeLa and SL-Mel 28) expressed the folate receptor to some degree. This data indicates that the folate nanoparticles disclosed herein target PSMA in the CWR 22 prostate cancer cell line. In additional experiments, the PCa cell lines LNCaP and PC3 were used. The LNCaP cell line was ideal for these studies, because these cells express the PSMA receptor, but do not express the folate receptor, while PC3 cells arm PSMA and folate negative. The results showed that LNCaP cells incubated with the HBPE(DiI)-folate nanoparticles had a significant amount of fluorescence i the cytoplasm indicating internalization of the HBPE(DiI)-folate nanoparticles (FIG. 6). This level of cell-associated fluorescence was not observed when these nanoparticles were incubated with the PSMA negative PC3 cells. Most importantly, when LNCaP cells were preincubated with PMPA, a known inhibitor of PSMA, the internalization of the nanoparticles was drastically reduced (FIG. 6), indicating that the internalization occurred via the PSMA receptor. As neither the LNCaP nor the PC3 cells expressed significant amounts of folate receptor, these results indicate that the HBPE(DiI)-folate nanoparticles were internalized into the LNCaP cell lines via PSMA and can be used to target this receptor in vivo. In additional experiments, glutamic acid was conjugated to the nanoparticles to create a multivalent HBPE(DiI)-glutamate nanoparticles and their internalization in PCa cells was studied. As expected, LNCaP cells internalized a significant amount of these nanoparticles, while no significant uptake was observed in PC3 cells or LNCaP cells preincubated with PMPA (FIG. 6).

Figure 7:
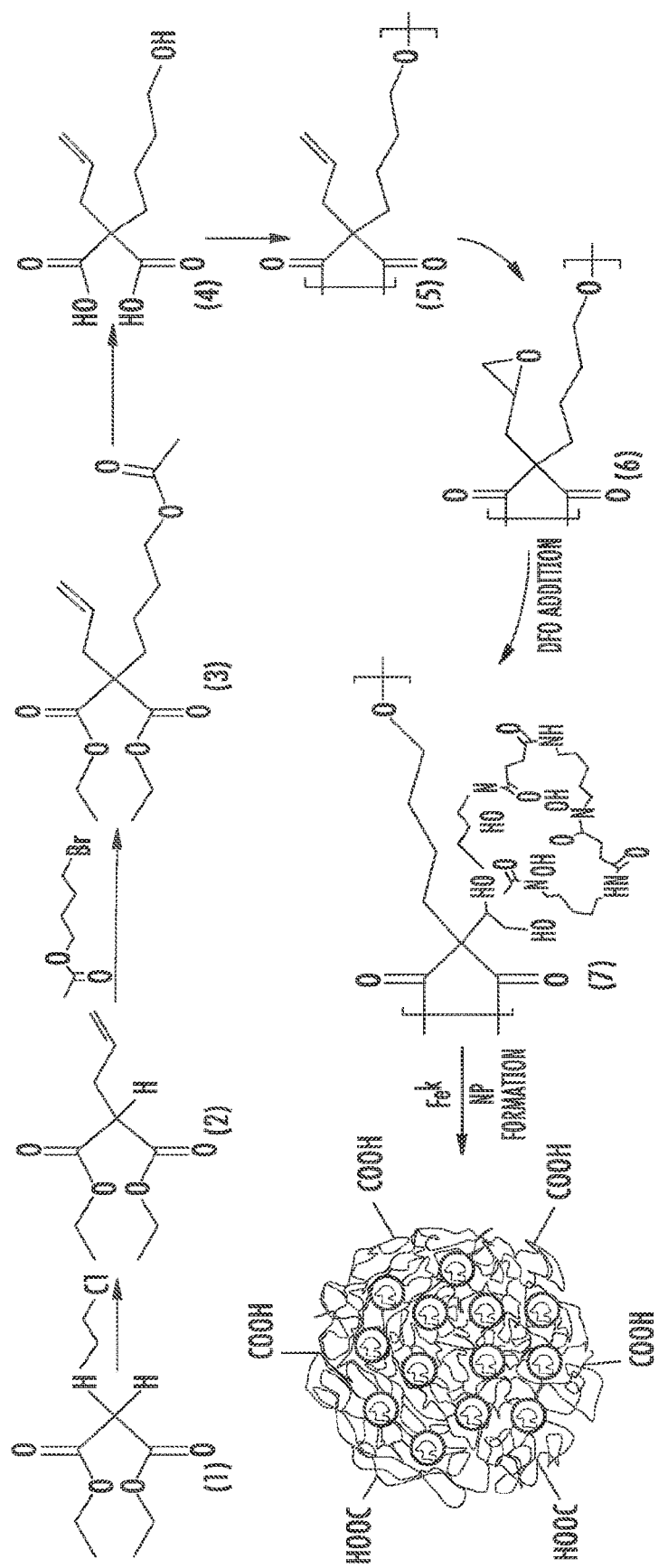
FIG. 7 depicts the synthetic route for the DFO-HBPE nanoparticle.

To assess the potential in vivo targeting ability of the nanoparticle preparations, folate-conjugated HBPE nanoparticles encapsulating the near infrared dye DiR [HBPE (DiR)-folate nanoparticles] were injected into PSMA(+) PC3 tumor-bearing mice. Fluorescence tomographic imaging results showed a significantly higher accumulation of the Folate-HBPE nanoparticles in the PSMA-transfected PC3 tumor, even 2 h after injecting the nanoparticles (FIG. 7). At 24 h, even though some time-dependent accumulation was observed in the PC3 wild-type (PSMA negative) tumor through EPR effects, a stronger tumor-associated fluorescence was observed in the PSMA transfected PC3 tumor, indicating a higher accumulation of HBPE(DiR)-folate nanoparticles. Taken together, these results strongly indicate that the HBPE nanoparticles disclosed herein target PSMA via the multivalent presentation of folate and/or glutamate ligands to deliver multiple imaging and therapeutic cargos in high concentrations to prostate cancer. The generation and screening of a library of polyglutamated folate compounds conjugated to HBPE nanoparticles resulted in lead nanoparticle conjugates with enhanced and specific binding to PSMA as opposed to the folate receptor n vivo.

Figure 8:
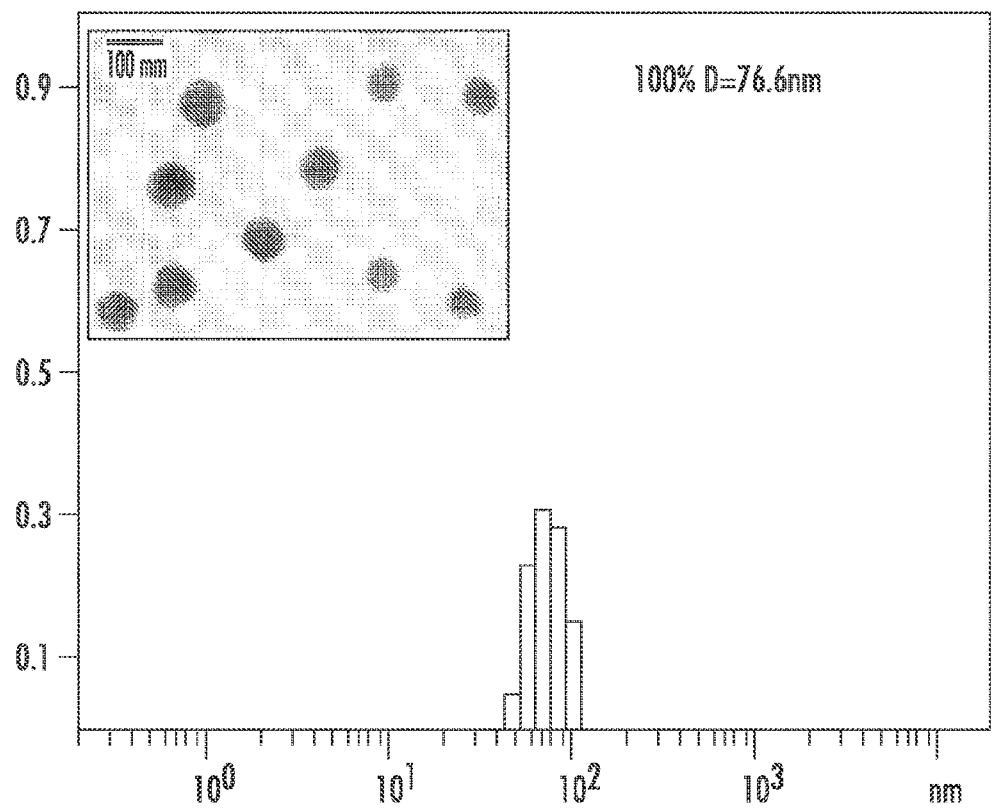
FIG. 8 shows the HBPE-DFO:Zr Nanoparticle size distribution determined by DLS. Insent: corresponding STEM image of the nanoparticles. Scale bar: 100 nm.
Figure 9B:
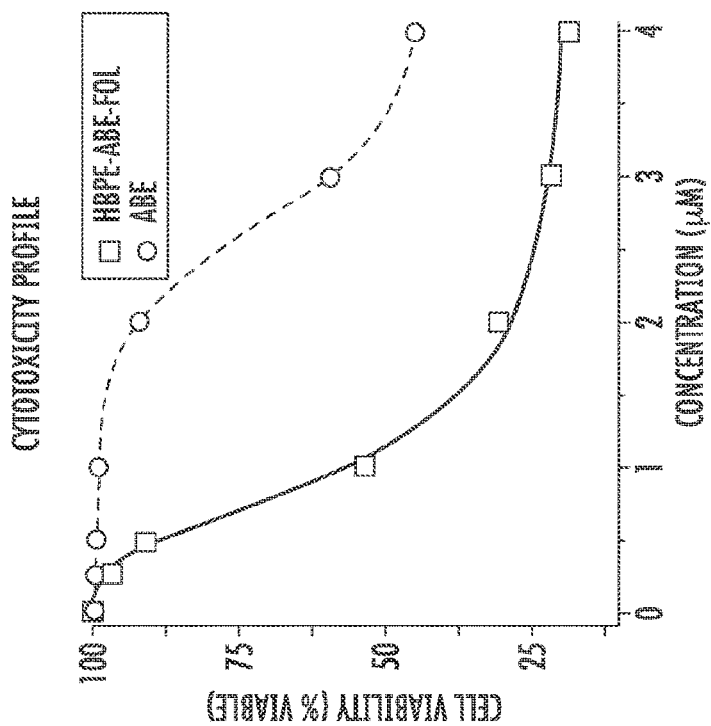
FIG. 9B is a graph showing the cytotoxicity profile of HBPE nanoparticles (ABE=abiraterone).
Figure 9A:
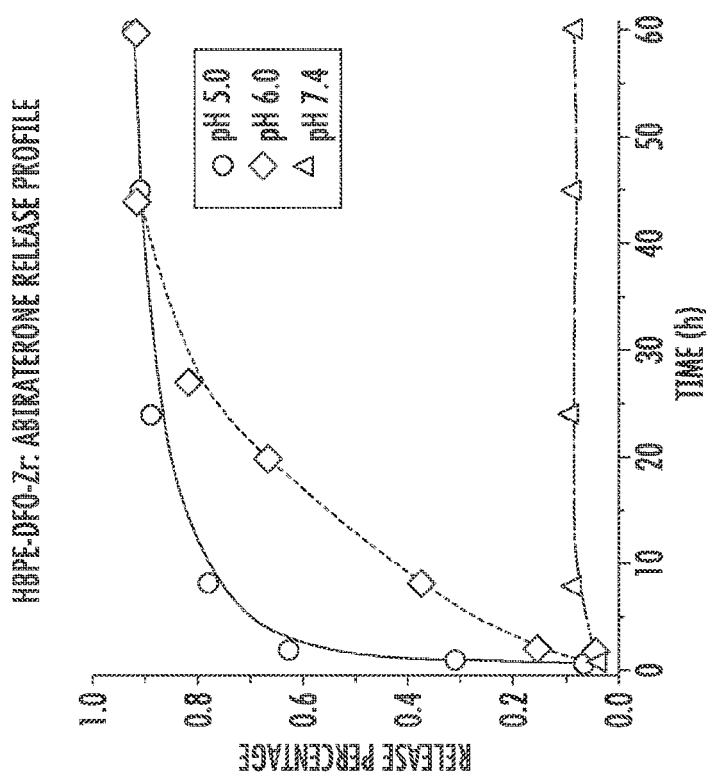
FIG. 9A is a graph showing the pH-dependent abiraterone drug release of HBPE nanoparticles.

The HBPE nanoparticle synthesis procedure was modified to yield a DFO-grafted HBPE nanoparticle that chelates $^{89}$Zr. The fabrication of the Zr-chelating HBPE nanoparticles starts with the synthesis of a DFO-grafted HBPE polymer. In the synthetic procedure (FIG. 8), diethylmalonate (1) (62.5 mmol), 3-chloroprop-1-ene (62.5 mmol) and potassium carbonate (312.5 mmol) were taken in acetonitrile and refluxed for 36 h. In this step, the use of a stoichiometric amount of chloroprop-1-ene and potassium carbonate as a mild base facilitated the release of only one acidic proton from 1 and its subsequent monoalkylation. The resulting monoalkylated product 2 (40.0 mmol), was purified by flash chromatography and reacted with 4-bromobutyl acetate (48 mmol) in a dry THF solution containing NaH (56 mmol). In this second step, the use of NaH as a stronger base and the excess amount of 4-bromobutyl acetate ensured the removal of the second acidic proton and the formation of the dialkylated compound 3. Subsequent deprotection of 3 (19.2 mmol) by hydrolysis of the protecting ester groups in an aqueous methanol solution containing NaOH (67.3 mmol) at 90° C., for 12 h, resulted in the formation of monomer 4 containing a propene group as a pendant ligand. Monomer 4 was then polymerized under vacuum using p-toluenesulfonic acid (100:1 molar ratio) as catalyst. In this step, the rate of polymerization and resulting molecular weight of the polymer was controlled by varying the temperature and time of vacuum application. The resulting propene-grafted polymer 5 was oxidized to an epoxide in order to be reactive to the terminal amine group in DFO. Briefly, 3-chloroperoxybenzoic acid (1.2 mmol) was dissolved into a mixture of dry dichloromethane (DCM) and $Na_2CO_3$ (1.2 mmol) under constant stirring in an ice bath. To this, the polymer 5 (120 mg), dissolved in dry DCM, was added slowly and then stirred for 72 h. The oxidized polymer was then precipitated in water to obtain pure epoxy-grafted polymer 6. Finally, polymer 6 (40 mg) was reacted with DFO (0.122 mmol) in a methanol solution containing triethylamine (0.203 mmol) under constant stirring, at room temperature for 24 h. The final DFO-grafted-HBPE 7 polymer was purified by precipitation in water. GPC analysis of the resulting polymer indicated a molecular weight of 40 kDa. DFO-grafted HBPE nanoparticles were synthesized via the solvent diffusion method and nanoparticles of 76±4 nm were obtained (FIGS. 9A-9B). These nanoparticles were of similar size to the first generation HBPE disclosed herein (even when containing DFO in the cavities), due to an optimization of the polymerization conditions such as time, temperature and reduced pressure. These nanoparticles were fabricated using a $Fe^{3+}$ chelated DFO to facilitate "wrapping" of the DFO around the metal for a better fitting in the nanoparticle's inner cavities. Upon incubation with cold $Zr^{4+}$ (in the form of $ZrCl_4$), the chelated $Fe^{3+}$ was easily displaced by $Zr^{4+}$. This was corroborated by ICP-MS results showing a percent by weight of $Zr^{41}$ to polymer of 0.15% in the final nanoparticle formulation. These results reveal an easy method to label the DFO-HBPE nanoparticles with $^{89}$Zr for PET studies. The results indicate that these nanoparticles encapsulate radioactive $^{89}$Zr.

Figure 10:
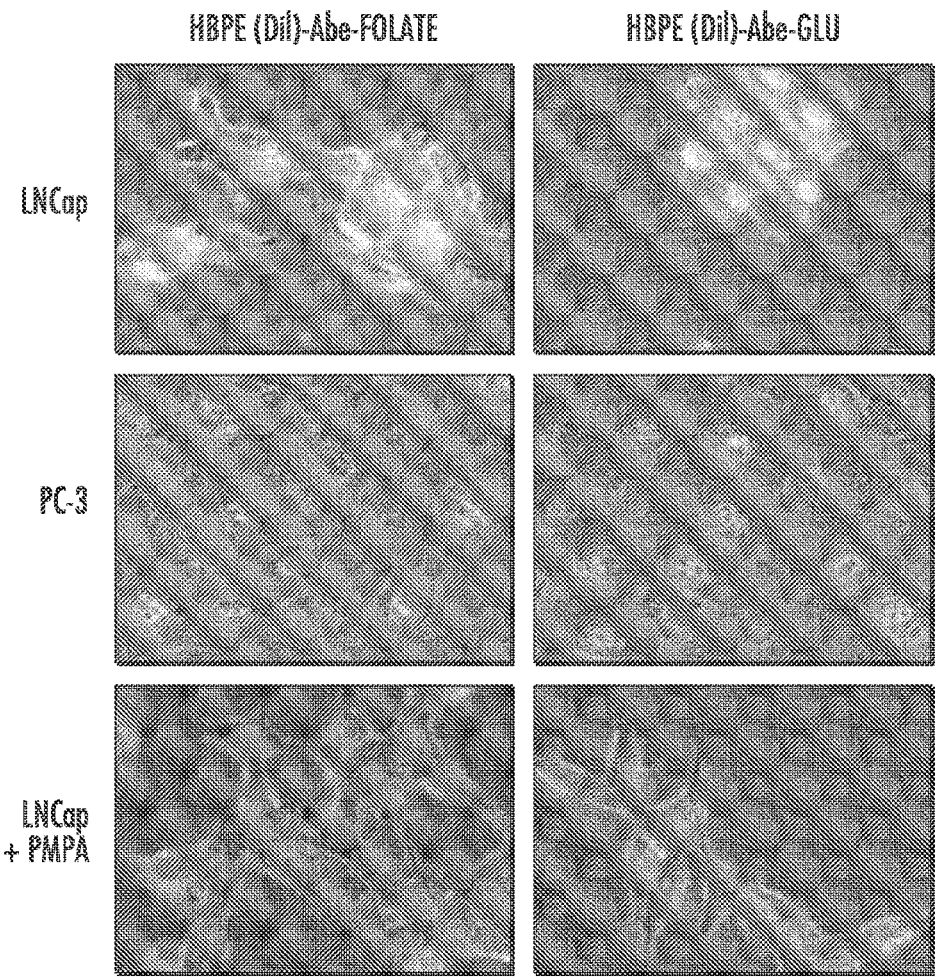
FIG. 10 depicts HBPE(DiI) folate and HBPE (DiI) glutamate nanoparticles that encapsulate abiraterone induce cell death in LNCaP cells, that express PSMA.
Figure 11:
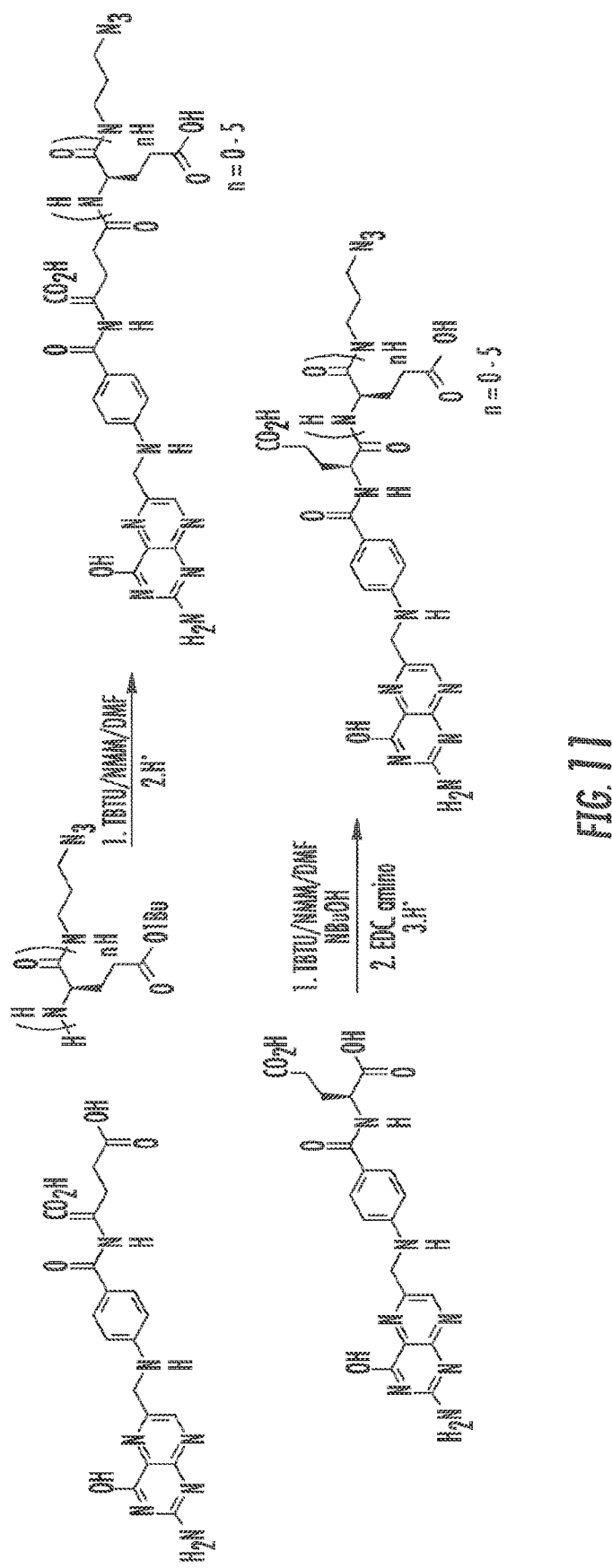
FIG. 11 depicts the general synthetic scheme toward Scaffold 1 analogs.

The DFO-grafted HBPE nanoparticles were encapsulated with abiraterone and the drug release profiles, as well as the cytotoxicity of the resulting nanoparticles, were evaluated. The amount of encapsulated abiraterone was estimated following a reported protocol and defined as encapsulation efficiency. Following this procedure, an encapsulation efficiency of 75% was estimated. The nanoparticles were stable in PBS pH 7.4 with no leaching of the nanoparticle at this pH (FIG. 10). Similarly, addition of increasing amounts of FBS to these nanoparticles did not trigger release of the drug. However, upon incubation at lower pH (6.0 and 5.0), release of the drug was observed, with a higher rate at pH 5.0. The results indicate that the nanoparticle will release the drug upon endosomal internalization and subsequent localization within acidic lysosomes. As it is known to one of ordinary skill in the art, folate-decorated nanoparticle, taken up via the PSMA receptor, is facilitated by an endosomal mechanism. The cytotoxicity of the abiraterone-loaded nanoparticles to PSMA positive LNCaP cells was corroborated via cell viability studies and determination of the $IC_{50}$. The assay indicated an $IC_{50}$ of 2.55 μM for abiraterone in solution and a lower value of 890 nM for the folate-DFO HBPE nanoparticle encapsulating abiraterone (FIG. 10). These results demonstrate that a lower $IC_{50}$ (greater therapeutic value) for abiratenone is obtained by encapsulating the drug within the polymeric nanoparticles targeting PSMA, therefore, facilitating better internalization of the drug. At a concentration higher than 2.5 μM for abiraterone alone, only 50% of the cells were dead, whereas more than 75% of the cells (25% viability) were dead at this concentration with the encapsulated and PSMA targeted drug (FIG. 10). Finally, fluorescence microscopy studies of LNCaP and PC3 cells incubated with folate- and glutamate-HBPE(Abiraterone/DiI), indicated a significant amount of nanoparticle internalization and cell death in LNCaP cells, but not in PC3 cells or LNCaP cells pre-incubated with a PSMA inhibitor (FIG. 11). Taken together, these studies indicated that the polymeric nanoparticles disclosed herein are an ideal nanoplatform to deliver potent drugs to PCa cells, increasing their efficacy. Furthermore, these studies showed that folate and glutamate derivatives selectively target the delivery of these drugs to PCa via PSMA.

A library of nanoparticles that displayed polyglutamated folate ligands at high and low valency was generated. Members of this library were tested first for PSMA binding in vitro. Then, the most optimal members of the nanoparticle library were further developed for in vivo delivery of a PET tracer and an antiandrogenic drug. The following experiments were conducted:

Experiment 1. Creation and Screening of a Library of Multivalent HBPE Nanoparticles to Target PSMA In one aspect, disclosed are methods used to synthesize a rationally designed library of glutamate- and folate-containing compounds to be conjugated to the surface of HBPE-DFO nanoparticles. As disclosed herein, nanoparticles with these functionalities bind to PSMA-expressing cells. In addition, in vivo studies indicate that these nanoparticle conjugates localize to PSMA-expressing tumor. However, to identify molecules that bind more selectively to PSMA and the nanoparticle's optimal targeting ligand density for optimal binding, a library of ligands containing folic and glutamic acid functionalities in different orientations were designed, with the goal of identifying a particular ligand that specifically bind to PSMA. Furthermore, the effect of the nanoparticle's ligand density on the nanoparticle's PSMA targeting ability toward prostate cancer cell lines was investigated. This was achieved by conjugating the ligands at different densities, creating high valency (HV) and low valency (LV) ligand-nanoparticle conjugates A ligand which contained both folic and glutamic acid functionalities, when displayed on an HBPE nanoparticle, resulted in a more selective PSMA-targeting nanoparticle.

Ligand Library Synthesis

To facilitate direct linking of the target molecules to propargylated HBPE nanoparticles via Huisgen-Sharpless's click chemistry, an azide-functionalized library of compounds was generated. The targeted collection comprised four scaffolds. Scaffold 1 was represented by a gamma/alpha substituted polyglutamic folate moiety, which mimicked the endogenous ligand for PSMA. The number of glutamate units (0-5) was systematically varied to optimize the length of the ligand for binding. In addition, the polyglutamic unit was made with D-ammo acids to prevent cleavage by PSMA due to the enzyme's inherent glutamate-carboxylase and hydrolase activity (FIG. 11). The gamma-substituted derivatives were synthesized from D-polyglutamates and folic acid using gamma-selective peptide coupling conditions, while the alpha-substituted analogs were accessed through a similar peptide coupling with a gamma-protected folate derivative.

Figure 12:
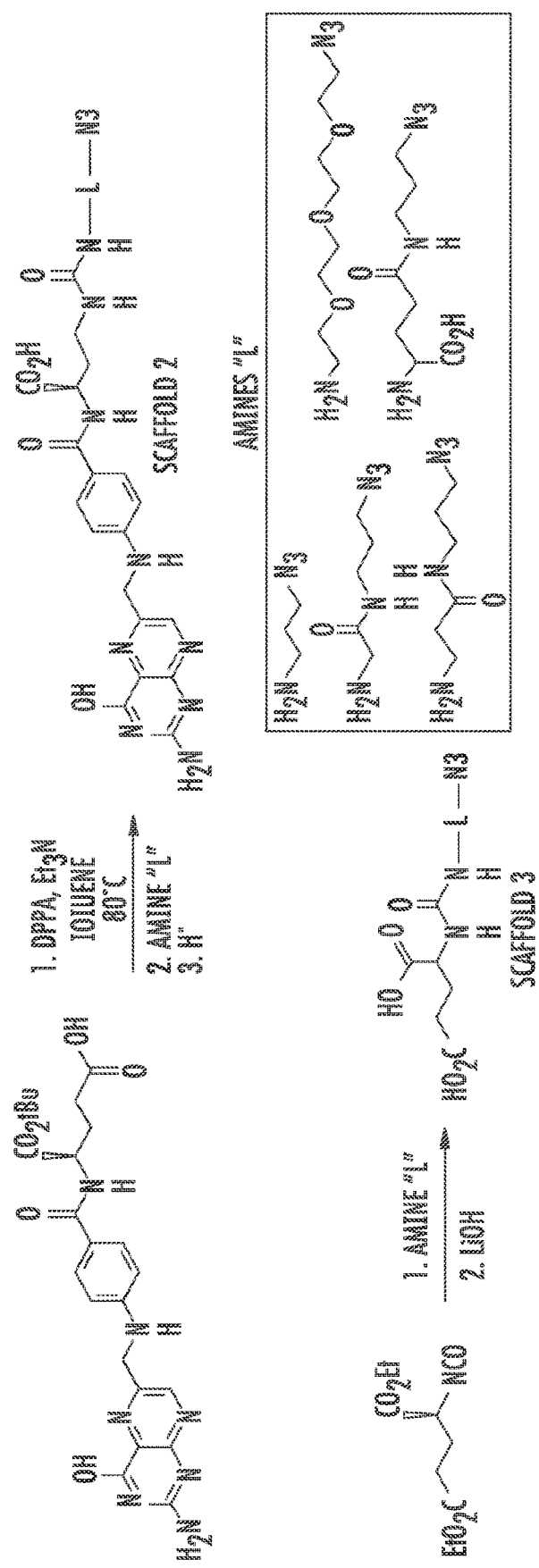
FIG. 12 depicts the general synthetic scheme toward Scaffold 2-3 analogs.
Figure 3:
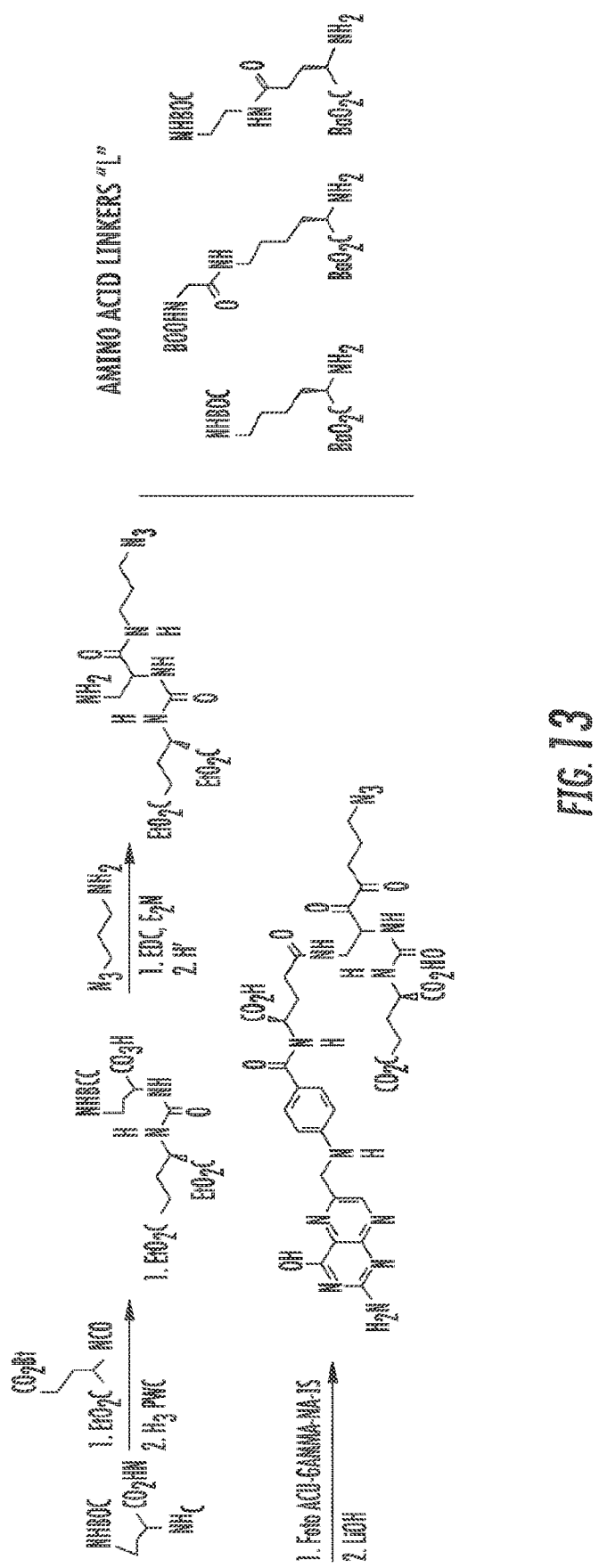

Scaffolds 2 and 3 comprised either folate or glutamate azido urea derived compounds, respectively (FIG. 12). Azido urea glutamates have been reported as highly specific PSMA binding inhibitors; however, their conjugation to nanoparticles for targeting PSMA has not been studied in detail. The effect of ligand length and hydrophobicity were systematically probed herein by using various amino alkyl azides in both the folate and glutamate azido urea scaffold sub-classes. The creation of azido urea folate compounds and their use as PSMA inhibitors/targeting ligands has never been reported. The scaffold 2 library was readily accessible by reaction of the appropriate alkylazido amines with the isocyano folate, formed via a Curtius rearrangement of a protected folic acid derivative. Similarly, protected glutamic acid derivatives were converted to the corresponding isocyanides via a Curtius rearrangement, which then formed the scaffold 3-based series upon treatment with the alkylazido amines. This method provided ready access to these libraries; however, if there are complications with the synthesis, then replacing the urea moiety with an amide bond allows the use of standard peptide coupling chemistry as in scaffold 1.

Scaffold 4 comprised various bi-functional glutamate-folate hybridized compounds. The proposed 3 analogs within this category are represented in FIG. 13. While examples of the type of ligands synthesized in this library are provided, it is also recognized that the experience and data obtained making and testing members of the previous categories resulted in identifying the optimal features in terms of length and hydrophobicity of the ligand spacer. This approach inherently defined the ideal way to simultaneously present both the folic and glutamic acid functionalities on the same binding ligand. Thus, data obtained during the course of the program resulted in the creation of ligands slightly different from the ones represented in scaffold 4. Scaffold 4-based analogs were synthesized using similar methodology as described for the previous scaffolds. Protected amino acid derivatives were sequentially functionalized with glutamate, folate and aminoazide moieties using both peptide coupling and Curtius rearrangement reactions. These methods provided a highly flexible route to a variety of bi-functional glutamate folate hybrids. These analogs, and all the previously described scaffold analogs, were accessible on 20-50 mg scale and the purity and identity of each compound was determined by NMR, and HPLC/UV/MS analyses. All analogs prepared were >98% purity and fully characterized. Additionally, the synthesis of specific analogs of interest on a larger scale was achievable using these routes.

High Valency (H) and Low Valency (LF) Nanoparticle Systems

To increase the aqueous solubility of the final HBPE nanoparticle conjugates, the nanoparticle's carboxylic acid groups were first functionalized with polyethylene glycol (PEG). Introduction of PEG onto the nanoparticles also facilitated reduction of non-specific protein binding, facilitating longer blood circulation time and therefore minimizing liver uptake during animal studies. HBPE (DiI) nanoparticles were used in these experiments. The fluorescent dye DiI was encapsulated into the nanoparticles to facilitate cell culture screening.

To conjugate PEG onto the nanoparticles, polyoxyethylene diamine (diamino PEG, $M_w$=3350, 10 mmol) in PBS buffer (pH=7.4) was added to a suspension of HBPE nanoparticles using conventional water-soluble EDC/NHS (10 mmol, MES buffer pH=6.0) carbodiimide chemistry. The final reaction mixture was purified using PD-10 column, before quantification of the number of amino groups on the nanoparticle's surface using standard SPDP method. The overall change in surface charge (zeta potential measured using Malvern's zetasizer instrument) further confirmed the successful conjugation of diamino PEG. Next, the resulting pegylated HBPE(DiI) nanoparticles were conjugated with 4-pentynoic acid (10 mmol in DMSO) using carbodiimide chemistry. Briefly, a mixture of EDC and NHS (10 mmol, MES buffer pH=6.0) was added to the solution of 4-pentynoic acid, before incubation with the pegylated HBPE (DiI) nanoparticles ($6 \times 10^{-3}$ mmol in PBS buffer, pH=7.4) for 3 h at room temperature. The final reaction mixture was purified using a PD-10 column, before assessing the number of propargyl groups on the nanoparticle's surface. The resulting propargylated and pegylated HBPE(DiI) nanoparticles ($6 \times 10^{-3}$ mmol) were conjugated to the corresponding members of the azide derivatized compound libraries 1, 2,and 3 via "click" chemistry in 0.1 M bicarbonate buffer, pH 8.5, containing a catalytic amount of CuI (0.01 mmol) in bicarbonate buffer as described. To this solution, an azide-functionalized small molecule (10 mmol in DMSO) was added and incubated overnight at 25° C. The conjugated HBPE nanoparticles were then purified by dialysis and PD-10 column to get rid of the click chemistry reagents, particularly $Cu^+$, and characterized by particle size analysis, SEM and ICP-MS. Successful ligand conjugation was assessed by UV and FT-IR measurements. Samples were stored at 4° C.

The average number of ligands bound to the HBPE nanoparticle was controlled by varying the ligand's stoichiometry resulting in HV and LV nanoparticles as described herein. Nanoparticles were categorized as HV when the number of ligands per nanoparticle was around 100±20, while a LV was one that had 10±5 ligands per nanoparticle. Briefly, for the HV preparation, a 10× higher amount of the azide functionalized small molecule ligands was used as opposed to the LV preparation (1×) The proper ratio to guarantee a suitable difference in ligand loading (HV vs. LV) was determined experimentally. Confirmation of the successful HV- vs. LV-conjugation of small molecule ligands was assessed by UV-Vis and fluorescence emission. As members of the rationally designed library contained folic acid, the assessment of ligand density on the nanoparticle by these spectrophotometric methods was not a problem. The size and degree of pol dispersity of the resulting HBPE nanoparticle conjugates were characterized by STEM and DLS HBPE, HBPE-PEG and HBPE-PEG-Folate nanoparticles were incubated with FBS to estimate the amount of nonspecific protein binding by measuring the increase in nanoparticle size by DLS after a 24-h incubation period. Results showed no detectable increase in size of the HBPE-PEG or HBPE-PEG-Folate, whereas the HBPE nanoparticles had an increase of 20 nm in size, due to non-specific protein absorption. These results indicated that the presence of folate did not interfere with the ability of PEG to prevent non-specific protein absorption.

Cell Culture Screening

The ability of various members of the HBPE nanoparticle (HV and LV) to bind and internalize into PSMA(+) cells was assessed by confocal microscopy and FACS studies. For these studies, a panel of culture cells that express different levels of PSMA and FR were used. These studies assessed the specificity of the HV and LV ligand functionalized HBPE nanoparticles toward PSMA. As positive control. HBPE nanoparticles conjugated with anti-PSMA antibodies or PSMA aptamers were tested and results were compared to those obtained with the HV and LV polyglutamated folate nanoparticles. All cell lines were obtained from ATCC, except the PSMA(+) PC3 cells, which were obtained from MSKCC. All cells were maintained in accordance to the supplier's protocols in a humidified incubator at 37° C., under 5% $CO_2$ atmosphere.

Confocal Laser-Scanning Microscopy

Cells were grown overnight on culture dishes, before treatment. After incubation with the nanoparticles, the cells were washed three times with 1×PBS, fixed with 5% formalin solution, stained with DAPI (Molecular Probes) for nuclear visualization and finally examined for nanoparticle internalization using a Zeiss LSM 510 confocal microscope equipped with a 40× objective.

Flow Cytometry

Treated cells were detached and centrifuged at 1000 rpm before collecting, washing and suspending the cell pellets in 1×PBS. The resulting cellular suspensions were examined using a FACSCalibur flow cytometer (BD Biosciences). The specificity of the nanoparticle internalization via PSMA was assessed by studies using PMPA, a PSMA inhibitor.

Characterization and Testing

All small molecules and intermediates synthesized were characterized by using common spectroscopic techniques, FTIR, $^1H$ and $^{13}C$ NMR. HPLC and mass spectroscopy. The nanoparticle conjugates were characterized using UV-Vis and fluorescence spectroscopic analyses. Size of the conjugated nanoparticles was measured using a Precision detectors Dynamic Light Scattering (PD2000 DLSplus) system and by STEM. A successful preparation had its size nearly unchanged from the starting preparation and was stable in aqueous buffers.

Data Analysis and Alternatives

The synthetic routes chosen for the syntheses of scaffolds 1-4 were robust and precedented with no complications beyond the standard optimization of reaction conditions (time, temperature, solvent, reagent stoichiometry). If unexpected complications arise, the chosen routes contain sufficient flexibility for altering the sequence of reactions along the synthetic route. Additionally, the click chemistry used to attach the small molecule library to the nanoparticles would work equally as well if synthetic considerations required that the azide and alkyne moieties to be transposed between substrates. Alternatively, recently developed click chemistry reactions that do not involve the use of Cu catalysis can be used in the case that Cu presents a toxicity problem during animal studies. However, this is not a problem as the nanoparticles disclosed herein do not bind Cu nonspecifically. ICP-MS characterization of the nanoparticles was performed to verify the absence of Cu in the final nanoparticle formulation. The above nanoparticle experiments resulted in data on optimized reaction conditions (e.g. ratio of nanoparticle to conjugation reagents, incubation times, temperature, etc.). Data was tabulated and the most optimal conjugation procedures that result in stable nanoparticle conjugates were chosen for subsequent studies. Only preparations with reproducible syntheses and monodisperse particle size distributions were used for subsequent experiments.

Statistical Analysis

All optimization experiments were conducted in triplicate. Appropriate controls were always included. Means, standard deviations, and graphics were the primary tools to summarize the data. Correlations were performed using the Spearman method. Two-way ANOVA method was used to compare the differences among different agents and to compare among different time points within each treatment with a statistically significant difference defined as a P value of less than 0.05.

Experiment 2. Synthesize of $^{89}$Zr-DFO Grafted Theranostic HBPE Nanoparticles to Target PSMA In one aspect, disclosed are procedures for the fabrication of a Zr-chelating DFO-grafted HBPE nanoparticle. The developed protocol for the synthesis of a DFO-grafted HBPE nanoparticle and the subsequent fabrication of a Zr:DFO-grafted HBPE nanoparticles have been reproducible, yielding a monodispersed nanoparticle preparation of 76±4 nm (FIGS. 9A-9B). In this experiment, the synthetic procedure for the DFO-HBPE nanoparticles and the encapsulation protocol for abiraterone and MDV-3100 were optimized. Furthermore, the incorporation of $^{89}$Zr was optimized for potential tracking of the nanoparticle using PET imaging. A DFO-grafted HBPE nanoparticle chelates $^{89}$Zr as well as encapsulates an antiandrogenic drug (abiraterone or MDV-100) resulting in a theranostic nanoparticle for the treatment of PCa.

Synthesis, Characterization and Optimization of $^{89}$Zr:DFO-Grafted HBPE Nanoparticles In this experiment, the ability of the nanoparticles to chelate $^{89}$Zr was studied, with the goal of fabricating a stable and reproducible preparation of $^{89}$Zr-DFO-grafted HBPE nanoparticle. The radioactive $^{89}$Zr was generated and supplied MSKCC. Briefly, zirconium-89 was produced by a (p,n) reaction on natural yttrium-89. A variable-beam energy cyclotron (Ebco Industries Inc., BC, Canada) was used to bombard $^{89}$Y, resulting in the displacement of a neutron by a proton, and thus creating $^{89}$Zr. The $Fe^{3+}$:DFO-grafted HBPE nanoparticles were prepared using the solvent diffusion method as described above. This was accomplished by preparing a DMF (40 µL) solution of Fe-DFO-HBPE (50 mg) and adding it drop-wise (10 µL/drop) to nanopure water (700 µL) with continuous stirring at room temperature. The synthesized nanoparticles were purified via dialysis (MWCO 6-8K) against water Next, optimization experiments were performed to determine the most optimal level of encapsulation for abiraterone and MDV-3100. In preliminary studies, encapsulation efficiency was found for abiraterone of 75% in the HBPE nanoparticles. This was achieved by encapsulating I mg of the drug into Fe-DFO-HBPE (50 mg) nanoparticles in suspension. The amount of drug (1-5 mg) was systematically varied in order to achieve a maximum of drug encapsulation without compromising nanoparticle stability. All nanoparticle preparations were characterized by DLS, STEM and ICP-MS to access the amount of incorporated iron. In addition, the encapsulation efficiency (EE %) and rate of drug release in vitro were assessed. In separate experiments, stability tests of the nanoparticle preparations after incubation in serum (FBS) supplemented buffers were performed by measuring the amount of drug release and increase in particle size (due to swelling or serum protein binding) upon incubation. All three nanoparticle preparations (1) abiraterone-, (2) MDV-3100- and (3) empty $Fe^{3+}$:DFO-grafted HBPE nanoparticles were then tested for exchange with radioactive $^{89}$Zr. The Fe chelated by DFO within the nanoparticle was displaced by $^{89}$Zr as described. In order to remove the iron, an excess EDTA solution was added to the HBPE-DFO-Fe and incubated for 30 min at pH 4.5. Subsequently, after the transchelation was complete, the HBPE-DFO was purified by PD-10 size exclusion chromatography. $^{89}$Zr, in an oxalic acid solution adjusted to pH 7.7-8.5, was then added to the purified HBPE-DFO and the reaction was incubated at room temperature for 1-2 h. After the reaction was complete the HBPE-DFO-$^{89}$Zr was also purified with a PD-10 column (GE Healthcare).

The above experiments resulted in data on optimized reaction conditions (e.g. ratio of metal (Fe, Zr) to DFO-grafted polymers and nanoparticles, amount of drug loaded, incubation times, temperature) Data was tabulated and the most ideal conditions and optimal ratios were chosen for subsequent studies. Optimized synthesis was scaled up and complete records of all batch synthesis were kept. Only preparations with reproducible syntheses and particle characteristics were used for subsequent experiments. While abiraterone and MDV-3100 were chosen as drugs to be encapsulated, a variety of other drugs can be employed if difficulties with this choice were encountered. Some alternatives include taxol and doxorubicin. All optimization experiments were conducted at least in triplicate. Appropriate controls were always included.

Statistical Analysis was Performed as Described in Experiment 1

Experiment 3. In Vivo Assessment of Lead Members of the Nanoparticles in Animal Models of Prostate Cancer In this experiment, the expected clinical value of the $^{89}$Zr-DFO grafted HBPE nanoparticles was evaluated. Their ability to target PCa and to detect bone tumors as a model for bone metastases in a mouse model was determined. PET imaging allowed quantification not only of the PSMA expression but it also allowed the delivery efficacy of the nanoparticle to the tumor to be judged in the second step. The binding (via Standard Uptake Value [SUV] in PET) was correlated with the amount of PSMA expressed in the tumors. The therapeutic efficacy of PCa drugs were increased by encapsulation in $^{89}$Zr-DFO grafted HBPE nanoparticles while at the same time allowing monitoring of the drug distribution by PET.

Targeting Subcutaneously Implanted PCa Cells in Mice

The lead members of the multivalent PSMA targeting nanoparticles were tested in vivo with male SCID SHO mice, each bearing a PSMA-positive PC3 tumor on one flank, a PC3 wild-type tumor on the other and a LNCaP tumor on the back. This provided a spectrum of PSMA expression to evaluate the in vivo specificity of the HBPE nanoagent as the PSMA expression is higher in the transfected cell line. First, a biodistribution study was performed to obtain information on the tumor uptake of the nanoparticles. To this end, ca. 20 µCi of $^{89}$Zr-DFO grafted HBPE nanoparticles conjugated to the lead PSMA targeting ligands were injected into a cohort of mice (n=3 per time point, tail-vein injection) and the tumors and organs 6, 12, 24, 48, 72 and 96 h were harvested after injection. The time point for the following in vivo imaging studies was based on the biodistribution data. For PET imaging (Focus 120, CTI/Siemens, Knoxville, TN), standard uptake values (SUV) were determined for the PSMA-positive and -negative tumors. For optical tomography (FMT2500, VisenMedical, Bedford, MA) the concentration of the nanoparticles were measured after prior calibration of the system with the nanoparticles. Co-registration of PET and FMT was performed using a specialized imaging cassette that fits into the FMT as well as onto the PET scanner with minimal attenuation and included fiducial markers (Visen). Dose finding studies were performed to obtain the minimal required dose for imaging, expected to be at around 125 µCi. The tumors were harvested for immunohistochemistry to detect PSMA and to confirm co-localization of the probe via fluorescent microscopy and autoradiography. Western blot analysis was used to quantify the amount of PSMA and for correlation with the imaging data. Based upon the specific activity of the nanoparticles, the amount of nanoparticles within the tumors was estimated. To assess the specific binding of the nanoparticles to PSMA, the following controls were used: (1) HBPE nanoparticle without targeting ligand, (2) PMPA, as a known inhibitor of PSMA, was co-injected with the nanoparticles and (3) excess (non-conjugated) small molecule ligands were co-injected with the nanoparticles as blocking experiments. In all these controls, the nanoparticles did not bind to the PSMA bearing tumors and the degree of non-specific binding was assessed. In addition, control experiments using HBPE nanoparticles conjugated with anti PSMA antibodies or PSMA aptamers were tested in vivo and results were compared to those obtained with poly glutamated folate nanoparticles.

Targeting Bone Tumors as a Model of Bone Metastasis in Mice

Next, the capabilities of the probes to detect tumors seeded to the bone as a model of cancer metastases were explored. To create bone tumors, the tibiae of mice were exposed and a small hole was drilled through the cortex into the marrow space using a stero-microscope. Once the cavity was accessed, concentrated PSMA (+) PC3 cells in medium were slowly injected until backflow was observed. After flushing of the side to remove back-flushed cells, the drill hole was closed with bone wax and the skin was closed with sutures to avoid artifacts from metallic staples on imaging. The mice (n=5) were followed weekly via MR-imaging to detect developing bone tumors. Once tumors were detected, the mice were injected with the corresponding nanoagent as described herein and imaged with PET and FMT. The mice were sacrificed and the number and mean-size of metastases were correlated with the read out obtained by imaging as described herein. Controls comprised mice carrying PSMA (−) PC3 tumors and mice bearing PSMA-positive tumors but injected with control non-targeted HBPE nanoparticles.

In the event that significant uptake with PET is not measured, the excised tumors can be measured in a well counter, which is more sensitive than PET imaging. If activity is detected with the counter (but not with PET), the $^{89}$Zr labeling efficacy can be increased by increasing the ratio of $^{89}$Zr to DFO-grafted HBPE nanoparticles, enabling more $^{89}$Zr to be chelated Additionally, the dose of nanoparticles injected can be increased. For subcutaneous tumors, optical imaging of the animals can be conducted after injecting a higher dose of particles to rule out in vivo de-chelation of the $^{89}$Zr, in which case a PET signal will not be acquired but the particles can be detected with FMT as described herein.

The ability of the nanoparticles to carry a therapeutic payload directly to the targeted tumor was determined and the therapeutic efficacy was compared with therapy with the free drug. The theranostic HBPE utilized to improve the delivery of an anti-androgenic (abiraterone or MDV-3100) therapy was studied. Again, the lead nanoparticle preparations were used. It was first tested in vitro if cell death can be obtained using the same cell lines as in the previous experiments by incubating the cells with the theranostic nanoparticles either 24, 48 or 72 h at 3 different concentrations. LNCaP cells were treated with a total concentration of abiraterone (0.1, 1 and 10 mM dissolved in 10 µL DMSO; Sigma Aldrich) or MDV-3100 (10, 100 or 500 nM: Medivation, San Francisco, CA) As control LNCaP cells were also treated with either vehicle (DMSO), empty HBPE nanoparticles (i.e. without the drug as payload) or the drug delivered freely at the same dosage (i.e. without HBPE) only. For the anti-androgen therapy, PC3-PSMA+ cells were used as controls since PC3 cells lack the androgen receptor. PC3 wild type and LNCaP-PSMA knock out cells were also utilized as control, both without PSMA expression. To these cells, the HBPE nanoparticles were not targeted specifically due to the lack of PSMA. The amount of nanoparticles taken up into the cells and the proportion of dead or dying cells, respectively, were determined via FACS for all groups (using 7AAD as a marker of apoptosis). Additionally, fluorescence microscopy of the nanoparticle treated cells was performed. The percentage of apoptotic cells in each group was compared. In vivo studies were conducted subsequent to the in vitro studies. To this end, groups of mice with both LNCaP wild type and LNCaP-PSMA-negative tumors on each flank were used. The mice (n=5 per group) were treated with either HBPE/abiraterone or HBPE/MDV-3100 nanoparticles on 3 consecutive days. Three different dosages were tested: 0.1, 0.5 or 1.0 mmol/kg abiraterone and 10, 25 or 50 mg/kg MDV-3100 injected iv on 3 consecutive days as described. Control mice received empty (HBPE alone) vehicle or the free drugs at the same dosage without nanoparticle carrier. Tumor growth was monitored by measuring the tumor size. At the same time, combined optical and PET imaging was performed to monitor the targeting of the nanoparticles to the tumors as described herein. Imaging was performed 24 h after the first and the last dose; and SUV values were obtained from the tumors. No imaging was performed in mice not receiving particle preparations. In addition, blood was collected for weekly PSA measurements (with a commercially available ELISA), using the value prior to therapy as a baseline. The tumors were followed for 6 weeks or until reaching 1.5 cm in size (whichever comes first). The tumors were harvested for immunohistochemistry (using J591 to identify PSMA) and also qrt-PCR and quantitative Western Blot for PSMA levels in the tumor to correlate with response to the targeted therapy. The study was repeated with the best dosing, using lung colonies as described herein. The size, weight, and growth dynamic of the tumors were correlated where applicable with the SUV value (indicating the amount of targeting HBPE nanoparticle) as well as with the dose of the drug applied with the particles, the amount of PSMA within the tumors and the serum PSA values.

With the completion of the third experiment, the following were observed: (1) one of the lead polyglutamated folate HBPE nanoparticles delivers therapy via targeting, (2) the therapy delivery was improved over its conventional form, and (3) the therapy efficacy of the nanoparticles were established for 2 different drugs.

In the unlikely event that there is no response to the therapy, either in vitro or in vivo, is observed with the chosen doses, the dose can be increased gradually. If the dose is too high (i.e. toxic), less dose can be given over more days. If this does not result in the expected effect, go back to the library and utilize the second best carrier with the expectation that it will fare better in mo. An increase of PSMA expression upon androgen deprivation has been documented in the literature. It is, therefore, possible that increased binding efficacy of the nanoparticles can be observed after the last dose of therapy. If this is the case, this effect can be utilized by first treating with antiandrogens to increase the PSMA expression, followed by HBPE/etoposite nanoparticles.

For an expected difference in means of at least 75% and a power of 95%, a sample size of 3 was calculated. To account for biological variability, a sample size of n=5 mice per group were used for all in vivo experiments. All in vitro experiments were done in triplicate, and in vivo experiments were repeated for reproducibility. Help with all statistical analysis were obtained from the Biostatistics Core of MSKCC. Support from this core included the determination of overall experimental designs, hypothesis generation, interim analysis, data management, power, quality control of research data, and final statistical analysis. Analyses of data were descriptive in nature. Means, standard deviations, and graphics were the primary tools to summarize the resulting data. Correlation was performed using the Spearman correlation method. Two-way ANOVA method was also used to compare the differences among of different agents and to

Example 2

Therapeutic peptides, with cancer cell specific activity, are a promising treatment option for mCRPC. CT20p, a mitotoxic peptide, disclosed herein, targets cancer-specific differences in mitochondrial physiology. CT20p is a promising anti-metastatic agent because it causes detachment-induced cell death; however, to develop the clinical use of CT20p for mCRPC, there are challenges that need to be met, such as low stability in serum Disclosed herein is a targeted molecular nanotheranostic (dual therapy and diagnostic) platform that delivers CT20p in high concentrations to PCa and has the capacity for imaging peptide efficacy in murine models of PCa. To deliver CT20p to PCa, the peptide was encapsulated within hyperbranched polyester nanoparticles (HBPE-NPs) that were functionalized with polyglutamated folates, the natural ligand for a PCa-specific cell surface protein, PSMA. PSMA is highly expressed in PCa tumors and metastatic lesions but not normal prostate. To endow the NPs with imaging capabilities, the polymer was modified to graft desferrioxamine (DFO), a chelating ligand for stable encapsulation of a $^{89}$Zr-PET imaging probe. PSMA-targeted HBPE[CT20p]NPs, co-encapsulated with $^{89}$Zr, yield a powerful therapeutic platform to reduce PCa growth and metastatic spread, while enabling assessment of particle biodistribution. In one aspect, disclosed are methods for the synthesis of HBPE-DFO[CT20p]-NPs, in which the HBPE-DFO[CT20p]-NPs was optimized to obtain effective chelation of $^{89}$Zr, pegylation and CT20p loading (Experiment 1). In another aspect, a series of polyglutamated folate-HBPE-DFO[CT20p]-NPs were synthesized and tested to target PCa cells via PSMA (Experiment 2). PET imaging, using murine models of PCa, was used to assess delivery and efficacy of CT20p and pharmacokinetics. The clinical value of the HBPE-DFO[CT20p]-NPs disclosed herein was investigated in murine models of PCa, using mice that were intact or castrated, and in models of lymph node and bone metastasis (Experiment 3). PSMA-targeted, HBPE-DFO[CT20p]-NPs (without $^{89}$Zr) can be directly used for the treatment of mCRPC without the side effects associated with current therapies, while the theranostic version (with $^{89}$Zr) provides the pre-clinical data to advance the use of PET imaging for monitoring fast growing prostate tumors and treatment outcomes.

A targeted, multifunctional nanoparticle platform incorporating a therapeutic peptide is disclosed herein as a treatment approach for castration resistant prostate cancer and metastatic disease. The approach involves engineering the nanoparticle platform to encapsulate the therapeutic peptide and chelate $^{89}$Zr for dual treatment and PET imaging in prostate cancer mouse models. Positive outcomes were measured in the capacity to monitor the disease-specific accumulation of nanoparticles in tumors and stimulate tumor regression.

Prostate cancer (PCa) is a leading cause of cancer deaths in men. Current therapies, such as androgen deprivation treatment (ADT), are initially effective but have severe side effects, including impotence and incontinence. Over time, nearly all men develop progressive disease or castration-resistant prostate cancer (CRPC), which has a poor prognosis, especially if the cancer has spread. CRPC patients with bone metastasis have survival rates of less than 2 years and most treatment approaches for metastatic CRPC only extend life by a few months. Hence there is a need for more effective anti-metastatic CRPC therapies. Peptides therapeutics, specifically those designed to impair mitochondrial energy-providing functions, are promising treatment options for metastatic disease that significantly improve the quality of life and survival of patients with CRPC. Recently. CT20p, a mitotoxic peptide that targets cancer-specific differences in mitochondrial physiology, disrupting cell adhesion and causing detachment-induced cell death was discovered. CT20p has the potential to impede cancer cell invasiveness, making the peptide a promising agent for inhibiting metastasis. However, in order to develop the clinical use of CT20p for life-threatening cancers like CRPC, there are challenges that need to be met, including low stability of the peptide in serum, degradation by proteases, and lack of peptide monitoring during pre-clinical bio-distribution studies. New platform technologies that allow for the concentration and monitoring of therapeutic peptides to areas of disease are urgently needed. Nanoparticle (NP) based technologies are effective, because nanoparticles (NPs) stably incorporate and protect peptides, like CT20p, from proteases, while enhancing cellular uptake via the use of targeting ligands. While the hydrophobic nature of CT20p limits its direct use in cell culture and animal studies, this facilitates the encapsulation of the peptide in hyperbranched polyester NPs (HBPE-NPs) that can also incorporate imaging agents within the polymer matrix. Such NP formulations allow for the monitoring of particle biodistribution, using highly sensitive imaging technologies such as PET (positron emission tomography), and have the potential of translational use as a non-invasive method for monitoring patient outcomes. In addition, the optimization of ligands on the surface of HBPE-NPs increases targeting of NPs, improving concentration in tumors and metastatic sites bearing targeted receptors. With the goal of developing a platform technology for the delivery and monitoring of a therapeutic peptide for the treatment of CRPC, second generation HBPE NPs were fabricated that incorporate CT20p and $^{89}$Zr for assessment by PET imaging. In preliminary studies, HBPE[CT20p]NPs caused PCa tumor regression in treated mice with no detectable toxicity to normal tissue. Targeted HBPE[CT20p]NPs, co-encapsulated with $^{89}$Zr, yielded a robust therapeutic platform to reduce PCa growth and metastatic spread, while enabling assessment of particle biodistribution. To this end, the hyperbranched polymer was grafted with desferrioxamine (DFO), a ligand that chelates $^{89}$Zr, a long-lived positron emitting radioisotope (half-live of 3 days). To target PCa cells, the prostate specific membrane antigen (PSMA), a membrane-bound receptor that correlates with the severity of PCa and is expressed in metastatic lesions but not normal cells was utilized. In preliminary results, PSMA was an effective targeting receptor. A systematic optimization of the NP preparation was performed to facilitate the incorporation of $^{89}$Zr within the NPs nanocavities and to optimize CT20p loading. To enhance ligand presentation on the HPBE (CT20p)NPs for targeting to PSMA, a series of polyglutamated folate peptides, since polyglutamate folate is a natural ligand for PSMA, were conjugated onto the NPs. The following experiments were designed to develop the best HBPE-NP conjugates for targeted imaging and peptide delivery to treat PCa.

Experiment 1. Synthesis and Optimization of HBPE-DFO[CT20p]-NPs

Figure 17A:
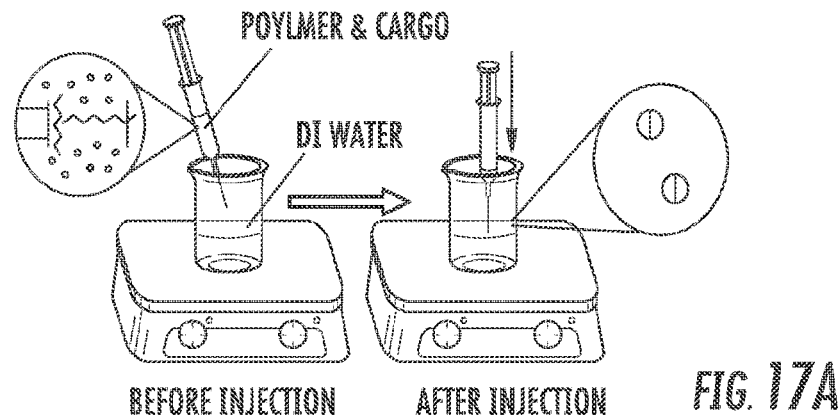
FIG. 17A depicts a solvent diffusion method used to fabricate the folate-HBPE-DFO(CT20p)-NPs. The polymer and CT20p were dissolved in a water-miscible beaker containing water under constant stirring.
Figure 17B:
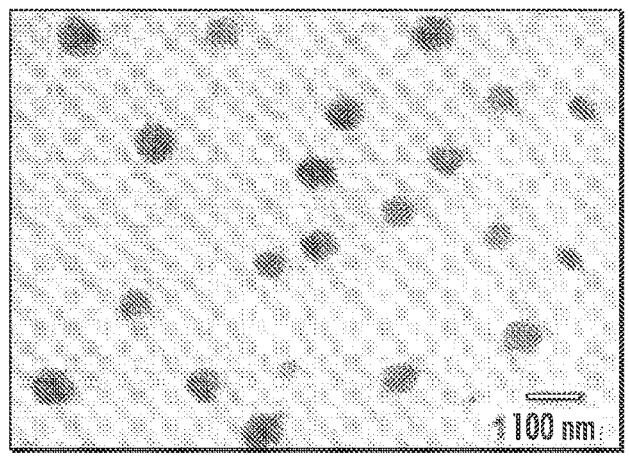
FIG. 17B is a representative STEM image of NPs.

The developed protocol for the synthesis of a Fe(III)-DFO-grafted HBPE-NPs encapsulating CT20p is highly reproducible, yielding monodispersed NP preparations that average 80 nm in size (FIG. 17B). Recent reports indicated that a NP size of less than a 100 nm in diameter is the most optimal for PCa tumor targeting using PLGA/PLA polymeric NPs. However, other parameters such as amount of PEG on the NP's surface, surface charge (zeta potential) and ligand density play a key role in the stability, targeting ability and pharmacokinetics of the NP formulation. The polymeric NP synthesis protocol was optimized taking into consideration these parameters. Furthermore, the encapsulation of the mitotoxic peptide, CT20p, was optimized and $^{89}$Zr for bio-distribution studies using PET (Experiment 2) was incorporated. It was determined that a stable and monodispersed DFO-grafted HBPE-NP formulation that is optimally PEGylated can be developed with the ability of encapsulating CT20p and chelating $^{89}$Zr. The grafting of DFO was optimized to obtain effective chelation of $^{89}$Zr without compromising PEGylation, CT20p loading, NPs stability, particle size, or polydispersity. In vitro peptide stability and toxicity studies were also performed.

Optimization q/PEG Conjugation on HBPE NPs

A 12 carbon PEG (carboxy-PEG12-amine) was used to modify the HBPE-NPs herein, and it was established herein that pegylation did not reduce cellular uptake of HBPE-NPs loaded with DiR (by flow cytometry). In this experiment, PEG length was optimized by conjugating carboxy-$PEG_n$-anine of different lengths (n=12, 24, 48, etc.) and the stability of the NPs was assessed in buffer and in serum. To conjugate the PEG molecules onto the NPs, carboxy-$PEG_n$-amine (Thermo, 10 mmol) in PBS buffer was added to the DFO-HBPE-NPs using conventional water-soluble EDC/NHS (10 mmol, MES buffer pH=6.0) carbodiimide chemistry. Folic acid was conjugated to some of these NPs for use as controls in Experiment 2 The final reaction mixture was purified using a PD-10 column. All NP preparations were characterized by DLS, STEM and FTIR to access their polydispersity, and degree of PEG conjugation. Stability tests of the NP preparations after incubation in serum (FBS) supplemented buffers were performed by measuring the increase in particle size (swelling due to binding of serum proteins) In addition, binding studies with PCa cells (Table 1) were performed to determine how the different PEG units affect the binding of NPs to cells. The most optimal PEG-modified NP preparations were those that resulted in minimal serum protein adsorption, enhanced binding to PSMA (+) cells and improved circulation in vivo (See Experiment 2: PK studies).

Optimization of 89Zr:DFO Grafted (C20p) HBPE NPs

The ability of the NPs to chelate $^{89}$Zr was optimized in order to fabricate stable and reproducible preparations of $^{89}$Zr-DFO-grafted (CT20p) HBPE-NPs. Radioactive $^{89}$Zr was generated and tested at the MSKCC (see Letter of Support). Briefly, zirconium-89 was produced by a (p,n) reaction on natural yttrium-89. A variable-beam energy cyclotron (Ebco Industries Inc., BC, Canada) was used to bombard 89Y, resulting in the displacement of a neutron by a proton, and thus creating $^{89}$Zr. The $Fe^{34+}$:DFO-grafted (CT20p) HBPE-NPs, in which Fe was replaced by Zr, were prepared using the solvent diffusion method as explained herein. A DMF (40 mL) solution of Fe-DFO-HBPE (50 mg) was prepared, adding it drop-wise to nanopure water (700 mL). CT20p (Ac-VTIFVAGVLTASLTIWKKMG-$NH_2$) (SEQ ID. NO. 7) and two control peptides with irrelevant sequences were commercially synthesized at >98% purity (Biopeptide Inc). Peptides were added to the solution as described herein. The synthesized NPs were purified via dialysis (MWCO 6-8K) against water. Immediately before the murine PET studies (Experiment 2), the Fe chelated by DFO within the NP was displaced by $^{89}$Zr as described herein. In order to remove the iron, an excess EDTA solution was added to the HBPE(CT20p)-DFO-Fe. Subsequently, after the transchelation was complete, the HBPE(CT20p)-DFO was purified by PD-10 size exclusion chromatography. $^{89}$Zr, in an oxalic acid solution, was then added to the purified HBPE(CT20p)DFO. After the reaction was complete, the HBPE(CT20p)-DF0-$^{89}$Zr was also purified with a PD-10 column (GE Healthcare). The $^{89}$Zr labeling efficiency of the Fe(III)-DFO-HBPE(CT20p) NPs was accessed by Instant Thin Layer Chromatography (ITLC) and PET b. The stability of encapsulation of the peptides in all NP preparations was assessed by measuring the rate of release in buffer at physiological pH (~pH 7.4) or at acidic pH (~pH 4-5) using a microdialysis device as performed herein. Only preparations with reproducible synthesis and monodispersed particle size distributions were used for subsequent experiments In Vitro Peptide Stability Assays In order to perform the PK studies in Experiment 2, the profile of CT20p and control peptides, and any fragments that resulted from these, was determined by mass spectrometry (MS). Peptides were analyzed by LC-MRM (liquid chromatography multiple reaction monitoring mass spectrometry) to define assay parameters. Then a fragment ion spectrum was collected using MS/MS and the collision energy was optimized for each fragment. This established the peptide profile. Next, peptides alone or encapsulated in HBPE-NPs, as described herein, were incubated in solutions spiked with mouse and human serum at multiple concentrations (10-10,000 ng/ml), at 4° and 37° C., from 0-48 hours. After incubation, serum proteins were precipitated by methods (e.g. acetonitrile, trichloroacetic acid) that were optimized to ensure maximal peptide recovery. Recovered solutions were analyzed using LC/MS/MS, as described herein, to determine peptide stability in serum alone as compared to encapsulation in HBPE-NPs.

In Vitro Toxicity Studies

Previous reports showed that HBPE-NPs are non-toxic to cells in culture. However, since the HBPE-NPs disclosed herein contain Zr-DFO, toxicity studies were performed using a broad dose range with hepatocytes (HEP10), macrophages (THP-1, RAW 264.7) and fibroblasts (3T3). Cell death was accessed by Sytox (dead cell stain) and apoptosis using the Violet Ratiometric Membrane Asymmetry Probe (Invitrogen) as shown herein. To demonstrate that the cancer cell-specific killing action of the CT20p loaded in PEGylated. DFO-HBPE-NPs or folate-DFO-HBPE-NPs was unchanged, a panel of PCa cells (Table 1) and non-tumorigenic cells (normal prostate epithelial cells, PCS-440-010) were used and cell death was assessed as described herein. Clonogenic assays with a broad dose range were also performed to generate cell survival curves (Rafehi, H., et al., Clonogenic assay: adherent cells. *Journal of visualized experiments: JoVE* (2011)).

The above experiments resulted in data on optimized reaction conditions, degree of PEGylation and non-interference with targeting ligands, peptide loading, DFO-grafted HBPE-NP yields and peptide stability in serum as well as in vitro toxicity. The peptide profile by LC/MS/MS was also determined for PK studies in Experiment 2. Data was tabulated and only preparations with reproducible syntheses, optimal Zr chelation, CT20p loading, peptide and particle stability. PEGylation and minimal off-target toxicity were used for subsequent experiments. The data indicates that functional HBPE-NPs that are inherently non-toxic are generated, however NPs that fail STEM or TEM, have inadequate peptide loading or stability or display toxicity in normal cells are detected and protocols are improved to ensure optimal fabrication. In the event that larger NPs (>200 nms) are obtained, the amount of polymer used is systematically reduced. Likewise, when the amount of encapsulated peptide is low, the amount of cargo is increased. If the NP preparation is unstable in serum or increases in size due to protein binding, longer PEG linkers are used.

Means, standard deviations, tables and graphics were the primary tools used to summarize the data Correlations were performed using the Spearman method. Two-way ANOVA method was used to compare the differences among different agents and to compare among different time points within each treatment with a statistically significant difference defined as a P value of less than 0.05.

Experiment 2. Synthesis and Characterization of a Series of Polyglutamated Folate—HBPE-DFO[CT20p]-NPs to Target PCa Cells Via PSMA Polyglutamated folate peptide derivatives were conjugated to the HBPE-DFO[CT20p]-NPs to enable binding and internalization into PSMA-expressing PCa cells. The best NP conjugate that targets PSMA was identified, using PSMA(+) and (−) PCa cells. Pharmacokinetic (PK) and in vivo toxicity studies were performed along with assessment of bio-distribution of polyglutamated folate-HBPE-$^{89}$Zr-DFO[CT20p]-NPs by PET imaging using murine models of PCa.

Figure 23:
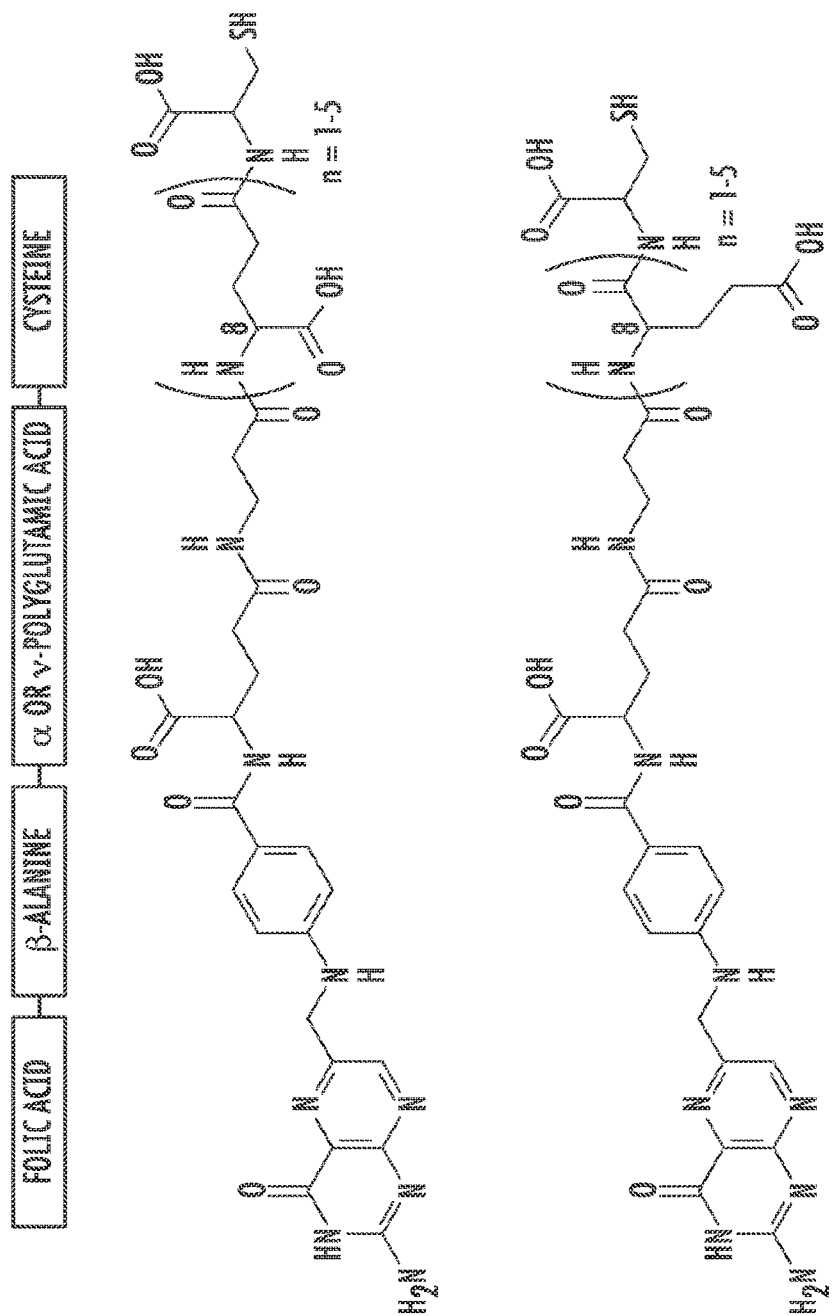
FIG. 23 shows the γ-(top) and α-(bottom) polyglutamated acid folate peptides used herein.

In this experiment, using the disclosed $^{89}$Zr:DFO-HBPE-NPs-encapsulating CT20p (from Experiment 1), targeting capabilities were added in the form of polyglutamated folate ligands. This resulted in a targeted NP formulation to bind PSMA. The approach involved the synthesis of a folate ligand conjugated with various glutamate residues via peptide bonds (FIG. 23). The resulting polyglutamated folate ligands, which are peptides, were synthesized using standard solid phase peptide synthesis procedures with a cysteine residue at the C-terminus to facilitate conjugation to the NPs, using an established protocol (e.g. maleimide, SPDP linkers). The folate was attached via peptide synthesis coupling and Q-alanine was used as a linker between the folate and the polyglutamate chain to minimize hydrolysis due to the folate hydroxylase enzymatic activity of PSMA. The polyglutamic acid peptide was made with D-amino acids, making the ligand more resistant to PSMA glutamate carboxypeptidase activity. As the endogenous substrate of PSMA is a γ-polyglutamated folate, the polyglutamic acid portion of the peptide was synthesized via γ-peptide coupling. As controls, α-polyglutamated folates peptides were generated and tested for binding to PSMA. This generated multiple polyglutamated folate ligands [Folate-(Glu)n-Cys] that conjugated to HBPE-DFO[CT20p]-NPs to generate a series of polyglutamated folate-HBPE-NPs of various lengths (FIG. 23). All NP formulations were characterized for degree of ligand conjugation, size, shape and CT20p loading. For screening purposes, a panel of PCa cells that express different levels of PSMA and folate receptor (FR) was used (Table 1) (Hattori, Y., et al., Folate-linked nanoparticle-mediated suicide gene therapy in human prostate cancer and nasopharyngeal cancer with herpes simplex virus thymidine kinase. *Cancer Gene Ther* 12, 796-809 (2005). Xu, L., et al., Tumor-targeted p53-gene therapy enhances the efficacy of conventional chemo/radiotherapy. *J Control Release* 74, 115-128 (2001)).

In vivo toxicity and PK studies were performed with the lead compounds. To demonstrate the PSMA-specific targeting of polyglutamated folate $^{89}$Zr:DFO-HBPE(CT20p)-NPs to PCa tumors, biodistribution studies were conducted in mouse models of PCa using PET imaging. The binding (via Standard Uptake Value [SUV] in PET) was correlated with the amount of PSMA expressed in the tumors. PET imaging allowed quantification not only of the PSMA expression at tumors but it also allowed the delivery efficacy of the NP localizing to the tumors to be judged. It was determined that $^{89}$Zr:DFO HPBE[CT20p]-NPs that are PEGylated and functionalized with polyglutamated folate ligands specifically target PSMA on PCa.

Peptide Synthesis

A total of 10 peptides were synthesized by Fmoc solid phase peptide chemistry. Five peptides were synthesized following a γ-peptide synthesis approach and the 5 others were synthesized by a-peptide synthesis (FIG. 23). Peptides had a C-terminal cysteine group, for crosslinking to the DFO-HBPE-(CT20p)-NPs using N-succinimidyl 3-(2-pyridyldithio) propionate (SPDP, Thermo Scientific) as linker. SPDP is a heterobifunctional linker that contains two reactive moieties, an N-hydroxysuccinimide (NHS) ester that reacts with primary amines and an pyridnyldisulfide that reacts with a thiol group, yielding a disulfide linker that connects the polyglutamated folate peptide to the HBPE-NPs (Josephson, L., et al., High efficiency intracellular magnetic labeling with novel superparamagnetic Tat peptide conjugates. *Bioconjugate chemistry* 10, 186-191 (1999); Perez, J. M., et al., Magnetic relaxation switches capable of sensing molecular interactions. *Nature biotechnology* 20, 816-820 (2002)). An advantage of using this chemistry is that the peptide is linked to the NP by a disulfide bond that is highly stable in aqueous solutions and physiological conditions, while the disulfide bond is sensitive to reducing agents (e.g. DTT), facilitating cleavage for easy characterization (Perez. J. M., et al., Use of magnetic nanoparticles as nanosensors to probe for molecular interactions. *Chembiochem: a European journal of chemical biology* 5, 261-264 (2004): Perez, J. M., et al., DNA-based magnetic nanoparticle assembly acts as a magnetic relaxation nanoswitch allowing screening of DNA-cleaving agents. *Journal of the American Chemical Society* 124, 2856-2857 (2002); Perez, J. M., et al., Viral-induced self-assembly of magnetic nanoparticles allows the detection of viral particles in biological media. *Journal of the American Chemical Society* 125, 10192-10193 (2003)). Using this chemistry, the number of glutamate units (0-5) were systematically varied to optimize the length of the ligand for binding. In addition, the polyglutamic unit was made with D-amino acids to prevent cleavage due to PSMA's inherent glutamate-carboxylase and hydrolase activity (FIG. 23). The γ-substituted derivatives were synthesized from D-polyglutamates and folic acid using γ-selective peptide coupling conditions, while the a-substituted analogs were accessed through a similar peptide coupling with a γ-protected folate derivative.

HBPE Conjugation

To increase the aqueous solubility of the final HBPE (DFO)-NP conjugates, the NP's carboxylic acid groups were first functionalized with polyethylene glycol (PEG) as described in Experiment 1. The overall change in surface charge (zeta potential measured using Malvern's zetasizer instrument) further confirmed the successful conjugation of diamino PEG. Next, the resulting amino-PEG-HBPE-NPs was conjugated with SPDP (10 mmol in DMSO) as described. Briefly, the amino-PEG-HBPE-NPs was incubated overnight with SPDP (75 µM) and excess was removed using a PD-10 column. Then, the SPDP-activated HBPE-NPs (containing a pyridinyldisulfide reactive group) were incubated overnight with the polyglutamated folate peptides that contain C-terminal cysteine (thiol) groups. The conjugated HBPE NPs were purified by dialysis and PD-10 column. Successful ligand conjugation was assessed by UV and FTIR measurements. The average number of ligands bound to the HBPE-NPs was controlled by varying the ligand's stoichiometry resulting in a multivalent ligand display of peptides on the HBPE surface. Preliminary studies were done by incubating HBPE NPs. PEG HBPE NPs or folate PEG HBPE-NPs with FBS to estimate the amount of nonspecific protein binding by measuring the increase in NP size by DLS after a 24-h incubation period. Results showed no detectable increase in size of the PEG-HBPE-NPs or PEG-Folate-HBPE-NPs after FBS incubation, whereas the nonpegylated HBPE-NPs had an increase of 20 nm in size, presumably due to non-specific protein absorption. These results indicate that folate does not interfere with the ability of PEG to prevent non-specific protein absorption.

In Vitro Targeting and Efficacy Studies

To examine targeted cancer cell killing by polyglutamated folate conjugated DFO-HBPE (CT20p)-NPs. PCa cell lines from Table 1 were used and viability and survival assays described in Experiment 1 were performed. Control NPs included PEGylated, (1) folate DFO-HBPE(CT20p)-NPs (from Experiment 1). (2) polyglutamated folate DFO-HBPE-NPs without CT20p, (3) non-targeted DFO-HBPE (CT20p)-NPs, (4) polyglutamated folate DFO-HBPE-NPs with control peptides. To further assess the lack of toxicity of the PSMA-targeting DFO-HBPE-NPs, a panel of non-tumorigenic cell lines such as normal prostate epithelial cells (e.g. ATCC. PCS-440-010), and hepatic cells (e.g. ATCC, CRL-11233), were incubated with the NPs and cytotoxicity was assessed as described herein.

In Vivo Toxicity

To examine in vivo toxicity, a subchronic intravenous toxicity assay was performed. Groups of male SCID mice (no tumors) were treated weekly with intravenous injections of PEGylated, polyglutamate folate conjugated HBPE DFO [CT20p] NPs for 12-13 weeks at doses ranging from 2-20 mg/kg/dose. Mice were observed daily and blood was routinely collected from each mouse for standard clinical chemistry analysis of kidney and liver function (IDEXX-Radil). At experimental endpoints, tissues from liver, kidneys, spleen and lungs were mounted for histological examination using H1 & E staining to detect any treatment effect Serum and urine were collected for detection of anti-PEGIgM (ELISA) and free hemoglobin was measured in the urine to assess if treatment causes hemolysis.

In Vivo PK Studies

PK studies were performed with SCID mice treated with PEGylated, polyglutamate folate conjugated HBPE-DFO [CT20p]-NPs or controls for 24 hours. Blood samples were collected from groups of mice after treatments (e.g. 0, 0.5, 1, 2, 4, 6, 8, 12, 24 h), plasma recovered, plasma proteins precipitated and supernatants subjected to LC/MS/MS analysis (as described in Experiment 1). This data was analyzed following standard PK parameters using noncompartment analysis to determine AUC (area under the concentration time curve). CL (total body clearance). MRT (mean residence time), the distribution half-life ($T_{1/2\alpha}$) and elimination half-life ($T1_{/2\beta}$), $C_{max}$ (the peak concentration) and $t_{max}$ (the time to reach peak concentration. Furthermore, to assess the long circulation time of the polyglutamated folate NPs in vivo, the $^{89}$Zr:DFO-grafted (CT20p) HBPE-NPs from Experiment 1 was injected to SCID mice and blood samples were collected at various time points and samples processed as described herein. The level of $^{89}$Zr-radioactivity in the blood supernatant was assessed by scintillation counting.

In Vivo Targeting Subcutaneously Implanted PC a Cells in Mice

The most optimal multivalent PSMA targeting NPs were tested in vivo with male SCID SHO mice, each bearing a PSMA-positive PC3 tumor on one flank and a PC3 wild-type tumor on the other. For the PCa tumor xenografts, ~10$^6$ cells were injected subcutaneously (sc) into each flank. Tumor formation occurred after 2-4 weeks and was monitored using calipers and ultrasound A bio-distribution study was performed to obtain information on the tumor uptake of the NPs. To this end, ca. 20 µCi of $^{89}$Zr-DFO grafted HBPE(CT20p) NPs conjugated to the lead PSMA targeting ligands were injected into a cohort of mice and the tumors and organs were harvested 6, 12, 24, 48, 72 and 9 h after injection. The time point for the following in vivo imaging studies were based on the bio-distribution data. For PET imaging (Focus 120. CTI/Siemens), standard uptake values (SUV) were determined for the PSMA(+) and (−) tumors. Dose finding studies were performed to obtain the minimal required dose for imaging, which are at around 125 µCi. The tumors were harvested for immunohistochemistry to detect PSMA and to confirm co localization of the probe via autoradiography. Based upon the specific activity of the NPs, the amount of NPs within the tumors was estimated. To assess the specific binding of the NPs to PSMA, the following controls were used, (1) HBPE-NP without targeting ligand, (2) PMPA, as a known inhibitor of PSMA, was co-injected with the NPs and (3) excess (non-conjugated) small molecule ligands were co-injected with the NPs as blocking experiments. A set of control experiments included mice bearing FR(+)/PSMA(−) tumors (such as MDA-MB 231 tumors) to test the specificity of the NPs for PSMA over FR.

Completion of Experiment 2 resulted in optimized polyglutamated folate DFO-HBPE (CT20p) NPs in the ~80 nm range that were internalized by PCa cells via PSMA, with minimal uptake by the FR, causing PCa-specific cell death. PK studies in mice showed protection of CT20p in NPs and extended circulation of particles to yield optimal peptide dosing and toxicity information. The results from PET imaging indicate that polyglutamated folate $^{89}$Zr:DFO-HBPE (CT20p) NPs principally localize to PSMA-expressing PCa tumors with little to no off-site targeting to FR(+) or PSMA(−) tumors or tissues like the liver or spleen.

The proposed polyglutamated folate peptides were synthesized by standard solid-state peptide chemistry and obtained commercially. The peptide synthesis procedures to build both the γ-polyglutamated folate peptide as well as the standard a-linked version were commercially available as were the conjugation procedures of β-alanine and folic acid. The use of SPDP to link a cysteine-containing peptide to NPs has been performed. In the unlikely event that use of SPDP proves unsatisfactory, select "click" chemistry. In this application, polyglutamated folate peptides with a C-terminus azide (Ns) modification are used to conjugate to propargylated functionalized HBPE-NPs. This conjugation chemistry has been used. Recently developed click chemistry reactions that do not use Cu for this conjugation are now commercially available (Sigma) and can be used as alternatives (Baskin, J. M., et al., Copper-free click chemistry for dynamic in vivo imaging. *Proceedings of the National Academy of Sciences of the United States of America* 104, 16793-16797 (2007); Soriano Del Amo, D., et al., Biocompatible copper(1) catalysts for in vivo imaging of glycans. *Journal of the American Chemical Society* 132, 16893-16899 (2010)). In the unlikely event that the glutamated folate-peptides fail to achieve selective PSMA-targeting, an alternative approach using glutamate ureas can be employed and the synthesis of this approach can be optimized (Chen, Y., et al., Synthesis and biological evaluation of low molecular weight fluorescent imaging agents for the prostate-specific membrane antigen. *Bioconjugate chemistry* 23, 2377-2385 (2012)). Also where PK studies show limited circulation of peptides or NPs, modified PEG chains can be conjugated to the NPs.

The NP experiments disclosed herein result in data on optimized reaction conditions. Data was tabulated and statistical analysis was performed as described in Experiment 1.

Experiment 3. Examination of the Anti-Cancer Activity of Polyglutamated Folate-HBPE[CT20p]-NPs in Metastatic PCa The potential value of the PSMA-targeted peptide/NP platform to regress PCa tumors and impair metastatic disease was investigated in mouse models of PCa and bone metastasis.

The disclosed studies had significant health benefits for patients with CRPC by providing a therapeutic agent that impairs metastasis without the side effects associated with current treatment approaches as well as providing a noninvasive method for imaging treatment outcomes in pre-clinical studies.

PCa may grow slowly for many years; but in time the cancer invades neighboring tissue and enters circulation to metastasize at distant sites. For advanced PCa, hormone therapy results in positive responses rates of 80-90%. However, most men eventually develop progressive disease or CRPC following hormone therapy and usually suffer severe side effects from treatments, which can include impotence, incontinence, heart disease and osteoporosis (Schrecengost, R, et al., Molecular pathogenesis and progression of prostate cancer. *Seminars in oncology* 40, 244-258 (2013)). Detection of early metastasis remains one of the challenges for PCa due to the highly variable time frame of metastasis occurrence for the post-treatment patient. Current therapies for CRPC and patients with metastatic disease usually target hormone (androgen) synthesis or signaling (e.g. abiraterone, enzalutamide). These approaches are not curative and only extend for a short period (Leibowitz-Amit, R, et al., Targeting the androgen receptor in the management of castration-resistant prostate cancer: rationale, progress, and future directions. *Curr Oncol* 19, S22-31 (2012); Leibowitz-Amit, R, et al., The changing landscape in metastatic castration-resistant prostate cancer. *Current opinion in supportive and palliative care* 7, 243-248 (2013)). To address these problems, targeted therapeutics are needed that allow for the specific delivery and concentration of drugs to tumors localized to the prostate as well as to metastatic sites, most commonly in the lymph nodes or bone, while causing minimal damage to healthy (non-transformed) tissue. Hampering treatment outcomes is the fact that monitoring of drug delivery and assessment of therapeutic efficacy, using existing imaging technologies in the clinic, is difficult due to the low metabolic rate of PCa and the close proximity of the prostate to the bladder. Such problems limit the use of standard PET imaging with $^{18}$F-FDG, since the tracer accumulates in the bladder immediately above the prostate, thus obscuring its evaluation. The development of a targeted molecular nanotheranostic (dual therapy and diagnostic) platform that delivers and concentrates therapeutic agents in PCa tumors, and integrates the capacity for imaging, provides a much needed therapeutic approach for patients with CRPC. A NP platform is ideal as NPs are long-circulating agents that, when properly decorated with targeting ligands that bind to cancer cell receptors, display minimal liver accumulation, renal excretion or localization of cargo, like imaging agents, to the bladder. Disclosed herein is a targeted NP platform developed to encapsulate a therapeutic peptide (CT20p) and endow the NPs with PET imaging capabilities in order to monitor bio-distribution and efficacy in murine models of PCa and metastatic disease.

The CT20 Peptide and Targeting to PSMA

CT20p is a small lipophilic peptide based on the α9 helix of Bax. Importantly, CT20p has properties that are distinct from the parent protein. Using biophysical and cell biology methods, it was shown that CT20p formed a type of pore in simple lipid membranes (Garg, P., et al., Transmembrane pore formation by the carboxyl terminus of Bax protein. *Biochimica et biophysica acta* 1828, 732-742 (2013): Tatulian, S. A., et al., Molecular basis for membrane pore formation by Bax protein carboxyl terminus. *Biochemistry* 51, 9406-9419 (2012)). Expression or introduction of CT20p in cancer cells resulted in mitochondrial localization of the peptide followed by cell death that was different from the parent protein in that Bcl-2 overexpression. Bax deficiency or caspase inhibition minimally blocked it (Boohaker, R. J., et al. Rational Development of a Cytotoxic Peptide To Trigger Cell Death. *Molecular pharmaceutics* (2012)). This indicated that CT20p did not trigger the conventional mitochondrial apoptotic pathway that is frequently mutated in cancer cells. It is shown herein that CT20p preferentially targets mitochondria within cancer cells, causing clustering of these organelles. This reduces energy production which is required for the cytoskeleton to mediate adhesion and motility, leading to cell detachment and death (anoikis). These effects were not observed in normal cells, such as fibroblasts, normal epithelia and macrophages, since the mitochondria of non-transformed cells are less susceptible to the lethal effects of CT20p. This is highly significant as the administration of traditional drugs to treat cancer causes debilitating side effects due to their off-target toxicity (Tolaney, S. M., et al., Lymphopenia associated with adjuvant anthracycline/taxane regimens. *Clinical breast cancer* 8, 352-356 (2008)). Unlike these traditional drugs, the cancer-selective activities of CT20p block invasiveness and prevent metastasis without damaging normal cells.

Encapsulation of CT20p into HBPE-NPs facilitated the delivery of the peptide to PCa cells. HBPE-NPs were perfectly suited for this task as these can encapsulate multiple cargos within their hydrophobic nanocavities, without affecting the distribution of targeting ligands on the NPs' surface. An encapsulation efficacy of CT20p within HBPE-NPs of 95% was achieved, with particle stability at physiological pH and release of the peptide at pH<5. To deliver CT20p to PCa cells, especially metastatic cells, the peptide was encapsulated within HBPE-NPs that were functionalized with polyglutamated folates Polyglutamated folates are an innovative way to target PSMA, a PCa-specific cell surface protein highly expressed in PCa tumors but not normal prostate (Bostwick, D. G., et al., Prostate specific membrane antigen expression in prostatic intraepithelial neoplasia and adenocarcinoma: a study of 184 cases. *Cancer* 82, 2256-2261 (1998); Israeli, R. S., et al., Molecular cloning of a complementary DNA encoding a prostate-specific membrane antigen. *Cancer research* 53, 227-230 (1993). Ross, J. S., et al. Correlation of primary tumor prostate-specific membrane antigen expression with disease recurrence in prostate cancer. *Clinical cancer research: an official journal of the American Association for Cancer Research* 9, 6357-6362 (2003); Silver, D. A., et al., Prostate-specific membrane antigen expression in normal and malignant human tissues. *Clinical cancer research: an official journal of the American Association for Cancer Research* 3, 81-85 (1997)) PSMA expression correlates with androgen independence and increased malignancy of PCa (Wright, G. L., Jr, et al. Upregulation of prostate-specific membrane antigen after androgen-deprivation therapy. *Urology* 48, 326-334 (1996)). Most importantly PSMA is overexpressed in PCa metastatic lesions, facilitating the targeting of the therapeutic NP to metastatic sites like bone or lymph nodes (Chang, S. S., et al. Five different anti-prostate-specific membrane antigen (PSMA) antibodies confirm PSMA expression in tumor-associated neovasculature. *Cancer research* 59, 3192-3198 (1999); Milowsky. M. J., et al. Vascular targeted therapy with anti-prostate-specific membrane antigen monoclonal antibody J591 in advanced solid tumors. *J Clin Oncol* 25, 540-547 (2007); Morris, M. J., et al. Phase I evaluation of J591 as a vascular targeting agent in progressive solid tumors. *Clinical cancer research: an official journal of the American Association for Cancer Research* 13, 27072713 (2007)). Polyglutamated folates specifically target PSMA on PCa cells and not the folate receptor (FR) (found on cells like macrophages) because PSMA exhibits glutamate carboxylase as well as folate hydrolase activities, hydrolyzing extracellular polyglutamated folate to mono glutamic folic acid that is utilized by cells (Ghosh, A., et al., Tumor target prostate specific membrane antigen (PSMA) and its regulation in prostate cancer. *J Cell Biochem* 91, 528-539 (2004)). Upregulation of PSMA provides PCa cells with a growth advantage in the low folate tumor environment, preventing downregulation of PSMA and ensuring a stable target for the HBPE-NPs encapsulating CT20p (Yao, V., et al., Prostate specific membrane antigen (PSMA) expression gives prostate cancer cells a growth advantage in a physiologically relevant folate environment in vitro. *The Prostate* 66, 867-875 (2006); Yao, V., et al., Expression of prostate-specific membrane antigen (PSMA), increases cell folate uptake and proliferation and suggests a novel role for PSMA in the uptake of the non-polyglutamated folate, folic acid. *The Prostate* 70, 305-316 (2010)) The disclosed compositions and methods take advantage of PSMA's binding affinity towards polyglutamated folate to develop a NP platform technology for delivery of the CT20p to PCa.

A NP platform was developed that targets PCa cells via PSMA to deliver a therapeutic peptide and incorporates imaging capabilities to facilitate pre-clinical bio-distribution, pharmacokinetics (PK) and efficacy studies. The major innovative feature is the combination of an optimized NP design that protects and delivers a therapeutic cargo, CT20p, to cancer cells, and a targeting scheme that relies on a biomarker, PSMA, which is unique to high grade and metastatic PCa. In pre-clinical models, similar ligand-targeted NPs provided benefits in terms of target cell internalization and retention (van der Meel. R. et al., Ligand-targeted particulate nanomedicines undergoing clinical evaluation: current status. *Advanced drug delivery reviews* 65, 1284-1298 (2013)). However, the ligand-targeted HBPE-NPs disclosed herein are an improvement over other nanomaterials because these do not produce toxic effects, such as the generation of reactive oxygen species (ROS), induction of autophagy or lysosomal degradation, associated with particles made from iron oxide, silica or titanium (Stem. S.T., et al., Autophagy and lysosomal dysfunction as emerging mechanisms of nanomaterial toxicity. *Particle and fibre toxicology* 9, 20 (2012). The platform disclosed herein is distinct from nanomedicines, such as liposomes, in terms of the composition of the HBPE-NPs and, most importantly, its cargo (CT20p), which unlike other drug payloads (e.g. Doxorubicin or Taxol) is cancer-cell specific with little to no cytotoxicity to non-cancerous tissues as is described herein.

Polymeric NP Design for Dual Therapy and Imaging

In one aspect, the surface of the NPs disclosed herein comprised carboxylic acid groups that enable functionalization with targeting ligands. These NPs were fabricated from an aliphatic HBPE polymer which was modified to graft chelating ligands (eg, DTPA, DOTA or DFO) for PET imaging capabilities (Santra, S., et al., Aliphatic hyperbranched polyester: a new building block in the construction of multifunctional nanoparticles and nanocomposites. *Langmuir* 26, 5364-5373 (2009)). The designed HBPE polymers have major advantages over conventional linear polymers (such as PLGA) since: (i) they are highly branched, creating unique hydrophobic cavities; (ii) they display numerous surface carboxylic acid groups for facile labeling of targeting ligands, and (iii) monomers contain an acidic proton that can be easily displaced by a pendant ligand to achieve further functionalization of the NP's cavities, such as introducing a chelating ligand for stable encapsulation of radioactive isotopes for PET imaging. Note that current linear polymers fail to generate well-defined hydrophobic nanocavities and are, thereby, difficult to modify chemically and introduce multiple functionalities. For example, dendrimers, although highly branched, form nanocavities that are difficult to synthesize and chemically engineer to introduce imaging functionalities. Hence, a strong innovative aspect of the approach disclosed herein is the use of the HBPE polymer to fabricate a multifunctional theranostic polymeric NP targeting a PCa specific protein, PSMA, while chemically engineering the particle's nanocavities to incorporate chelating agents for PET imaging. While the PET imaging feature of the HBPE-NPs is for the assessment of the nanoagent's bio-distribution in mice, the present disclosure advances the translational use of PET to assess the delivery of therapeutics in patients. To endow the NPs with PET imaging capabilities, Desferrioxamine (DFO) was grafted onto the HBPE nanocavities DFO is a chelating agent that strongly binds Zr and is used in the design of $^{89}$Zr-PET imaging probes (Kiss. T, et al., Metal-binding ability of desferrioxamine B. *Journal of Inclusion Phenomena and Molecular Recognition in Chemistry* 32, 385-403 (1998)). By introducing a pendant group into the hydrophobic cavities with selective binding to $^{89}$Zr, the ability of the HBPE-NPs to chelate $^{89}$Zr and also encapsulate the therapeutic peptide. CT20p, while displaying targeting ligands was increased; thus creating a NP platform to assess the delivery of a therapeutic peptide by PET imaging. The use of $^{89}$Zr as a PET tracer is gaining acceptance as a long-lived positron emitter radioisotope for the detection of tumors by PET (Meijs, W. E., et al. Zirconium-labeled monoclonal antibodies and their distribution in tumor-bearing nude mice. *Journal of nuclear medicine: official publication, Society of Nuclear Medicine* 38, 112-118 (1997); Verel, I., et al., 89Zr immuno-PET: comprehensive procedures for the production of $^{89}$Zr-labeled monoclonal antibodies. *Journal* of nuclear medicine: official publication, Society of Nuclear Medicine 44, 1271-1281 (2003)). The $^{89}$Zr radionuclide has multiple advantages over $^{64}$Cu radionuclide such as: (1) a half life of approximately 78.4 h (3.17 days) as opposed to the 12.7 h for the $^{64}$Cu isotope, (2) a positron yield of 22.7% which improves counting statistics when compared to other radioisotopes, (3) no known toxicity to biological systems, and (4) generation of $^{89}$Zr is cost effective and highly efficient Recently, the use of $^{89}$Zr-labeled antibodies to image HER2/neu-positive (Holland, J. P., et al., Measuring the pharmacodynamic effects of a novel Hsp9) inhibitor on HER2/neu expression in mice using Zr-DFO-trastuzumab. *PLoS One* 5, e8859 (2010)) and PSMA-positive (Ruggiero, A., et al., Targeting the Internal Epitope of Prostate-Specific Membrane Antigen with $^{89}$Zr-7E11 Immuno-PET. *Journal of nuclear medicine: official publication, Society of Nuclear Medicine* 52, 1608-1615 (2011)) tumors in vivo was reported and the potential clinical use of this radiotracer for localizing these tumors was suggested. As $^{89}$Zr has a long half-life (3.17 days), it is appropriate for encapsulation into long circulating NPs.

In another aspect, disclosed are the design and screening of polyglutamated folate peptides as targeting ligands to PSMA. PSMA is a validated target to deliver imaging and therapeutic agents to PCa. An anti-PSMA monoclonal antibody (mAb) was used to image and deliver chemotherapeutics directly to PCa; however this approach, while proof of principal, was suboptimal with low sensitivity to detect viable tumors (Freeman. L. M., et al. The role of(111) In Capromab Pendetide (Prosta-ScintR) immunoscintigraphy in the management of prostate cancer. *Q J Nucl Med* 46, 131-137 (2002): Haseman, M. K., et al., Capromab Pendetide imaging of prostate cancer. *Cancer Biother Radiopharm* 15, 131-140 (2000); Horoszewicz, J. S., et al., Monoclonal antibodies to a new antigenic marker in epithelial prostatic cells and serum of prostatic cancer patients. *Anticancer Res* 7, 927-935 (1987); Lopes, A. O., et al., Immunohistochemical and pharmacokinetic characterization of the site-specific immunoconjugate CYT-356 derived from antiprostate monoclonal antibody 7E11-C5. *Cancer research* 50, 6423-6429 (1990): McDevitt, M. R., et al., An alpha-particle emitting antibody ([213Bi]J591) for radioimmunotherapy of prostate cancer. *Cancer research* 60, 6095-6100 (2000); Smith-Jones, P. M., et al., Radiolabeled monoclonal antibodies specific to the extracellular domain of prostate-specific membrane antigen: preclinical studies in nude mice bearing LNCaP human prostate tumor. *Journal of nuclear medicine: official publication, Society of Nuclear Medicine* 44, 610-617 (2003)). As alternative to antibodies, PSMA-binding aptamers were identified and conjugated to polymeric NPs, encapsulating the anticancer drug, Docetaxel, for the targeted treatment of LNCaP xenografts in nude mice (Cheng, J., et al., Formulation of functionalized PLGA-PEG nanoparticles for in vivo targeted drug delivery. *Biomaterials* 28, 869-876 (2007); Farokhzad, O. C., et al., Targeted nanoparticle-aptamer bioconjugates for cancer chemotherapy in vivo. *Proceedings of the National Academy of Sciences of the United States of America* 103, 6315-6320 (2006); Farokhzad, O. C., et al., Nanoparticle-aptamer bioconjugates: a new approach for targeting prostate cancer cells. *Cancer research* 64, 7668-7672 (2004)). However, these studies were not reproducible due to stability issues with the aptamers in serum. Moreover, while some NP formulations, using antibodies and aptamers to target PSMA, are currently in Phase I clinical trials, these NPs do not possess imaging capabilities (Hrkach, J., et al., Preclinical development and clinical translation of a PSMA-targeted docetaxel nanoparticle with a differentiated pharmacological profile. *Science translational medicine* 4, 128ra139 (2012)). In addition, other targeting ligands for PSMA include glutamated ureas: which further validates the use of glutamate conjugates of folate to target PSMA (Barrett. J. A., et al., First-in-man evaluation of 2 high-affinity PSMA-avid small molecules for imaging prostate cancer. *Journal of nuclear medicine: official publication, Society of Nuclear Medicine* 54, 380387 (2013); Chen. Y., et al., Radiohalogenated prostate-specific membrane antigen (PSMA)-based ureas as imaging agents for prostate cancer. *J Med Chem* 51, 7933-7943 (2008)). However, the complex synthesis of glutamated ureas hampers their widespread use and study. Hence, while targeting PSMA had been validated in other studies, the use of effective ligands for PSMA remained to be developed and the incorporation of imaging agents had not be achieved. To address this problem, a method to target NPs to PSMA is disclosed herein. Considering that PSMA utilizes polyglutamated folate as its biological ligand and it is shown herein that folic acid-conjugated HBPE-NPs target PSMA, a series of polyglutamated folate peptides were conjugated on the HBPE-NP surface for targeting PSMA. Screening of these polyglutamated folate peptides-NP formulations identified a conjugate with higher and more specific binding toward PSMA than folate alone with minimal binding to the folate receptor (FR). The approach disclosed herein is significantly different from others that targeted PSMA since polyglutamated folate peptides were used to direct NPs to PSMA-expressing PCa cells. As these peptides are more stable and easier to manufacture than monoclonal anti-PSMA antibodies, members of the resulting multivalent HBPE-NP library provide a more robust PSMA-targeting nanoplatform to target PCa. Finally, as PSMA is not only expressed in the primary tumor, but also in metastatic lesions, it facilitated the delivery of CT20p to treat the primary tumor and also any metastasis.

Cancer-specific therapeutic peptide with anti-metastatic activity. In another aspect, disclosed is the therapeutic peptide. CT20p (Boohaker, R. J., et al., The use of therapeutic peptides to target and to kill cancer cells. *Current medicinal chemistry* 19, 3794-3804 (2012)). This peptide induces cancer-specific cell death. Currently biologicals like CT20p account for ~30% of drugs being tested and about half of new molecular entities. However, the mechanism of action for many biologicals, such as anti-microbial peptides, remains mostly unknown, challenging the identification of target patient populations CT20p is an improvement in that it works in the nanomolar range, and the method by which it exerts its biological activity on cells is disclosed herein. The cancer-specificity of CT20p is based on its effects upon mitochondrial dynamics and the cytoskeleton. This powerful cancer-directed action of CT20p impairs the invasiveness that underlies the transition to metastasis, indicating that the peptide is ideal for use in cancer patients with disseminated disease, such as can result from CRPC. In addition, the ability of CT20p to spare normal cells lies with the fact that the peptide takes advantage of documented differences in mitochondrial physiology unique to cancer cells (Desai, S. P., et al., Mitochondrial localization and the persistent migration of epithelial cancer cells. *Biophysical journal* 104, 2077-2088 (2013): Zhao. J., et al., Mitochondrial dynamics regulates migration and invasion of breast cancer cells. *Oncogene* 32, 4814-4824 (2013)). Disclosed herein is the first study to develop a therapeutic peptide with anti-metastatic properties that can be encapsulated in HBPE-NPs, specifically targeted to PCa via PSMA. As shown in FIG. 1, the uniqueness of the HBPE-NP-CT20p platform extends to its ability to efficiently escape endosomes. Ligand-targeted HBPE-NPs were internalized through receptor-mediated endocytosis. The HBPE-NPs protected the peptide through the endocytic pathway, destabilizing at the acidic pH of late endosomes-lysosomes as shown herein. CT20p (which contains charged residues) then escaped from the endosomes, potentially by forming a pore in the endosome membrane was showed with lipid vesicles, and then chaperones, like HSP90, facilitated translocation to the cytosol as was reported with other endosome-localized proteins (e.g. toxins (Ratts, R., et al., The cytosolic entry of diphtheria toxin catalytic domain requires a host cell cytosolic translocation factor complex. *The Journal of cell biology* 160, 1139-1150 (2003)) or growth factors (Wesche, J., et al., FGF-1 and FGF-2 require the cytosolic chaperone Hsp90 for translocation into the cytosol and the cell nucleus. *The Journal of biological chemistry* 281, 11405-11412 (2006)). Once in the cytosol. CT20p then associated with mitochondria.

Engineering of Polymeric NP

Figure 16:
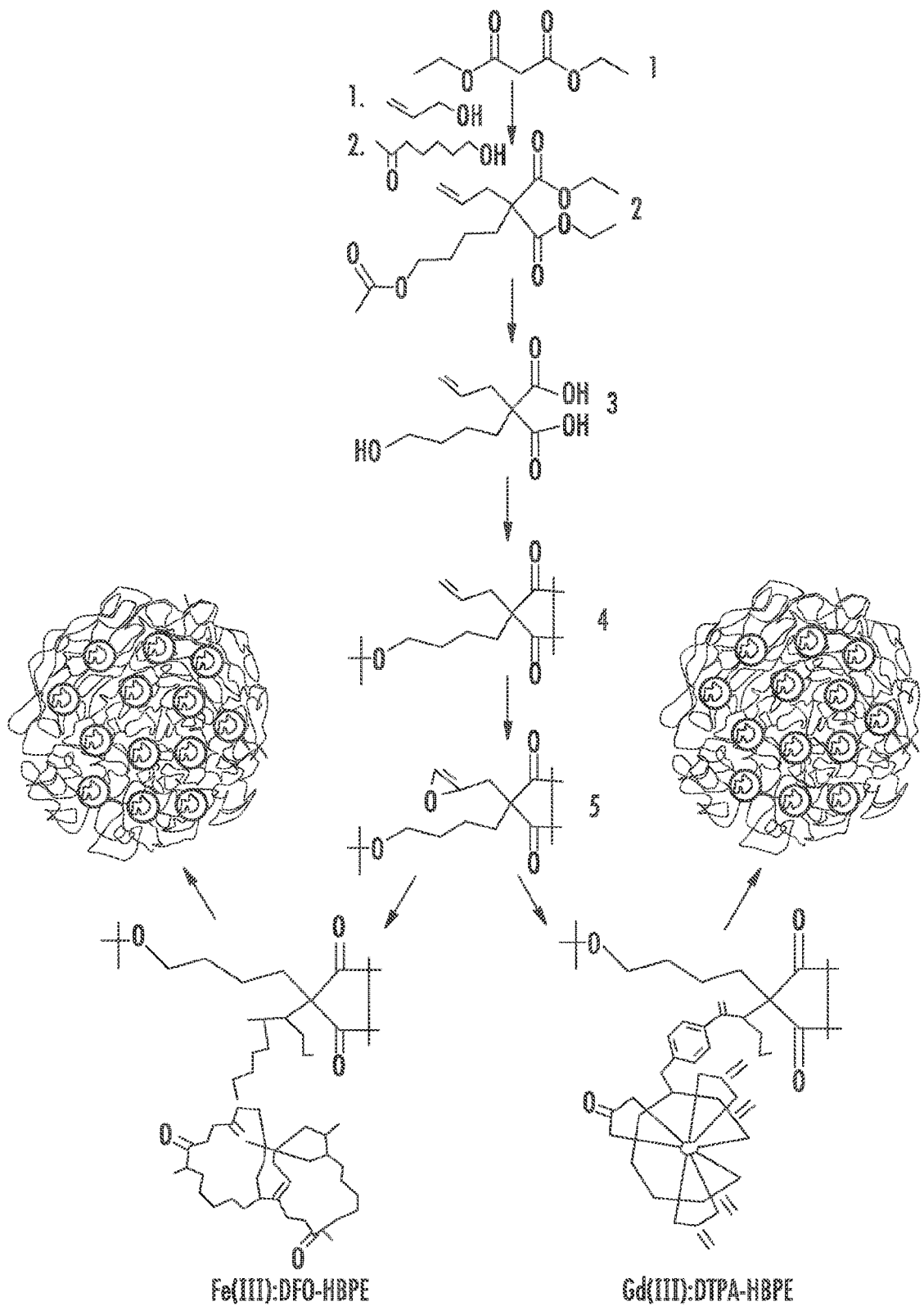
FIG. 16 illustrates the synthetic route for Gd-DTPA and Fe(III)-DFO-HBPE-NPs.

To endow HPBE-NPs with imaging capabilities, the synthesis procedure was modified to generate an epoxy grafted polymer that produced Fe(III)-DFO-grafted or Gd(III)-DTPA-grafted HBPE polymers (FIG. 16). Briefly, diethylmalonate (1) (62.5 mmol), 3-chloroprop-1-ene (62.5 mmol) and potassium carbonate (312.5 mmol) were taken in acetonitrile and refluxed. Stoichiometric amounts of chloroprop-1-ene and potassium carbonate, as a mild base, facilitated the release of one acidic proton from 1. The resulting monoalkylated product (40.0 mmol), was purified by flash chromatography and reacted with 4-bromobutyl acetate (48 mmol) in a dry THF solution containing NaH (56 mmol). In this second step, the use of NaH as a stronger base and the excess amount of 4-bromobutyl acetate ensured the removal of the second acidic proton and the formation of the dialkylated compound 2. Deprotection of 2 (19.2 mmol), by hydrolysis of the protecting ester groups in an aqueous methanol solution containing NaOH (67.3 mmol), resulted in the formation of monomer 3, containing a propene group as a pendant ligand. Monomer 3 was polymerized using p-toluenesulfonic acid (100:1 molar ratio) as catalyst. The resulting propene-grafted polymer 4 was oxidized to an epoxide to make it reactive to the terminal amine group in DFO or DTPA-amine. Briefly, 3-chloroperoxybenzoic acid (1.2 mmol) was dissolved into a mixture of dry dichloromethane (DCM) and $Na_2CO_3$ (1.2 mmol). To this, the polymer 4 (120 mg) dissolved in dry DCM was added. The oxidized polymer was precipitated in water to obtain the epoxy-grafted polymer intermediate 5. This reactive epoxy-grafted polymer 5 generated either an Fe(III)-DFO- or the Gd(III)-DTPA-grafted HBPE by reacting the epoxy polymer (40 mg) with the corresponding chelator (0.122 mmol) in a methanol solution containing triethylamine (0.203 mmol). GPC analysis indicated an average polymer molecular weight of 40 kDa. To assess the NP bio-distribution by PET, the DFO-grafted HBPE-NPs that encapsulate $^{89}Zr$ were studied. This route was chosen as PET is more sensitive than MRI and is the imaging modality typically used in biodistribution studies. In FIG. 3, the DFO-grafted HBPE-NPs were fabricated using a $Fe^{3+}$ chelated DFO to facilitate "wrapping" of the DFO around the metal for a better fit in the NP's inner cavities via the solvent diffusion method (FIG. 17A). Under these conditions, the miscible solvent rapidly diffused into the water, causing the polymer to self-assemble, forming polymeric NPs encapsulating molecules within hydrophobic pockets. This process exposed the hydrophilic segments of the polymer to the aqueous solution, resulting in the formation of carboxyl-functionalized NPs encapsulating a near-infrared dye, chelated metal and CT20p.

Figure 14A:
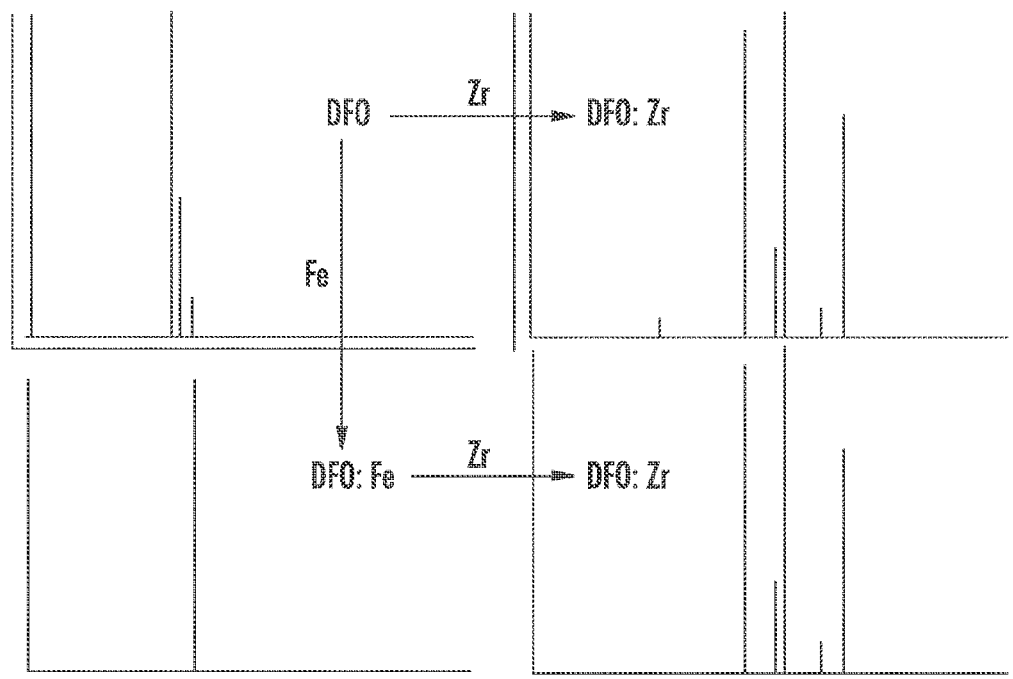
FIG. 14A depicts a mass spectrometry confirmation of the ability of DFO and DFO:Fe to chelate Zr.
Figure 14B:
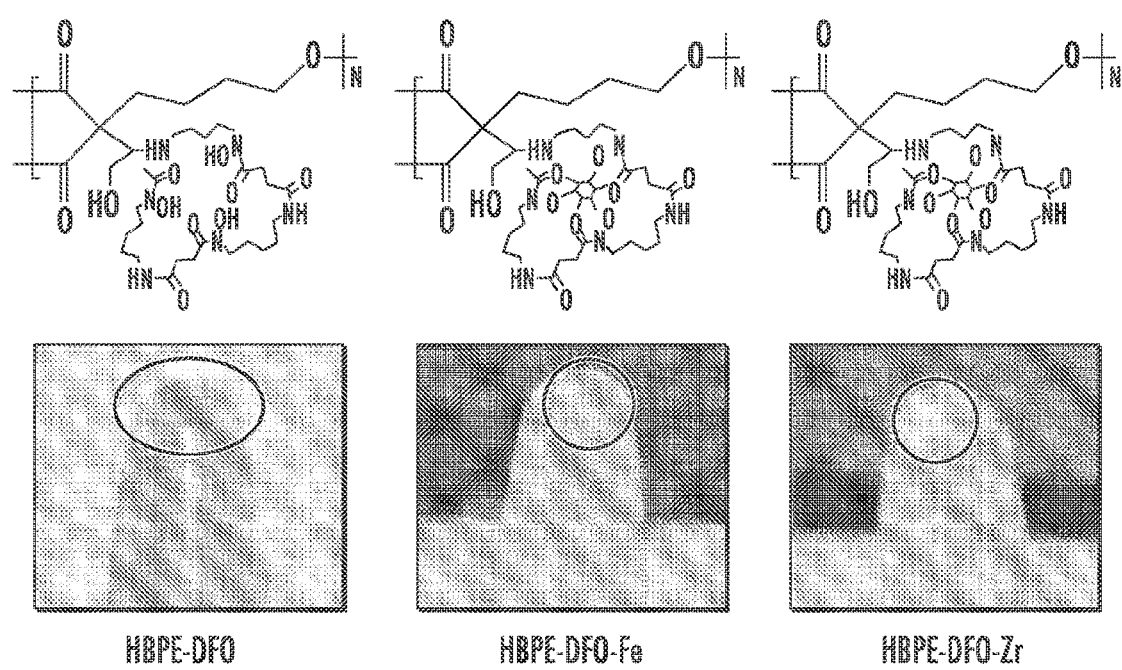
FIG. 14B shows the generation of the $^{89}$Zr-DFO-HBPE nanoparticles from Fe-DFO-HBPE.
Figure 15:
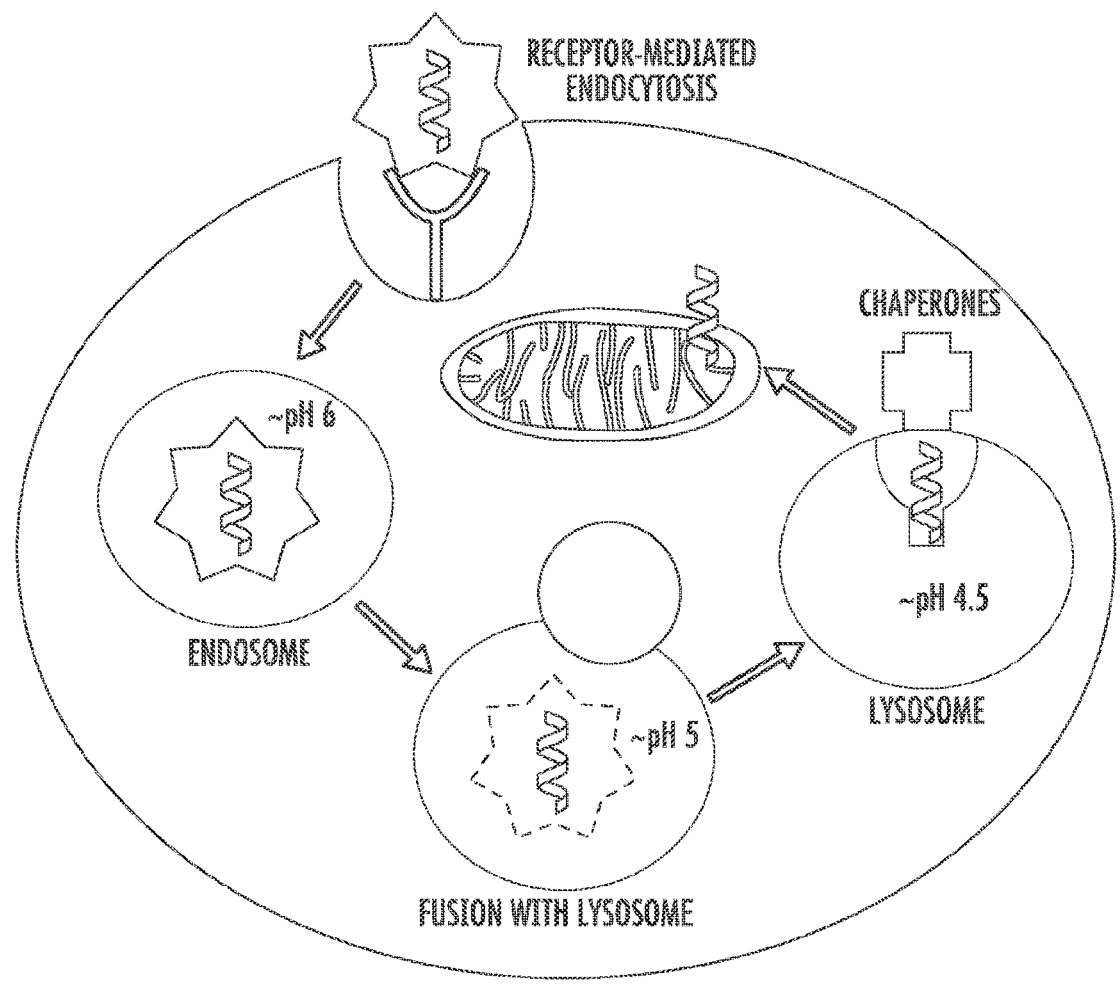
FIG. 15 is a schematic representation of a proposed mechanism by which CT20p, in HBPE-NPs, is released from endosomes/lysosomes under acidic conditions, forms a pore, and translocates to the cytosol via chaperone to bind to mitochondria.
Figure 17C:
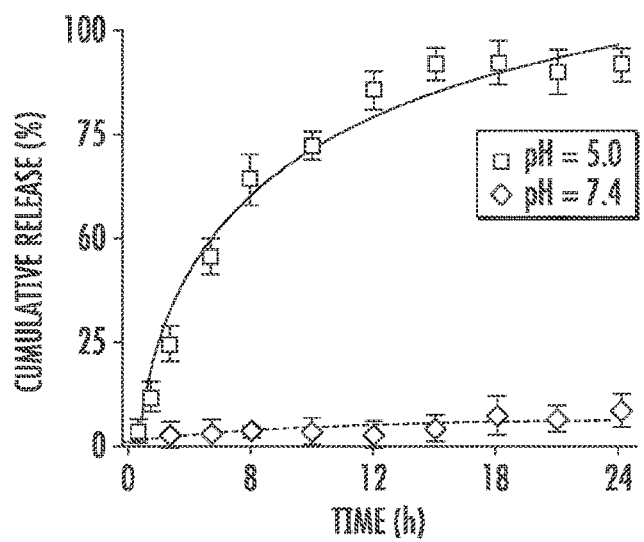
FIG. 17C is a graph showing the CT20p release profile at acidic pH.

HBPE-NPs surface functionalization with folate ligands was performed using standard conjugation procedures (Kaittanis, C., et al., Role of nanoparticle valency in the nondestructive magnetic-relaxation-mediated detection and magnetic isolation of cells in complex media. *Journal of the American Chemical Society* 131, 12780-12791 (2009); Santra, S., et al., Drug/dye-loaded, multifunctional iron oxide nanoparticles for combined targeted cancer therapy and dual optical/magnetic resonance imaging. *Small* 5, 1862-1868 (2009); Santra, S., et al., Cell-specific, activatable, and theranostic prodrug for dual-targeted cancer imaging and therapy. *Journal of the American Chemical Society* 133, 16680-16688 (2011); Santra, S, et al., Selective N-Alkylation of beta-Alanine Facilitates the Synthesis of a Poly (amino acid)-Based Theranostic Nanoagent. *Biomacromolecules* (2011)). To conjugate folic acid to the HBPE-DFO (CT20p)-NPs, folic acid was reacted with ethylene diamine to yield aminated folate (Folate-NH2), which was reacted to the carboxylic acid groups on HBPE-DFO(CT20p)-NPs via carbodiimide chemistry, forming the folate conjugated HBPE-DFO(CT20p)-NPs. Scanning transmission electron microscopy (STEM) showed that these NPs were, on average, monodispersed NPs of 80 nm in diameter (FIG. 17B). As CT20p is a hydrophobic peptide, it can be encapsulated within the hydrophobic pockets of the hyperbranched polymer during NP formation with an encapsulation efficacy of 95%. The CT20p peptide cargo within the NP was stable at physiological pH (~pH 7) and only released from the NP at pH (<pH5) (FIG. 17C). Upon incubation with cold $Zr^{4+}$ (in the form of $ZrCl_4$), the chelated $Fe^{3+}$ was easily displaced by $Zr^{4+}$. This was corroborated by ICP-MS results, showing a percent by weight of $Zr^{4+}$ to polymer of 0.15% in the final HBPE-DFO(CT20p)-NP formulation. No Zr was detected in control HBPE-NPs, which indicated that the NPs without DFO did not chelate Zr non-specifically Mass spectrometry studies of DFO and DFO Fe, incubated with Zr, showed that both can chelate Zr (FIG. 14A) and that the DFO:Fe can exchange the Fe for Zr. Visual confirmation of Fe-chelation and displacement by $Zr^{3+}$ was observed as an intense orange coloration in the Folate-HBPE-DFO(CT20p)-NPs that occurred upon Fe addition and disappeared upon subsequent addition of Zr (FIG. 14B). The presence of Zr in the polymer was corroborated by ICP-MS. These results provide a reliable way to label the Folate-HBPE-DFO(CT20p)-NPs with $^{89}Zr$ for PET imaging right before the animal studies Therefore, the HBPE-NPs can be tailored to chelate a radioisotope for PET imaging that, when delivered to PCa cells, produce a targeted PET imaging agent for assessment of drug biodistribution.

Peptide Cargo with Cancer Specific Mitotoxic and Anti Adhesion Activity

Figure 18A:
FIGS. 18A-18J illustrate a timeline of CT20p activities in cancer cells.
Figure 18B:
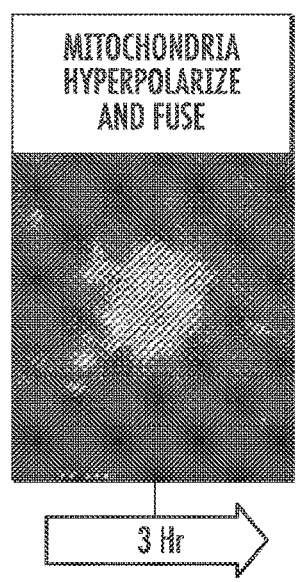
Figure 18C:
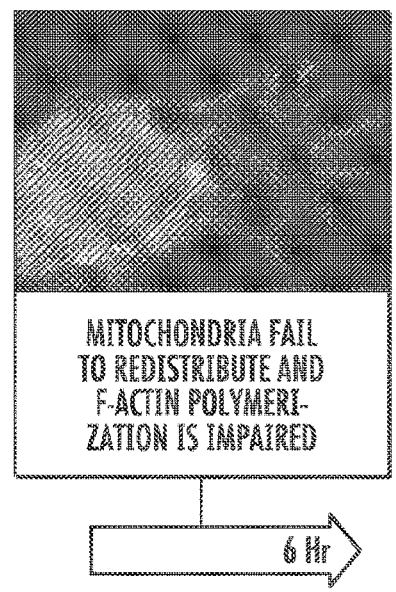
Figure 18D:
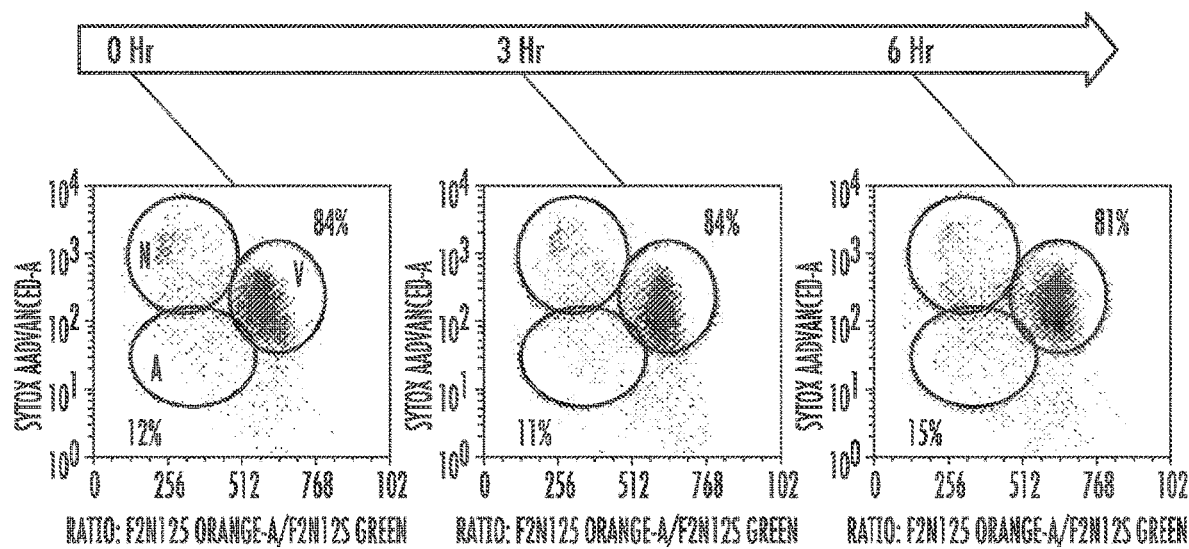
Figure 18E:
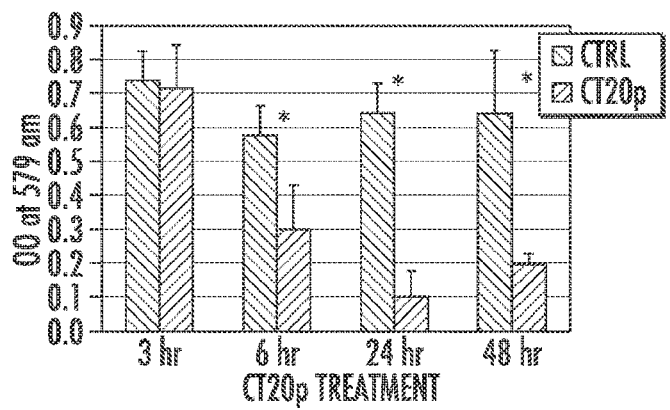
Figure 18F:
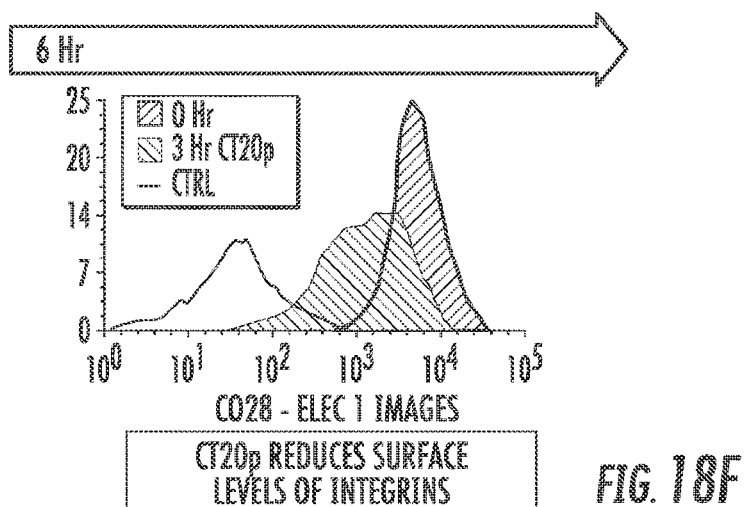
Figure 18G:
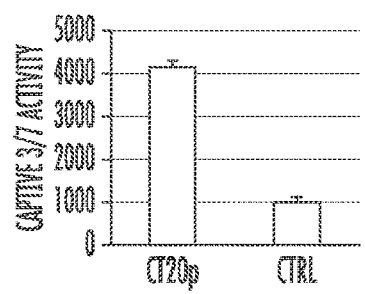
Figure 18H:
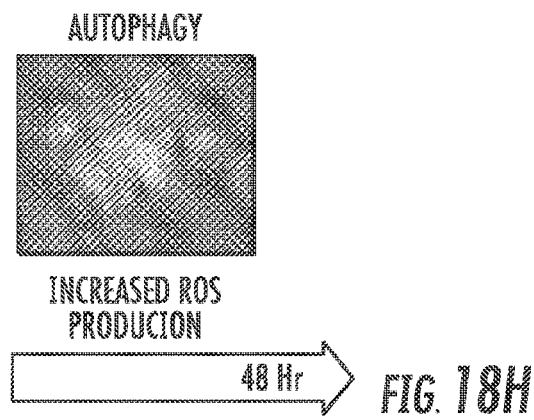
Figure 18I:
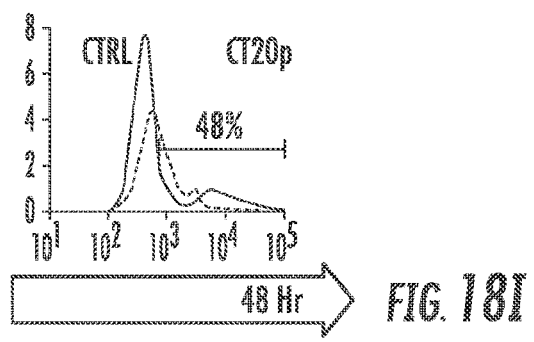
Figure 18J:
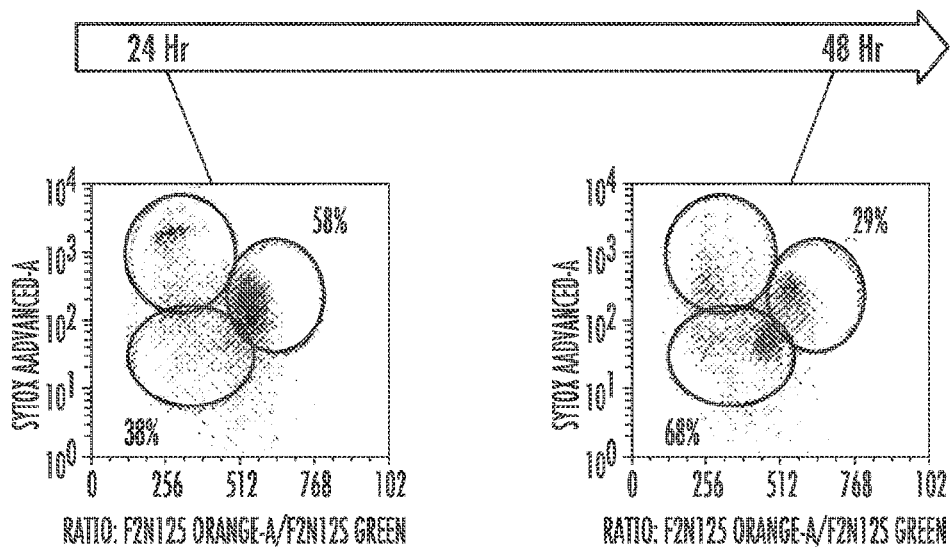

Recently, a mitotoxic peptide that kills cancer cells was discovered. To visualize the cytosolic localization of CT20p (delivered to cells by HBPE-NPs), rhodamine-labeled CT20p was used, which proved equally effective in killing as compared to the unlabeled peptide. Using nanomolar amounts of CT20p (~3.4 nM) in NPs, co-localization of the peptide (red) with mitochondria (green) was detected in cancer cells (yellow fluorescent overlay) (FIG. 18A), and no other organelles such as the ER. This triggered hyperpolarization of the mitochondrial membrane and fusion-like aggregation (FIG. 18B) that impaired mitochondrial redistribution, ATP production and, as a result, F-actin polymerization (FIG. 18C). These "initiating events", during which cells remained viable (FIG. 18D), resulted in cell detachment, starting at 6 hours post-treatment (FIG. 18E), which was preceded by decreased surface expression of β1 integrin, the adhesion molecule that (along with α5) mediates binding to the fibronectin substrate (FIG. 18F). By 24 hours post-CT20p treatment, "effector events" caused by peptide-induced loss of substrate attachment were detected, including the activation of caspases (FIG. 18G), the induction of autophagy (FIG. 18H), and increased ROS production (FIG. 18I). Note that none of these "effector" events were detected earlier or upon treatment with HBPE-NPs alone, indicating that CT20p, and not the NPs, caused these effects. Cell death (anoikis), indicated by membrane asymmetry, was detectable in cancer cells by 48 hours (FIG. 18J). Similar results, such as mitochondrial localization, autophagosome formation or cell death, were not observed with a control epithelial cell line (FIGS. 19A-19C), indicating that the HBPE-NPs did not cause non-specific effects and that the lethal activity of the peptide was linked to cancer cells. These findings indicate that CT20p impairs cancer cell invasiveness through its actions on mitochondria and the cytoskeleton, which causes detachment-induced cell death.

Figure 20:
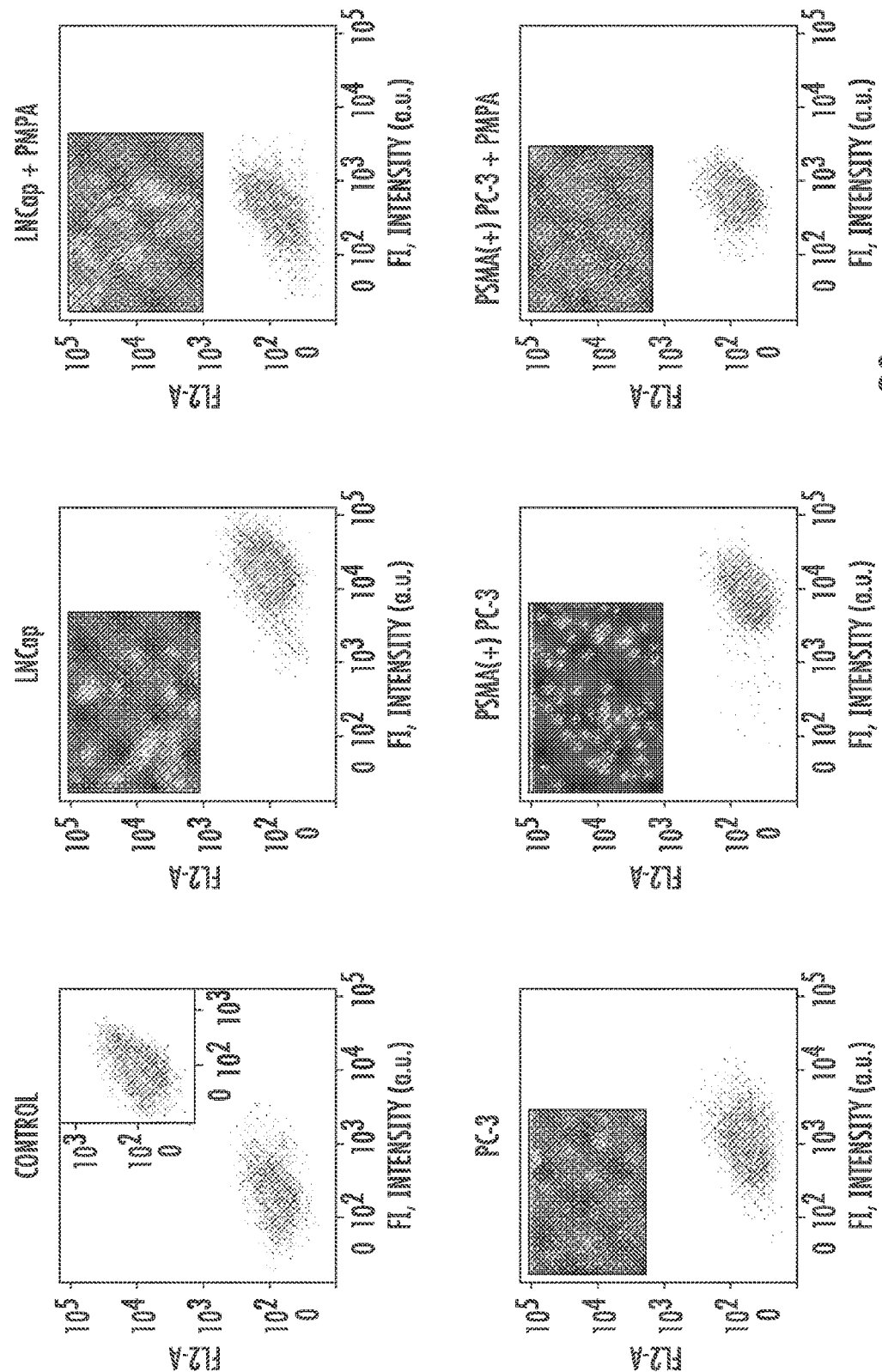
FIG. 20 shows the results of a FACS analysis used to assess the degree of targeting and PSMA-mediated cell internalization of Folate.HBPE(DiI)-NPs. Also shown are the corresponding fluorescence images.
Figure 21A:
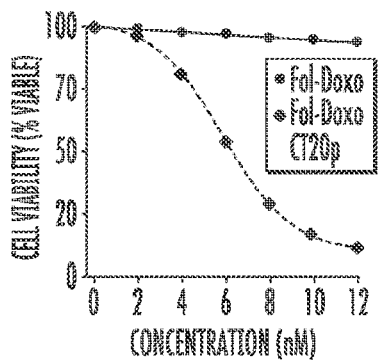
FIGS. 21A-21J show dose- (FIGS. 21A, 21C) and time- (FIGS. 21D, 21F) dependent cytotoxicity assay of PCa cells treated with Folate.HBPE(DiI)-NPs. PCa Cells: LNCap (FIGS. 21A, 21D), PSMA(+) PC3 (FIGS. 21B, 21E) and PC3 (FIGS. 21C, 21F).
Figure 21B:
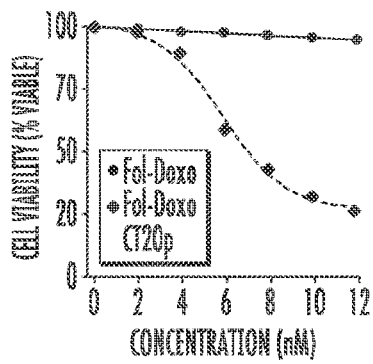
Figure 21C:
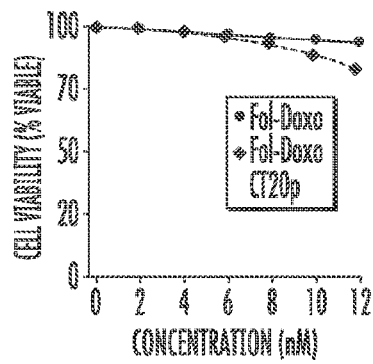
Figure 21D:
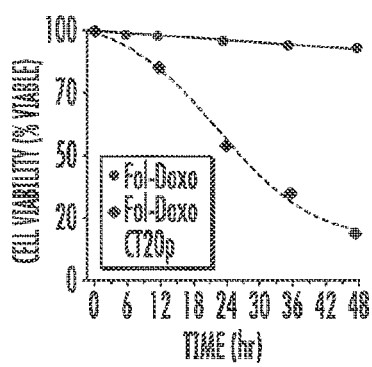
Figure 21E:
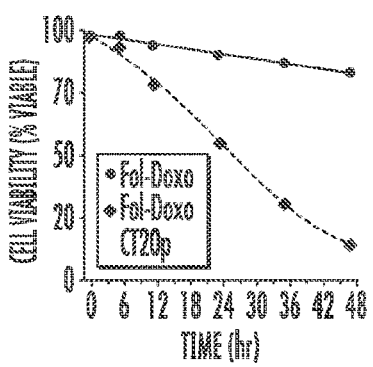
Figure 21F:
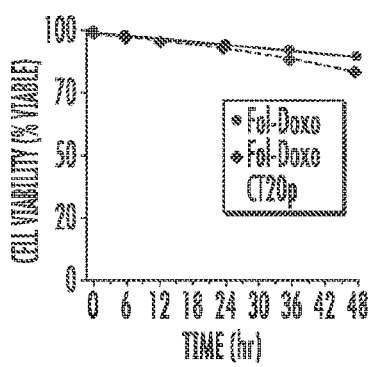
Figure 21G:
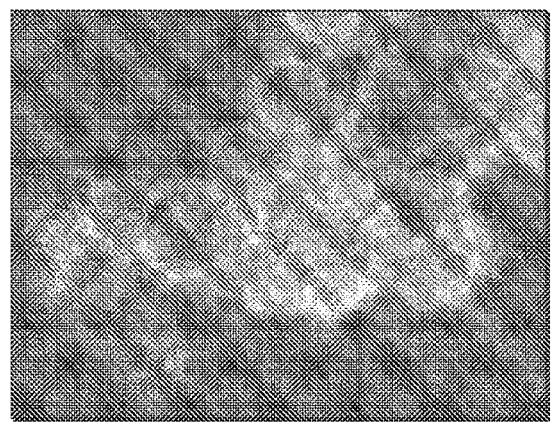
Figure 21H:
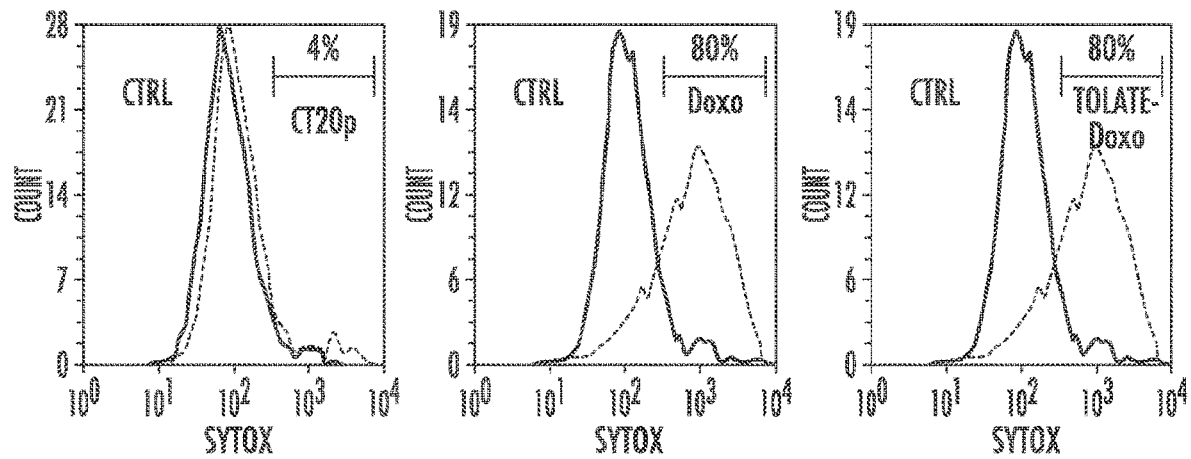

Folate-HBPE-NPs target PSMA in PCa cells. To visualize NP internalization into PSMA-expressing PCa cells, a fluorescent dye (DiI) was encapsulated within folate-HBPE-NPs. Cell-associated fluorescence was detected by flow cytometry and fluorescence microscopy in LNCaP (PSMA+) and PSMA(+)-PC-3 cells (FIG. 20). No internalization was observed in PSMA(−) PC-3 cells or in a PSMA inhibitor (PMPA) (FIG. 20). These results indicated that folate-conjugated NPs target PSMA and release a therapeutic cargo inside the cell. Next, folate-HBPE(CT20p)-NPs were synthesized to deliver CT20p to PCa cells via PSMA. Upon incubation of LNCaP cells with folate-HBPE(CT20p)-NP, a dose and time dependent response was observed, achieving cell death after 48 hours with nanomolar amounts of peptide in NPs (FIGS. 21A, 21D). Similar results were obtained with PSMA(+) PC-3 cells (FIGS. 21B, 21E). No cytotoxicity was observed in PSMA(−) PC-3 cells (FIGS. 21C, 21F) or when PMPA was used as PSMA inhibitor. These results show that the folate-decorated HBPE-NPs deliver CT20p to PCa via PSMA, achieving target specific cell death. Fluorescence microscopy of LNCaP cells using folate-HBPE(CT20p/DiI)-NP, showed significant cell associated DiI fluorescence, causing initial detachment and then death within 48 hrs (FIG. 21G), as measured by the uptake of a membrane permeability dye (Sytox) (FIG. 21H). Note that studies using controls, such as free CT20p (not taken up by cells) and untargeted HBPE-NPs to deliver CT20p (less effective), are known in the art.

Figure 21I:
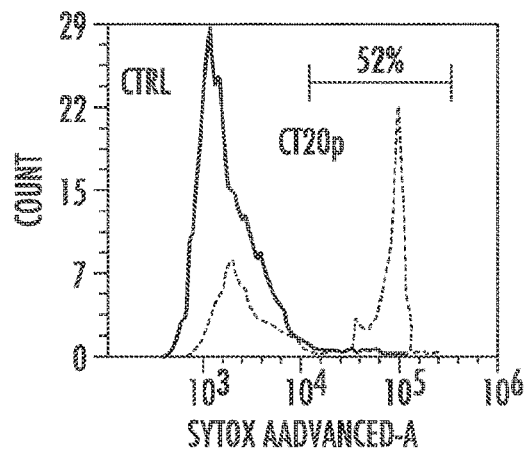
Figure 21J:
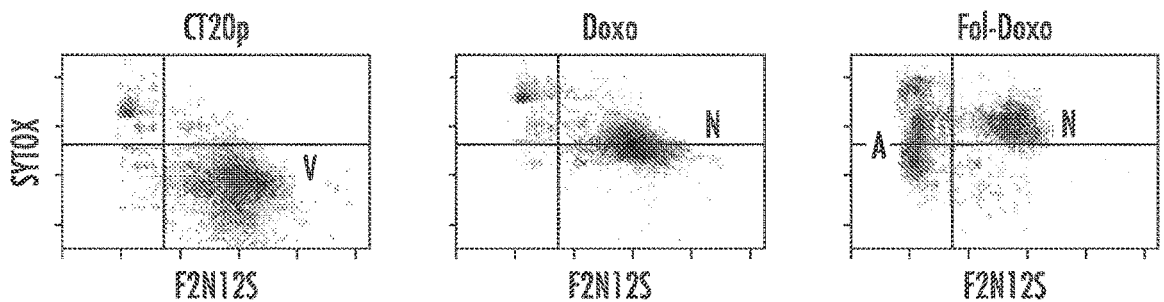

To study any effect that folate-HBPE (CT20p)-NPs may have on non-transformed cells, macrophages (RAW cells) were incubated with the folate-HBPE(CT20p)-NPs and cell death was assessed. FIGS. 21I and 21J show that macrophages were minimally affected when incubated with folate-HBPE(CT20p)-NPs for 48 hours (<4% dead) when compared to untreated cells (FIGS. 21I and 21J, left panels). As a control, the death of macrophages was observed upon treatment with the Folate-ss-Doxo probe or Doxorubicin (FIGS. 21I and 21J, right and middle panels). These results showed that Folate HBPE (CT20p)-NPs are not toxic to macrophages, while inducing cell death in cancer cells. Fluorescence microscopy studies confirmed the internalization of folate-HBPE(CT20p)-NPs by macrophages, indicating that when CT20p-containing NPs are taken up little change in the viability of nontransformed cells is observed.

Figure 22A:
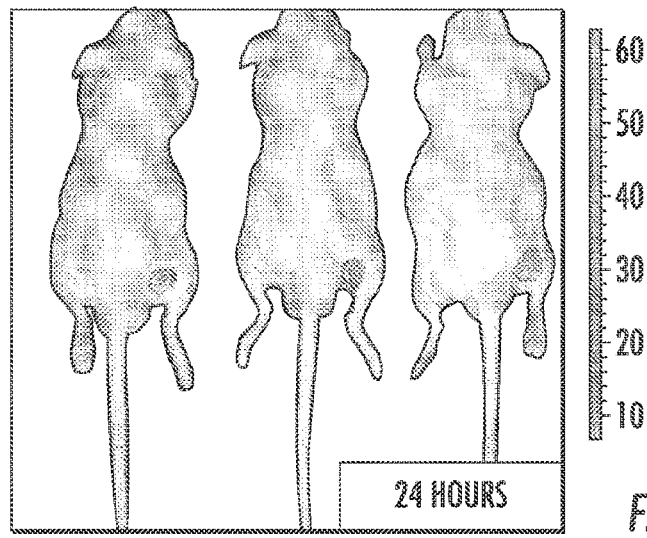
FIG. 22A depicts an image of mice that were injected subcutaneously (SC) with PSMA(+) (right flank) or PSMA (−) (left flank) PCa tumor cells. Upon tumor detection (~2 weeks), the mice were injected intravenously (IV) with PEG-(FOL)-HBPE-NPs (2 mg/kg/dose) containing a near IR dye (FIG. 22A) or CT20p (FIG. 22B). Mice were imaged after 24 hours (FIG. 22A) or sacrificed after 10 days (FIG. 22B).
Figure 22B:
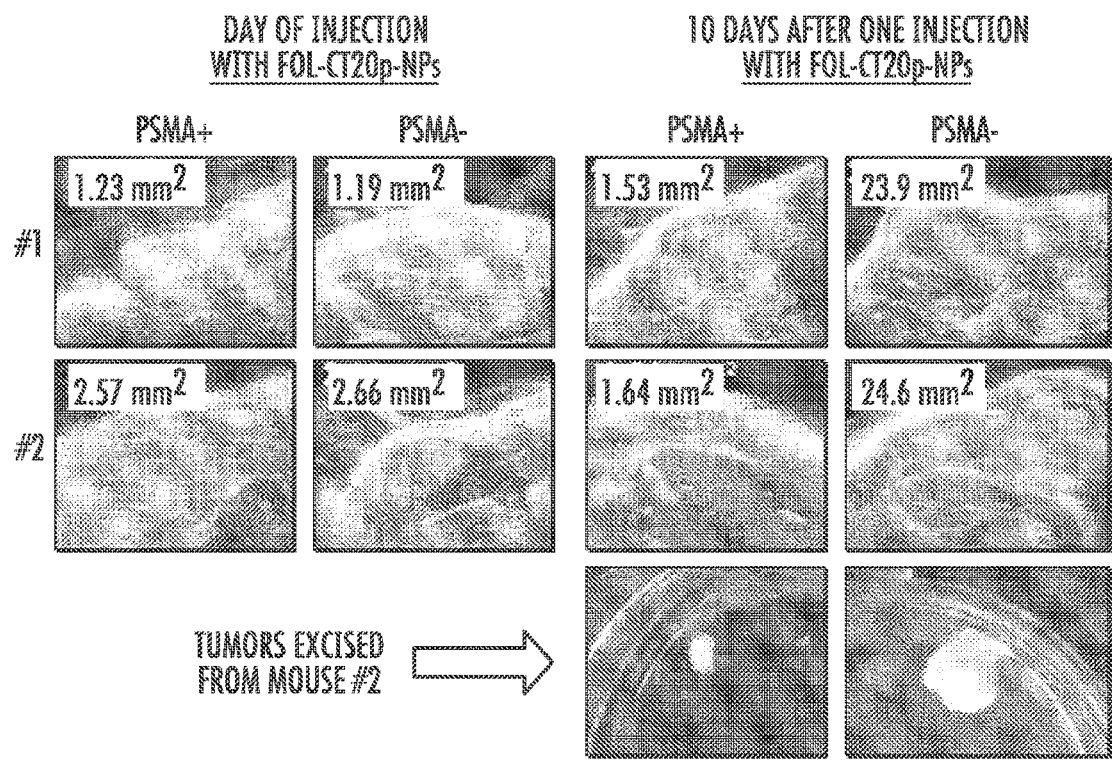
FIG. 22C shows an image of the tissue harvested from FIG. 22B for histological examination. Fragmented and necrotic tissue in the PSMA+ tumor is indicated by arrow and borders marked by a line.
FIG. 22D is a graph that summarizes a two week experiment in which mice (n=5) bearing PSMA+ tumors (SC) were IV injected once per week with FOL-HBPE-NPs (2 mg/kg/dose) that were empty or had CT20p and were compared to COOH-NPs (untargeted) with CT20p or FOL-targeted doxorubicin (DOX). *p<0.05. The mice were euthanized before the tumors ulcerated.
Figure 22C:
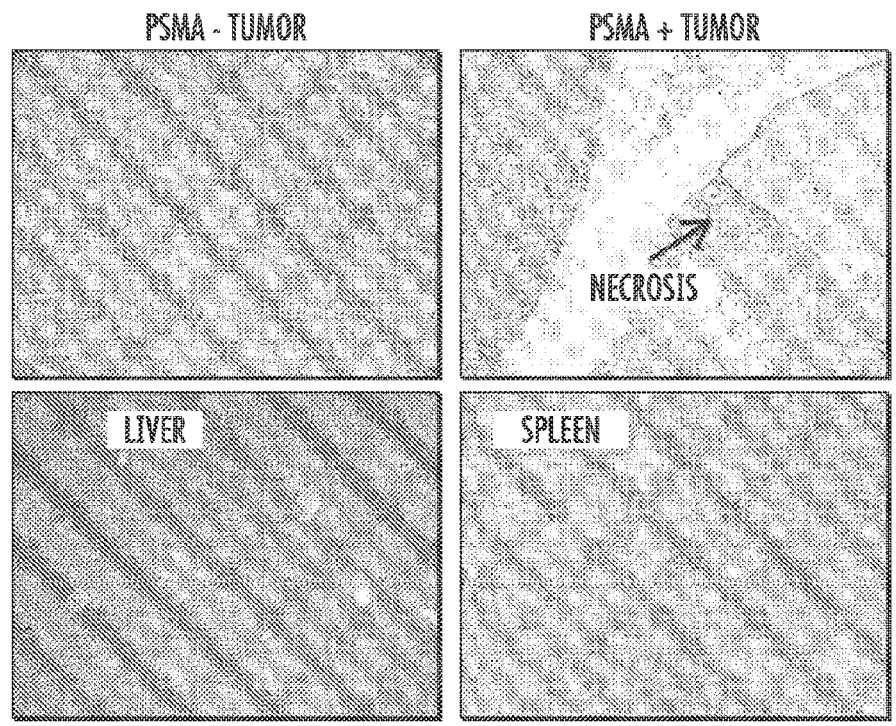
Figure 22D:
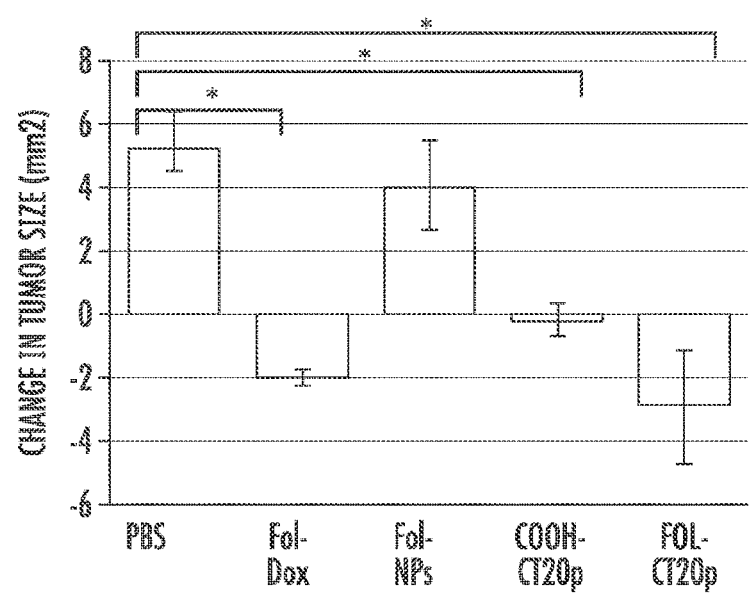

Next, PEGylated folate-HBPE-NPs were synthesized to examine in vivo PSMA-specific targeting using mice bearing right flank PSMA(+) PC3 and left flank PSMA(−) PC3 tumors. Tumors were allowed to grow for 2 weeks before treatment with one intravenous (IV) injection of folate-HBPE(DiR)-NPs, containing a near infrared dye (DiR) (2 mg/kg/dose). After 24 hrs, mouse fluorescence imaging showed a strong fluorescence signal in the PSMA(+) PCa tumors (FIG. 22A), while no fluorescence was observed in wild type PC3 tumors that lack PSMA. This experiment was repeated twice to confirm that the fluorescent signal was restricted to the PSMA+ tumors. These results demonstrated that folate-conjugated HBPE-NPs target PSMA expressing PCa tumors, with minimal off-target accumulation and that PEGylation of NPs does not interfere with ligand targeting. Next, the anti-tumor effect of the PSMA-targeting. PEGylated folate-HBPE(CT20p)-NPs was evaluated in mice bearing PSMA(+) and PSMA(−) PC3 tumors A single IV treatment with CT20p-containing NPs (2 mg/kg/dose or ~3.4 nM CT20p) caused significant regression of the PSMA-targeted tumors (FIG. 22B). Note that after 10 days, growth of PSMA-targeted tumors did not recur. Histological examination of tissues by a pathologist revealed fragmentation and areas of necrosis in the PSMA+ tumors not evident in the untargeted tumors or in the liver and spleen. (FIG. 22C). In the graph shown in (FIG. 22D), a summary of a two week mouse experiment shows that PEGylated FOL-HBPE (CT20p)-NPs, IV, injected once a week (2 mg/kg/dose or ~3.4 nM CT20p), effectively concentrated CT20p in PSMA+ tumors. Untargeted COOH-NPs also delivered CT20p to tumors, likely through the enhanced permeability and retention (EPR) effect, but efficacy was less due to reduced amounts in tumors and accumulation in the liver and spleen (detected by DiR fluorescence.). Once delivered to tumors, CT20p is more effective than drugs like Doxoyrubucin (Dox) (FIG. 22D). In total, the data indicates that PEGylated folate-HBPE-NPs deliver CT20p to PSMA(+) PCa cells and that particles persist in tumors, causing targeted tumor regression. This work provides the foundational support for the testing of the polyglutamate folate-HBPE-NPs as an improvement over the folate-targeted NPs to concentrate CT20p in PSMA(+) PCa tumors and metastatic sites.

In this experiment, the ability of polyglutamated folate-DFO-HBPE-NPs to deliver CT20p to PCa tumors and impair metastasis was investigated. In addition, the biological effect of CT20p upon the cytoskeleton and integrin signaling that promotes its anti-metastatic activities as well as the effectiveness of CT20p under hormone or castration conditions were examined. The murine model systems used will include xenografts of human PCa cell lines that express PSMA as well as PSMA-negative PCa cell lines. The polyglutamated folate DFO-HBPE(CT20p)-NPs from Experiment 2 that demonstrated the most selective PSMA targeting in PET imaging studies was used. As a model of PCa metastasis, an orthotopic PCa model in which luciferase expressing LNCap cell (LNCap-luc-M6) are implanted directly in the prostate was used (Scatena, C. D., et al., Imaging of bioluminescent LNCaP-luc-M6 tumors: a new animal model for the study of metastatic human prostate cancer. *The Prostate* 59, 292-303 (2004)). This model is ideal to study the progression of metastatic prostate cancer to lymph nodes and lungs by bioluminescence. In addition, as PCa primarily metastasize to the bones, a method where PCa bone (osseous) tumors are established by injecting PCa cells directly into a mouse tibia was used (Ulmert, D., et al., Imaging androgen receptor signaling with a radiotracer targeting free prostate-specific antigen. *Cancer discovery* 2, 320-327 (2012)). In addition, results using Doxorubicin (Doxo) or Folate-s-s-Doxo were compared to those obtained with polyglutamated folate HBPE(CT20p)NPs. The results indicated that polyglutamated folate HBPE-DFO[CT20p]-NPs target PSMA-expressing PCa cells, causing loss of cell adhesion and invasiveness, which will impair the development of metastasis.

Examining the Effects of CT20p Upon Cell Adhesion and Anoikis

An essential activity that promotes the invasiveness of metastatic cells is rearrangement of the cytoskeleton, which can be linked to integrin signaling. To demonstrate that CT20p alters this activity in PCa cells, the distribution of F-actin and G-actin with mitochondria (which produces the ATP that powers actin polymerization) in cells treated with polyglutamated folate HBPE-DFO[CT20p]-NPs (lead compounds from Experiment 2) was examined. At selected time points. PCa cells (Table 1) as well as control cells were treated with Mitotracker Red to visualize mitochondria and then were fixed on coverslips for staining with Alexa Fluor 647 phalloidin, a high-affinity F-actin probe, or Deoxyribonuclease 1, Alexa Fluor™ 488-conjugate for G-actin for imaging by confocal microscopy (Zeiss 710). To examine how integrin signaling was impaired by CT20p, the surface expression of integrins detected with fluorescence-conjugated antibodies (β1, CD29 and αVDβ3, CD51/61) by flow cytometry, was examined. Levels of additional integrins (αV or α5) were also evaluated by immunoblotting cell lysates. To determine whether cell detachment and the reduction in integrin levels could activate anoikis, the CytoSelect™ 96-well Anoikis Assay Kit was used and standard assays of cell migration and invasion were performed. Additionally, to test the effects of CT20p under conditions of directed migration, the cells described above were treated with conditioned media from 3T3 cells, which contains chemotactic factors.

Assessment of Tumor Regression Under Hormone and Castration Conditions

Since a hallmark of CRPC is the re-activation of androgen signaling, even after castration, it is important to test the effectiveness of CT20p as well as the ability of the PSMA targeting DFO-HBPE-NPs to deploy a therapeutic payload (CT20p) directly to the PCa tumors under castration or hormone signaling conditions. Results were compared with those obtained with free doxorubicin or folate-ss-doxorubicin. Again, the lead HBPE-NP preparations from Experiment 2 were used. Male SCID mice were used that are either intact or castrated and treated with testosterone (SC) or DHT pellet. SCID mice were injected SC with luciferase expressing LNCaP cells and, upon tumor growth, D-luciferin was injected prior to imaging (IVIS, Perkin Elmer). In all experiments. NPs without targeting ligand or without CT20p were used as controls. Mice were injected once every week, for 3-4 weeks, with control DFO-HBPE-NPs or PSMA-targeted DFO-HBPE(CT20p)-NPs Tumor growth was monitored by measuring the tumor size using a caliper or by ultrasound as well as by bio-luminescence as described above. In addition, blood was collected for weekly PSA measurements (with a commercially available ELISA), using the value prior to therapy as a baseline. The tumors were followed for 6 weeks or until reaching 1.5 cm m size (whichever came first). At experimental endpoints, remaining tumor tissue, as well as liver, spleen, kidney, lungs and brain, were collected and examined by immunohistochemistry (using J591 to identify PSMA) and also qRT-PCR and quantitative Western Blot for PSMA levels in the tumor to correlates with response to the targeted therapy. Tissues were then mounted for histological examination using 11 & E staining for detecting the presence of malignancy, treatment effect (absence or presence of necrosis).

Targeting PCa Metastasis in Mice

A previously reported orthotopic PCa mouse model was used in these experiments.[60] This model was developed by injecting LNCap-luc-M6 cells into the dorsolateral prostate lobes of male SCID-bg-mice. This model was used in order to visualize metastatic cells by bioluminescence Using this system, within a period of 16 weeks, a luciferase expressing PCa tumor developed in the prostate, as well as luciferase expressing metastatic lesions in nearby lymph nodes and lungs. Approximately $10^6$ LNCap-luc-M6 cells were injected directly into the prostate of SCID-bg-mice and the mice were monitored weekly by bioluminescence after injection of D-luciferin to detect the development of primary tumors and metastasis. Another set of mice were injected with PC3-luc2 as negative control as these cell lines did not express PSMA. After development of metastatic PCa in these mice. PSMA targeting DFO-HBPE(CT20p)NPs were injected and survival data was acquired. In the event that the signal from the primary tumor is too bright and prevents detecting the metastatic cells, the primary tumor can be blocked or removed. Next, since PCa metastasis occur more commonly in the bone, the capabilities of the PSMA targeting DFO-HBPE(CT20p) NPs to target tumors seeded to the bone were examined. To create bone tumors, the tibiae of mice were exposed and a small hole was drilled through the cortex into the marrow space using a stero-microscope. Once the cavity was accessed, concentrated PSMA(+) PC3 cells were slowly injected. In this model, the PSMA(+) PC3 cells were used, as PC3 is a cell line derived from human bone metastasis. After removal of back-flushed cells, the drill hole was closed with bone wax and the skin was closed with sutures. Once tumors were detected by X-ray CT, the mice were injected with the corresponding NPs and imaged as described herein. The mice were sacrificed and the number and mean-size of metastases was correlated with the read out obtained by imaging. Controls comprised mice bearing PSMA(+) tumors but injected with non-targeted DFO-HBPE-NPs. In addition, in another set of mice the tibiae were injected with wild-type PC3 cells to develop PSMA(−) bone metastasis as a negative control Toxicity to non-cancerous tissue was examined by histology and serum was recovered for clinical chemistry tests of liver and kidney function as described in Experiment 2.

Comparison with free Doxo and Folate-s-s-Doxo and Folate HBPE (Doxo)

Some of the mouse tumor models described herein were injected with free Doxo, Folate-s-s-Doxo or Folate HBPE (Doxo) (see FIGS. 22A-22D). Tumor regression also occurs with these therapeutics, but their corresponding efficacy in targeting the metastasis as well as any off-targeted tissue toxicity was assessed and compared to results obtained with the polyglutamated folate HBPE(CT20p) NPs. Toxicity to non-tumor tissue was examined as described herein.

Assessment of NP Localization by PET

To monitor localization of polyglutamated folate HBPE (CT20p) NPs to both primary and metastatic tumors, the theranostic version of the PSMA targeted HBPE (CT20p) NPs (with $^{89}$Zr) from Experiment 2 was used in some of the animal models described herein. PSMA expression levels at metastatic sites and tumor regression were imaged by X-ray CT and PET as described in Experiment 2.

In this experiment, the lead polyglutamated folate DFO-HBPE-NPs delivered CT20p via PSMA targeting to PCa, facilitating regression of the primary tumors and the metastatic lesions in the animal models studied, even in the castration and hormone signaling conditions. Minimal off-target toxicity was observed due to the specific PSMA targeting to PCa and the fact that CT20p was only cytotoxic to cancer cells. On the other hand, off-target toxicity was observed in mice treated with free Doxo, Doxo-s-s-Folate, or Folate HBPE (Doxo). Cytotoxic effects in response to the introduction of CT20p resulted in loss of F-actin and reduced integrin signaling which led to cell detachment and induction of death (e.g. anoikis) These events were fatal for metastatic cancer cells but did not occur in normal cells.

If using polyglutamated folate DFO-HBPE(CT20p) NPs, compared to folate-HBPE-Doxo, to impair metastasis is poor or the dose is toxic, the dose or delivery scheme can be modulated until metastasis inhibition is observed or biodistribution PET imaging data can be used to modify, targeting.

For an expected difference in means of at least 75% and a power of 95%, a sample size of 5-8 mice was calculated to account for biological variability in all in vivo experiments. The statistical core was performed as described in Experiment 1.

Example 3

In this aspect, a new theranostic (therapeutic and imaging) nanoparticle that encapsulates a no, el cytotoxic peptide. CT20p, for the treatment of prostate cancer is disclosed. Animal experiments were necessary to examine the effectiveness of the nanoparticle preparations after validation in in vitro cell culture experiments. Mice used in this study provide a model in which to test the cytotoxicity of nanoparticles loaded with peptides and develop optimal immune responses as follows:

| Crl: SHO-Prkdc$^{scid}$ Hr$^{hr}$ mice, males, 8-16 weeks of age | For completion of tasks in Experiment 2 = 130 mice |
|---|---|
| CB17.Cg-Prkdc$^{scid}$Lyst$^{bg-J}$/Crl mice, males, 8-16 weeks of age | For completion of tasks in Experiment 3 = 320 mice |

Subcutaneous Tumor Implantation and Treatment 5-10 million prostate cancer cells (PC3, LNCaP) were implanted in mice subcutaneously (sc) into the right or left flanks. Mice were monitored until tumors reached 10 to 15 mm$^2$ in size. Tumors were measured using calipers 2-3 times and ultrasound 2-3 times per week. Upon tumor detection, mice were injected intravenously with nanoparticles and controls as described in Experiment 2. In addition, each experiment also included a PBS control. The amount of nanoparticles delivered to mice were experimentally determined. Tumor size continued to be monitored after treatment for up to 21 days if tumors ulcerated. At the end of the study, animals were euthanized and tumors and other tissues (kidneys, spleen, liver, lungs and brain) were removed for evaluation. Although mice were monitored daily for visual signs of distress, mice were scored two-three times per week, and those showing distress were euthanized prior to the study endpoint. Mice euthanized prior to end of study were also dissected and anatomically evaluated.

In Vivo Toxicity and Pharmacokinetic (PK) Studies

Groups of mice (non-tumor) were intravenously treated weekly with escalating doses of nanoparticles (2-20 mg/kg/dose) and the mice were observed for changes in weight and food uptake. Blood was collected as described herein and sent for clinical chemistry analysis. After 12-13 weeks, mice were euthanized and organs were removed for histological analysis. For PK studies, groups of mice were intravenously treated with nanoparticles over a 24 hours period. Blood was withdrawn after 5, 15, 30, 1, 2, 4, 6, 8, 12, 18, and 24 hours and analyzed for clearance of peptide (CT20p) and nanoparticles.

Recovery of Serum and Urine

Blood (<0.5% animal body weight/wk) was drawn from and collected into I ml syringes (containing 3.2% sodium citrate) from the tail vein of mice. Mice were restrained for blood collection and a heat lamp was used when needed. Anesthesia is not normally required for this procedure. Following the bleeding procedure, mice were euthanized by $CO_2$. Other methods for drawing blood such as (retro-orbital bleed or heart puncture) can be adapted following the same handling procedure as described herein. Anesthesia (i.e. intraperitoneal administration of tribromoethanol (250 mg/kg, 0.2 ml volume) can be used in the event that these alternative methods are employed. For recovery of spontaneous urine, mice were placed in clean cage with plastic wrap and voided urine recovered. For terminal recovery of urine after mice were euthanized, direct puncture of the bladder with a needle using a syringe.

Implantation of Tumors Cells in Prostate

Male 6-8 week old male mice were used. Pre-surgery pain medication was injected according to animal facility's instructions (e.g. 0.1 mg/kg body weight subcutaneous Buprenex) At the time of surgery, animals were anesthetized with isoflurane. The lower abdominal region was disinfected and, using a sterile scalpel or sharpened sterile surgical scissors, a low midline abdominal incision of approximately 3-4 mm was made. The prostate lobes were identified and a 20 µl volume (~2.5×105 cells) solution was injected into the prostate gland. The muscle layer was closed with sutures and the skin with staples. Mice were imaged weekly for up to 4-6 weeks to monitor tumor growth. Treatment groups were tested as described above in Experiment 3.

Bone Tumor Model

Following the procedures described herein, male animals were anesthetized and cell suspensions were prepared. Injection volume per mouse was 20 µl containing 0.2-1.5×10$^6$ PC-3 cells. To determine optimal endpoints, variable numbers of cancer cells were injected intratibially and tumor growth was detected by radiographs at appropriate times post inoculation. For intra-tibial implantation of tumor cells, anesthetized mice were disinjected. The ankle (tibia and fibula) was rotated laterally and the knee bent so that the anterior crest of the tibial body was clearly visible through the skin. The syringe needle was aligned with the long axis of the tibia and the needle was inserted percutaneously through the knee joint to place the needle tip on the proximal tuberosity of tibia Drilling occurred by rotating the syringe (half to ¾ turn). Once the needle tip had advanced to the correct position, the syringe was released and the syringe stayed still. X-ray images were used to confirm correct position of the needle within the bony trabeculae near the growth plate. The drilling needle was retracted and the syringe was loaded with the cell suspension. The injection syringe needle was placed in the drilled position and suspension was slowly injected Tumor growth was followed up by X-ray images Monitoring of Tumor Growth For imaging tumors in mice, mice were anesthetized and fluorescence imaging was detected with the Carestream Multi Spectral FX imaging station. Examination of luminescence was performed with the IVIS system. Ultrasound imaging to locate the tumor and perform needle guided injections was done using the Visual Sonics Vivo 2100. Following imaging, mice were observed for recovery and were returned to the housing room.

Number of Animals

The use of mice in the studies is justified by the extensive database of information available to support studies. SCID mice are routinely used for implantation of prostate tumor cells and the murine model of bone metastatic disease is a well-established system to study tumor invasions. Numbers of animals used in experiments were determined using a statistical power analysis based on results achieved in the pilot study. A significance level (alpha) of 0.05 (two-tailed) was used. A power (beta) of 95% was chosen to determine sample size. Statistical analysis (GraphPad StatMate, Prism) determined that a sample size of 8 mice in each group had a 95% power to detect a difference between the experimentally determined standard deviation and test values with a significance level of 5%. All experiments were repeated three times for reproducibility.

Experiment 2 required 48 SCID mice to test the in vivo toxicity of 2-3 lead compounds and controls and 88 mice (~11 time points) to complete the PK studies.

Experiment 3 required 320 mice to develop the castration model and the intra-prostate and intra-tibia orthotropic models as described for testing of 2-3 lead compounds and controls.

By adding a few mice for biological variability (such as tumors not taken), a total of ~480 mice were estimated for the period of 4 years.

Veterinary Care of the Animals

Veterinary care at the University of Central Florida (UCF) transgenic animal facility at Lake Nona was provided by in-house animal care technicians and a licensed veterinarian. The new facility was fully accredited by the Association of Assessment and Accreditation of Animal Care, International (AAALAC) in 2011 and has an approved assurance on file with the Office of Laboratory Animal Welfare, NIH (OLAW). All mice were housed under pathogen-free conditions. Animal care was provided in accordance with the procedures outlined in the "Guide for the Care and Use of Laboratory Animals" (NIH Publication No. 86-23, 1985). Animals were identified by cage card/ear notch. Immuno-deficient mice were housed in sterile cages and handled under aseptic conditions.

Mice experienced minimal pain or distress Mice were placed in a comfortable restraining device for tail vein injections with nanoparticle suspensions. For imaging and the orthotopic model, mice were anesthetized with 2% isoflurane with 1% oxygen in an induction changer, and, during the procedure, the anesthetized state was maintained with a nose cone. All procedures were performed using the volatile fluorocarbon, isoflurane, involved a precision vaporizer (which was calibrated and certified within 12 months of the experiment as required by IACUC policy) in an induction chamber followed by use of a nose cone. Depth of anesthesia was confirmed by observing respiration rate and verifying absence of response to ear, toe, and/or tail pinch. Response evaluated included withdrawal as well as an increase or change in respiratory rate and/or pattern.

After the implantation of tumors, mice were observed daily for signs of distress and body condition scoring (BCS, see below) used to assess problems. If tumors were >10% of the mouse's body size (~1 cm in diameter), became ulcerated or interfered with normal functions, the mouse was euthanized.

Example of BCS guidelines are as follows:
5: The mouse is obese, and bones cannot be felt at all;
4: The mouse is well-fleshed, and bones are barely felt;
3: The mouse is in optimal condition. Bones are palpable but not prominent;
2: The mouse is becoming thin and bones are prominent. This category may be further divided subjectively as +2, 2, and −2. Euthanasia is recommended for BCS of −2.
1: Muscle wasting is advanced, fat deposits are gone, and bones are very prominent. Euthanasia is mandatory.

A body condition score of 2 or 1 indicates a decline in overall condition, and euthanasia is recommended. A weight loss of 10-15% within a few days or an overall weight-loss of 20% is also an indication for euthanasia.

Animals were euthanized if evidence of pain or distress was evident or if the tumor was greater than 10% of the animal body weight. Animals were sacrificed before tumor ulceration occurs. Euthanasia was considered for animals exhibiting any of these signs of distress. Euthanasia was performed by $CO_2$ asphyxiation in an inhalation chamber. This method is consistent with the recommendations of the Panel on Euthanasia of the American Veterinary Medical Association. Mice were confirmed to have no signs of responsiveness, respiration or heart beat prior to collection. Death was insured by a second method such as thoracic puncture or cervical dislocation.

Disclosed herein is a novel theranostic approach for breast cancer, using a polymeric nanoparticle carrying DFO-$^{89}$Zr as contrast agent and the cytotoxic peptide CT20p. Animal experiments were used to evaluate the theranostic efficacy of the lead preparation after in vitro experiments. The correlation of the induced changes in T1 from baseline with the change in tumor volume after dose finding studies was tested. It was determined that a total of 50 animals were needed. SCID beige mice, male animals (since these are prostate tumors), ca. 3 weeks old were used A sample size calculation based on the difference in means and an expected 100% difference in means revealed that 6 animals per group were needed for a power of 95% and a p-values of 0.05 in the imaging experiments. There were 2 main sets of animal experiments; these are detailed in Experiment 2.

Experiment 2 required: For dose finding studies, 3 different doses in each 6 animals and one control for a total of 24 animals. For imaging studies, 2 doses of particles and one control was required with 6 mice each for a total of 18 mice. The total number of animals was therefore 42. To adjust for biological variability (such as tumors not taken), a total of 50 mice were used.

Memorial Sloan-Kettering Cancer Center's animal care and use program is administered by the Research Animal Resource Center (RARC) as one of the core facilities of MSKCC The program has been fully accredited by the Association of Assessment and Accreditation of Animal Care, International (AAALAC) since 1%7, is registered with the USDA, and has an approved assurance on file with the Office of Laboratory Animal Welfare, NIH (OLAW). RARC is staffed by board-certified laboratory animal veterinarians and pathologists, veterinary and animal care technicians, management, and administrative support staff. Veterinary staff is available 24 hours a day, 7 days a week to address emergencies. The program is supported by the Laboratory of Comparative Pathology, which provides anatomic and clinical pathologic evaluation of animals, tissues, and fluids in support of animal health and the use of animal models.

The animal resource program is housed in three state-of-the-art facilities occupying a total of 62,500 net ft2 of usable space. All vivaria contain barrier rodent housing facilities. One also supports the housing and use of large animal species. Specialized facilities for the use of animal models exposed to biological and hazardous chemical agents and for conducting surgical procedures in large and small animals are available. Multi-modality imaging suites containing computerized tomography (CT) scanners, optical instruments (bioluminescence, fluorescence and optical tomography), as well as PET and a SPECT/CT scanner are available for imaging large and/or small animals. These scanners are all housed directly within the animal facility in the Zuckerman research center. Small animal ultrasound scanner and a 4.7 T and a 7 T MRI scanners are also available to image and conduct spectroscopic studies in small animal models. Specialized housing rooms for maintaining aquatic species are also available.

All procedures were performed under inhalational anesthesia using the volatile fluorocarbon isoflurane, administered using a precision vaporizer (which was calibrated and certified within 12 months of the experiment as required by IACUC policy) in an induction chamber followed by use of a nose cone. Waste anesthetic gas was scavenged by using an activated carbon canister or by working under a fume hood, scavenging snorkel, or a biological safety cabinet equipped with an activated carbon filter. Depth of anesthesia was confirmed by observing respiration rate and verifying absence of response to ear, toe, and/or tail pinch. Response evaluated included withdrawal as well as an increase or change in respiratory rate and/or pattern.

While on treatment or after having tumor implanted, mice were monitored at least every other day for evidence of toxicity, pain, morbidity, loss of body weight (>10%), dehydration, poor grooming and/or excessive tumor burden resulting from tumor implantation or treatment. If required, pain was alleviated with buprenorphine injected subcutaneously as needed, under guidance of the veterinarian service.

Animals were euthanized if evidence of pain or distress was evident or if the tumor was greater than 10% of the animal body weight. Animals were sacrificed before tumor ulceration occurred. Euthanasia was considered for animals exhibiting any of these signs of distress. Euthanasia was performed by $CO_2$ asphyxiation in an inhalation chamber. This method is consistent with the recommendations of the Panel on Euthanasia of the American Veterinary Medical Association.

What is claimed is:

1. A nanoparticle for drug delivery, comprising: a hyperbranched polyester (HBPE) nanoparticle having a hydrophobic interior, polyglutamate folate ligands conjugated to the nanoparticle, one or more PET detectable isotopes, and a therapeutic agent, wherein the therapeutic agent is an anti-metastatic agent, antiandrogenic agent, anti-neoplastic agent, or a radiosensitizer.

2. The nanoparticle of claim 1, wherein the therapeutic agent is the anti-metastatic agent.

3. The nanoparticle of claim 1, wherein the therapeutic agent is the antiandrogenic agent.

4. The nanoparticle of claim 1, wherein the therapeutic agent is the anti-neoplastic agent.

5. The nanoparticle of claim 1, wherein the therapeutic agent is the radiosensitizer.

6. The nanoparticle of claim 1, wherein the nanoparticle comprises desferrioxamine (DFO).

7. The nanoparticle of claim 1, wherein the PET detectable isotope is $^{89}$Zr or $^{64}$Cu.

8. The nanoparticle of claim 1, wherein the nanoparticle further comprises PEG.

9. A method of administering a therapeutic agent to a subject, comprising: administering to the cancer subject the nanoparticle of claim 1.

* * * * *

SEQUENCE LISTING

```
<160> NUMBER OF SEQ ID NOS: 6

<210> SEQ ID NO 1
<211> LENGTH: 20
<212> TYPE: PRT
<213> ORGANISM: Artificial Sequence
<220> FEATURE:
<223> OTHER INFORMATION: Synthetic construct

<400> SEQUENCE: 1

Val Thr Ile Phe Val Ala Gly Val Leu Thr Ala Ser Leu Thr Ile Trp
1               5                   10                  15

Lys Lys Met Gly
            20

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Ala Ser Leu Thr Ile Trp Lys Lys Met Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Val Thr Ile Phe Val Ala Gly Val Leu Thr
1               5                   10

<210> SEQ ID NO 4
<211> LENGTH: 7
<212> TYPE: PRT
<213> ORGANISM: Artificial Sequence
<220> FEATURE:
```

```
<223> OTHER INFORMATION: Synthetic construct

<400> SEQUENCE: 4

Val Thr Ile Phe Val Ala Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic construct

<400> SEQUENCE: 5

Ile Phe Val Ala Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic construct

<400> SEQUENCE: 6

Ile Trp Lys Lys Met Gly
1               5
```